(12) United States Patent
Kusano et al.

(10) Patent No.: US 9,085,589 B2
(45) Date of Patent: Jul. 21, 2015

(54) CEPHEM DERIVATIVE

(75) Inventors: Hiroki Kusano, Toyonaka (JP); Kenji Yamawaki, Toyonaka (JP)

(73) Assignee: SHIONOGI & CO., LTD., Osaka (JP)

(*) Notice: Subject to any disclaimer, the term of this patent is extended or adjusted under 35 U.S.C. 154(b) by 11 days.

(21) Appl. No.: 13/642,959

(22) PCT Filed: Apr. 27, 2011

(86) PCT No.: PCT/JP2011/060259
§ 371 (c)(1),
(2), (4) Date: Dec. 17, 2012

(87) PCT Pub. No.: WO2011/136268
PCT Pub. Date: Nov. 3, 2011

(65) Prior Publication Data
US 2013/0096299 A1 Apr. 18, 2013

(30) Foreign Application Priority Data
Apr. 28, 2010 (JP) ................. 2010-104035

(51) Int. Cl.
| | | |
|---|---|---|
| A61K 31/546 | (2006.01) | |
| C07D 501/56 | (2006.01) | |
| C07D 501/42 | (2006.01) | |
| C07D 501/44 | (2006.01) | |
| C07D 501/46 | (2006.01) | |
| C07D 519/00 | (2006.01) | |
| C07D 519/06 | (2006.01) | |
| C07D 501/54 | (2006.01) | |

(52) U.S. Cl.
CPC ............ *C07D 501/56* (2013.01); *C07D 501/42* (2013.01); *C07D 501/44* (2013.01); *C07D 501/46* (2013.01); *C07D 501/54* (2013.01); *C07D 519/00* (2013.01); *C07D 519/06* (2013.01)

(58) Field of Classification Search
None
See application file for complete search history.

(56) References Cited

U.S. PATENT DOCUMENTS

| 4,647,556 A | 3/1987 | Lattrell et al. |
|---|---|---|
| 5,055,462 A | 10/1991 | Davies et al. |
| 5,095,012 A | 3/1992 | Okita et al. |
| 5,126,336 A | 6/1992 | Imae et al. |
| 5,143,910 A | 9/1992 | Onoue et al. |
| 5,234,920 A | 8/1993 | Okita et al. |

FOREIGN PATENT DOCUMENTS

| DE | 25 19 400 | 3/1976 |
|---|---|---|
| EP | 0 114 752 | 8/1984 |
| EP | 0 168 177 | 1/1986 |
| EP | 0 211 656 | 2/1987 |
| EP | 0 305 111 | 3/1989 |
| EP | 0 376 724 | 7/1990 |
| EP | 1 489 084 | 12/2004 |
| EP | 2 341 053 | 7/2011 |
| JP | 57-118588 | 7/1982 |
| JP | 58-162592 | 9/1983 |
| JP | 62-158291 | 7/1987 |
| JP | 2-15090 | 1/1990 |
| JP | 2-28185 | 1/1990 |
| JP | 2-28187 | 1/1990 |
| JP | 2-117678 | 5/1990 |
| JP | 2-275886 | 11/1990 |

(Continued)

OTHER PUBLICATIONS

Bryskier. *Clinical Microbiology and Infection*, vol. 3, Supplement 1, Apr. 1997, pp. S1-S6.

(Continued)

*Primary Examiner* — Golam M M Shameem
*Assistant Examiner* — Laura Daniel
(74) *Attorney, Agent, or Firm* — Hamre, Schumann, Mueller & Larson, P.C.

(57) ABSTRACT

Provided is a cephem compound which has a wide antimicrobial spectrum, and in particular exhibits potent antimicrobial activity against beta-lactamase producing Gram negative bacteria, and a pharmaceutical composition comprising the same. The cephem compound has the formula (I):

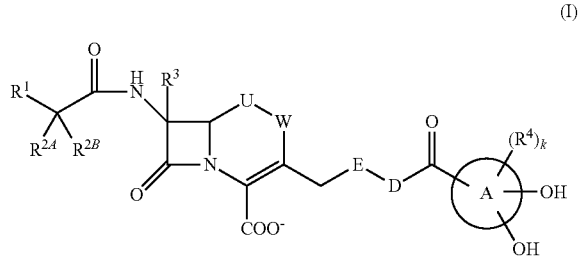

where W and U are as defined in the specification; $R^1$ is as defined in the specification; $R^{2A}$ and $R^{2B}$ are as defined in the specification, provided that $R^{2A}$ and $R^{2B}$ are not taken together to form an optionally substituted oxime group when $R^1$ is aminothiazole or aminothiadiazole optionally protected at the amino group; ring A is a benzene ring or a 6-membered aromatic heterocyclic group having 1-3 nitrogen atoms; $R^3$ is a hydrogen atom, —$OCH_3$ or —NH—CH(=O); k is an integer from 0 to 2; $R^4$ is as defined in the specification; and D and E are as defined in accordance with a) or b) described in the specification.

22 Claims, No Drawings

(56) References Cited

FOREIGN PATENT DOCUMENTS

| | | |
|---|---|---|
| JP | 4-364189 | 12/1992 |
| JP | 5-213971 | 8/1993 |
| JP | 5498393 | 3/2014 |
| WO | WO 92/21683 | 12/1992 |
| WO | WO 2007/096740 | 8/2007 |
| WO | WO 2007/119511 | 10/2007 |

OTHER PUBLICATIONS

Silley et al. *Antimicrobial Agents and Chemotherapy*, vol. 34, No. 9, Sep. 1990, pp. 1806-1808.

Yamano et al.. "Ferric iron transport system of *Pseudomonas aeruginosa* PA01 that functions as the uptake pathway of a novel catechol-substituted cephalosporin, S-9096". *Appl. Microbiol. Biotechnol.*, vol. 40, pp. 892-897 (1994).

Takeda et al. "In Vitro Antibacterial Activity of a New Cephalosporin, FR295389, against IMP-type Metallo-β-lactamase-producers". *J Antibio.*, vol. 61, No. 1., pp. 36-39 (2008).

Hashizume et al. "Comparison of Transport Pathways of Catechol-Substituted Cephalosporins, BO-1236 and BO-1341, Through the Outer Membrane of *Escherichia Coli*". *The Journal of Antibiotics*, vol. 43, No. 12, pp. 1617-1620 (1990).

Weissberger et al. "L-658,310, A New Injectable Cephalosporin". *The Journal of Antibiotics*, vol. 42, No. 5, pp. 795-806 (1989).

Branch et al. "Studies on Semi-Synthetic 7 α-Formamidocephalosporins". *The Journal of Antibiotics*, vol. 40, pp. 646-651 (1987).

CEPHEM DERIVATIVE

TECHNICAL FIELD

The compounds of the subject invention are related to Cephem compounds, which have a wide antimicrobial spectrum against Gram negative bacteria and Gram positive bacteria, and in particular exhibit potent antimicrobial activity against beta-lactamase producing Gram negative bacteria, and pharmaceutical compositions comprising the same.

BACKGROUND ART

To date, a variety of beta-lactam drugs have been developed and beta-lactam drugs have become clinically extremely important antimicrobial drugs. However, there are increasing number of bacterial types which have obtained resistance against beta-lactam drugs by producing beta-lactamase, which degrade beta-lactam drugs.

According to the Ambler molecular classification, beta-lactamases are largely classified into four classes. Specifically, these are Class A (TEM type, SHV type, CTX-M type and the like), Class B (IMP type, VIM type, L-1 type and the like), Class C (AmpC type) and Class D (OXA type and the like). Amongst these, Classes A, C and D types are largely classified into serine-beta-lactamase, on the other hand, Class B type is classified into metallo-beta-lactamase. It has been known that both have respectively different mechanisms to each other in terms of hydrolysis of beta-lactam drugs.

Recently, clinical problem has been occurring due to the existence of Gram negative bacteria which have become highly resistant to a number of beta-lactam drugs including Cephems and Carbapenems by producing Class A (ESBL) and D types serine-beta-lactamases which have an extended substrate spectrum, and Class B type metallo-beta-lactamase which have an extended substrate spectrum. Particularly, metallo-beta-lactamase is known to be one of the causes of obtaining multidrug-resistance in Gram negative bacteria. Cephem compounds which exhibit intermediate activity against metallo-beta-lactamase producing Gram negative bacteria are known (e.g., Patent Document 1 and Non-Patent Document 1). However, there is a demand for development of Cephem compounds which exhibit more potent antimicrobial activity, in particular more effective against a variety of beta-lactamase producing Gram negative bacteria.

One of the known antimicrobials having high anti-Gram negative bactericidal activity is Cephem compounds having a catechol group intramolecularly (e.g., Non-patent Documents 2-4). The action thereof is that the catechol group forms a chelate with $Fe^{3+}$, thereby the compound is efficiently incorporated into the bacterial body through the $Fe^{3+}$ transportation system on the cellular membrane (tonB-dependent iron transport system). Therefore, research has been conducted on compounds having catechol or similar structure thereto, on the 3-side chain or 7-side chain moiety on the Cephem backbone.

Patent Documents 2-8 and Non-patent Document 5 describe compounds having a partial structure of the 7-side chain and a quaternary salt structure on the Cephem backbone. However, these documents merely describe a pyridinium structure, and merely disclose compounds having a formamide group at the 7-position in most cases. Furthermore, for example, most compounds disclosed in Patent Document 2 have a penicillin structure.

Non-patent document 1 and Patent Documents 8-12 and 15 describe catechol type derivatives having a catechol group on the 3-side chain moiety on the Cephem backbone. Patent Documents 10, 11, 13 and 14 describe pseudo-catechol type derivatives having a hydroxypyridone group on the 3-side chain moiety on the Cephem backbone. Patent Documents 16 and 17 disclose Cephem compounds having a quaternary ammonium group, but do not describe a catechol type derivative.

Moreover, in the above documents, which describe Cephem compounds having a catechol group in their structure, there is no description of Class B type metallo-beta-lactamase, and specific antimicrobial activity against a wide variety of Gram negative bacteria including Class B type.

On the other hand, the present applicant filed an application of Cephem compounds having catechol type substituents (International Patent Application PCT/JP2009/068400). Furthermore, the present applicant has already filed an application relating to Cephem antimicrobial agent having potent antimicrobial activity against beta-lactamase producing Gram negative bacteria (Japanese Patent Application Ser. Nos. 2010-087130 and 2010-087131).

PRIOR ART DOCUMENT

Patent Documents

Patent Document 1: WO2007/119511 A1
Patent Document 2: DE 2519400 A1
Patent Document 3: JP 57-118588 A
Patent Document 4: EP 0114752 A2
Patent Document 5: EP 0168177 A2
Patent Document 6: EP 0211656 A2
Patent Document 7: EP 0305111 A2
Patent Document 8: JP 4-364189 A
Patent Document 9: JP 3-173893 A
Patent Document 10: JP 2-15090 A
Patent Document 11: JP 2-28187 A
Patent Document 12: JP 2-117678 A
Patent Document 13: JP 6-510523 A
Patent Document 14: JP 5-213971 A
Patent Document 15: JP 2-28185 A
Patent Document 16: WO2007/096740 A1
Patent Document 17: WO2003/078440 A1

Non-Patent Documents

Non-patent document 1: Applied Microbiology and Biotechnology (1994), 40(6), 892-7
Non-patent document 2: The Journal of Antibiotics, vol. 61, pp. 36-39 (2008)
Non-patent document 3: The Journal of Antibiotics, vol. 43, pp. 1617-1620 (1990)
Non-patent document 4: The Journal of Antibiotics, vol. 42, pp. 795-806 (1989)
Non-patent document 5: The Journal of Antibiotics, vol. 40, pp. 646-651 (1987)

SUMMARY OF INVENTION

Problems to be Solved by the Invention

The subject invention provides Cephem compounds which exhibit potent antimicrobial spectrum against a variety of bacteria including Gram negative bacteria and/or Gram positive bacteria. Preferably, the subject invention provides Cephem compounds which exhibit potent antimicrobial spectrum against both Gram negative bacteria and Gram positive bacteria. More preferably, the subject invention provides Cephem compounds which exhibit potent antimicrobial activity against beta-lactamase producing Gram negative bacteria. Still more preferably, the subject invention provides Cephem compounds which exhibit potent antimicrobial activity against multidrug-resistant bacteria, in particular, Class B type metallo-beta-lactamase producing Gram negative bacteria. Most preferably, the subject invention provides Cephem compounds which exhibit effective antimicrobial activity against extended-spectrum beta-lactamase (ESBL) producing bacteria.

Means for Solving the Problem

The subject invention provides Cephem compounds which have solved the above-mentioned problems by having the following structure:
(Item 1)
A compound of the formula:

[Formula 1]

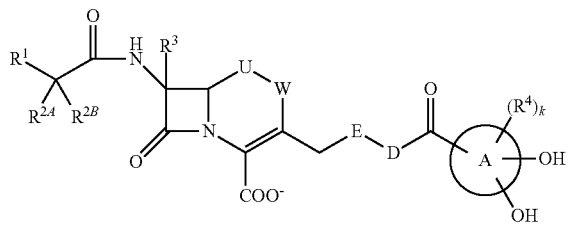

(I)

or an ester, an protected compound at the amino on the ring in the 7-side chain, a pharmaceutically acceptable salt, or a solvate thereof,
wherein
W is —$CH_2$—, —S—, or —O—; provided that
a) when W is —$CH_2$—, then U is —$CH_2$—, —S—, or —O—, and
b) when W is —S— or —O—, then U is —$CH_2$—;
$R^1$ is an optionally substituted carbocyclic group, or optionally substituted heterocyclic group;
with regard to $R^{2A}$ and $R^{2B}$,
a) $R^{2A}$ is a hydrogen atom, optionally substituted amino group, —$SO_3H$, optionally substituted aminosulfonyl group, carboxyl group, optionally substituted lower alkyloxycarbonyl group, optionally substituted carbamoyl group, hydroxyl group, or a substituted carbonyloxy group; and $R^{2B}$ is a hydrogen atom, or
b) $R^{2A}$ and $R^{2B}$ are taken together to form an optionally substituted alkenyl group, or optionally substituted oxime group,
provided that when $R^1$ is an aminothiazole of which the amino group is optionally protected, or an aminothiadiazole of which the amino group is optionally protected, $R^{2A}$ and $R^{2B}$ are not taken together to form an optionally substituted oxime group;
ring A is a benzene ring, or 6-membered aromatic heterocyclic group having 1-3 nitrogen atoms;
$R^3$ is a hydrogen atom, —$OCH_3$, or —NH—CH(=O);
k is an integer from 0 to 2;
each $R^4$ is independently hydrogen atom, halogen, hydroxyl group, —CN, —C(=O)—$R^6$, —C(=O)—OH, —C(=O)—$OR^6$, or —$OR^6$;
$R^6$ is a lower alkyl or halo(lower)alkyl; and
with regard to D and E, a) D is a single bond, —N($R^8$)—, or —$R^7$—N($R^8$)— wherein $R^7$ is an optionally substituted lower alkylene, and $R^8$ is a hydrogen or lower alkyl; and E is an optionally substituted quaternary ammonium group of the formula selected from the following formulae (1) to (40) and (42) to (53); or
b) D has the formula:

[Formula 2]

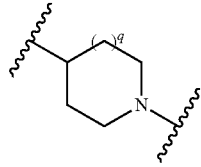

wherein q is an integer of 0 or 1, and E has the formula of a quaternary ammonium group represented by the following formula (10) or (41); and The formulae of the quaternary ammonium group of E (wherein the left side of the following substituents binds with methylene and the right side thereof binds with D) are as follow:

[Formula 3]

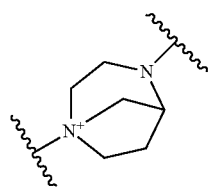
(1)

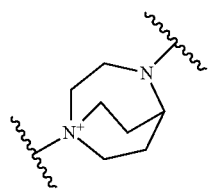
(2)

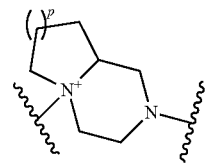
(3)

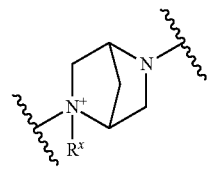
(4)

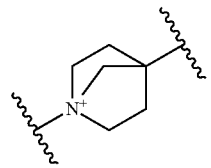
(5)

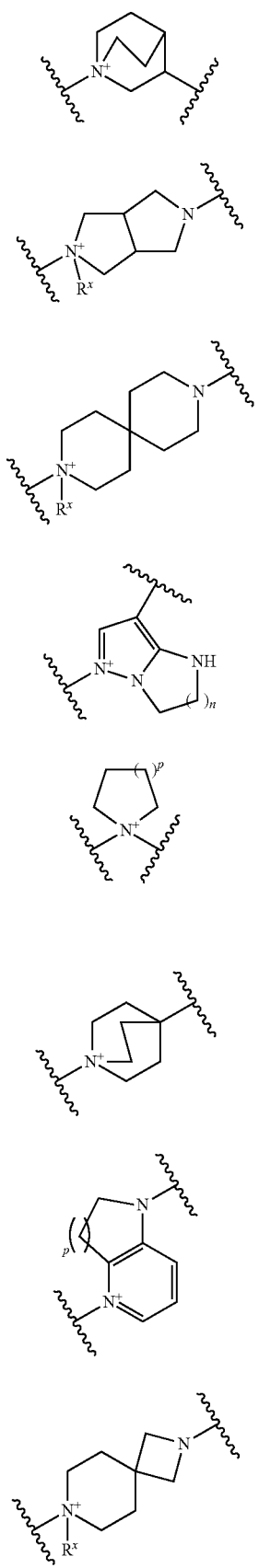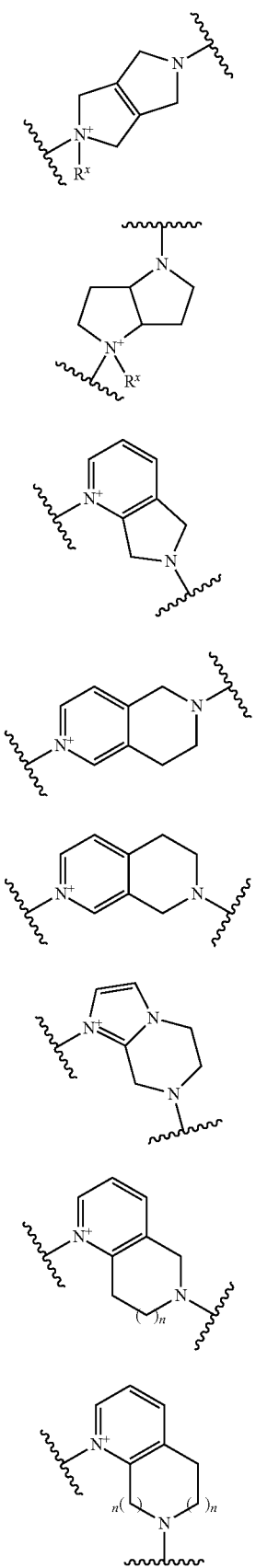

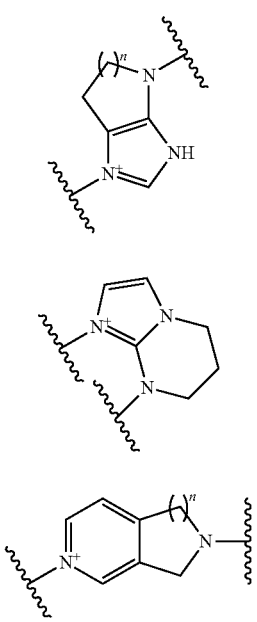
(22)
(23)
(24)
(25)
(26)
(27)
(28)
[Formula 4]
(29)
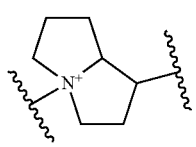
(30)
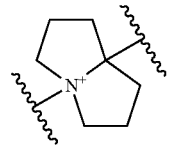
(31)
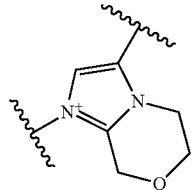
(32)
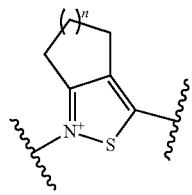
(33)
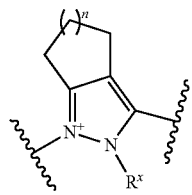
(34)
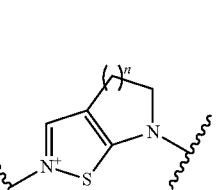
(35)
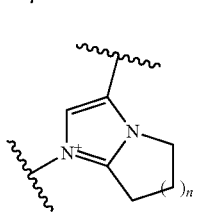
(36)
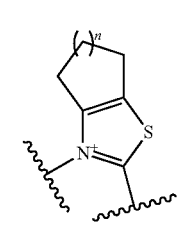
(37)
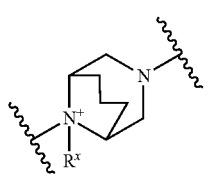
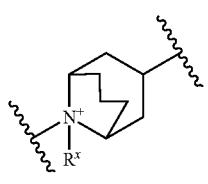

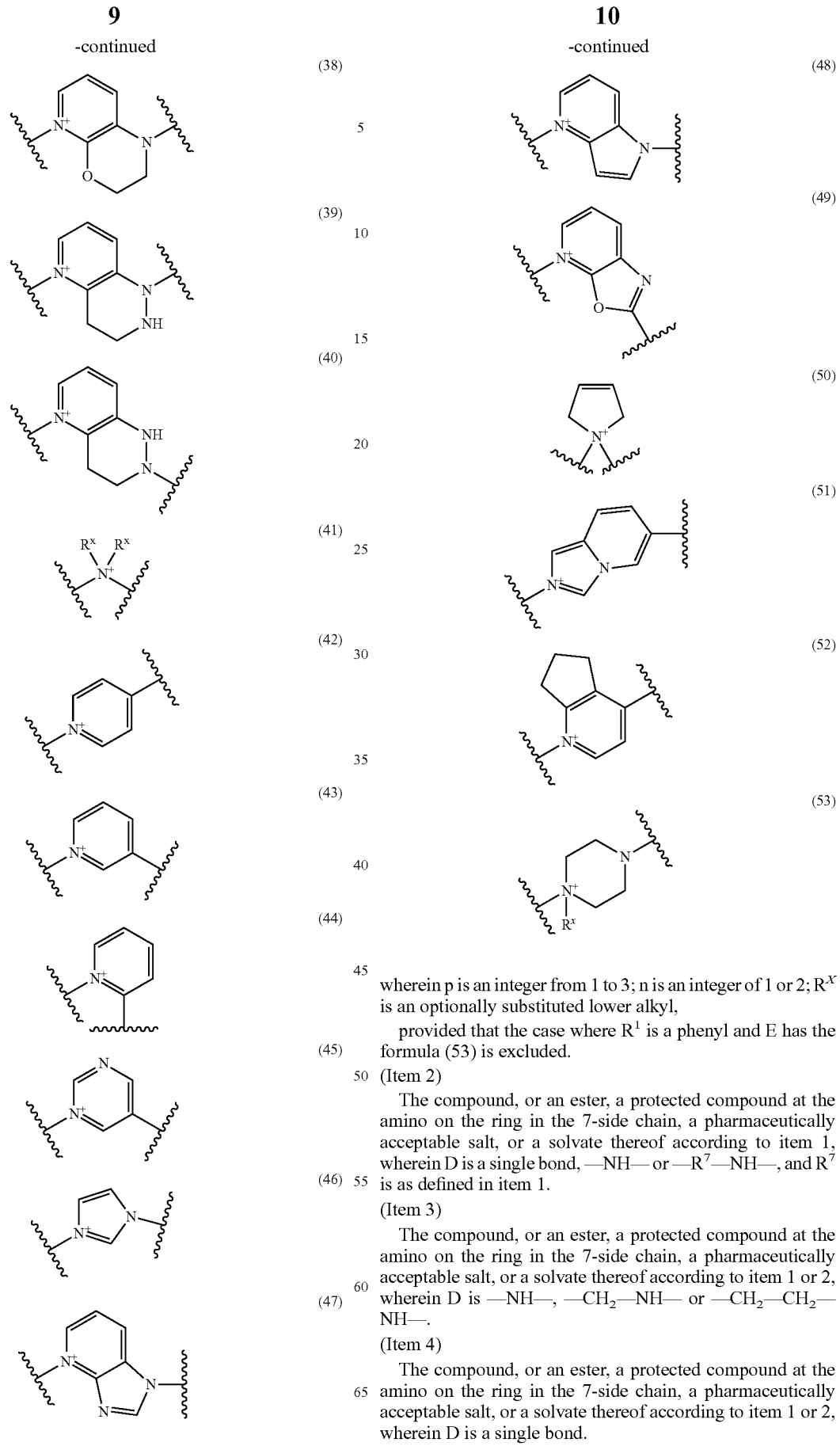

wherein p is an integer from 1 to 3; n is an integer of 1 or 2; $R^x$ is an optionally substituted lower alkyl, provided that the case where $R^1$ is a phenyl and E has the formula (53) is excluded.

(Item 2)

The compound, or an ester, a protected compound at the amino on the ring in the 7-side chain, a pharmaceutically acceptable salt, or a solvate thereof according to item 1, wherein D is a single bond, —NH— or —$R^7$—NH—, and $R^7$ is as defined in item 1.

(Item 3)

The compound, or an ester, a protected compound at the amino on the ring in the 7-side chain, a pharmaceutically acceptable salt, or a solvate thereof according to item 1 or 2, wherein D is —NH—, —CH$_2$—NH— or —CH$_2$—CH$_2$—NH—.

(Item 4)

The compound, or an ester, a protected compound at the amino on the ring in the 7-side chain, a pharmaceutically acceptable salt, or a solvate thereof according to item 1 or 2, wherein D is a single bond.

(Item 5)

The compound, or an ester, a protected compound at the amino on the ring in the 7-side chain, a pharmaceutically acceptable salt, or a solvate thereof according to item 1, wherein D has the formula:

[Formula 5]

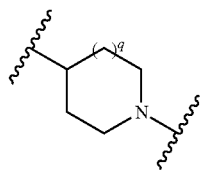

wherein q is as defined in item 1.

(Item 6)

The compound, or an ester, a protected compound at the amino on the ring in the 7-side chain, a pharmaceutically acceptable salt, or a solvate thereof according to any of items 1 to 5, wherein E is selected from the formulae (1) to (9), (11) to (40), (47) to (49), (51) and (52).

(Item 7)

The compound, or an ester, a protected at the amino on the ring in the 7-side chain, a pharmaceutically acceptable salt, or a solvate thereof according to any of items 1 to 5, wherein E is selected from the formulae (5), (6), (9) to (11), (26), (29) to (34), (36), (37) and (50).

(Item 8)

The compound, or an ester, a protected compound at the amino on the ring in the 7-side chain, a pharmaceutically acceptable salt, or a solvate thereof according to any of items 1 to 5, wherein E is selected from the formulae (5), (6), (10) and (11).

(Item 9)

The compound, or an ester, a protected compound at the amino on the ring in the 7-side chain, a pharmaceutically acceptable salt, or a solvate thereof according to any of items 1 to 5, wherein E is selected from the formulae (1) to (4), (7), (8), (12) to (25), (27), (28), (35), (38) to (40), (47) and (48).

(Item 10)

The compound, or an ester, a protected compound at the amino on the ring in the 7-side chain, a pharmaceutically acceptable salt, or a solvate thereof according to any of items 1 to 5, wherein E is selected from the formulae (1) to (3), (7) and (12).

(Item 11)

The compound, or an ester, a protected compound at the amino on the ring in the 7-side chain, a pharmaceutically acceptable salt, or a solvate thereof according to any of items 1 to 10, wherein U is —S—.

(Item 12)

The compound, or an ester, a protected compound at the amino on the ring in the 7-side chain, a pharmaceutically acceptable salt, or a solvate thereof according to any of items 1 to 11, wherein W is —CH$_2$—.

(Item 13)

The compound, or an ester, a protected compound at the amino on the ring in the 7-side chain, a pharmaceutically acceptable salt, or a solvate thereof according to any of items 1 to 12, wherein R$^3$ is a hydrogen atom or —OCH$_3$.

(Item 14)

The compound, or an ester, a protected compound at the amino on the ring in the 7-side chain, a pharmaceutically acceptable salt, or a solvate thereof according to any of items 1 to 13, wherein the formula:

[Formula 6]

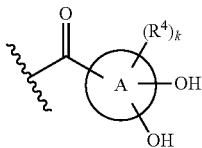

is selected from the following:

[Formula 7]

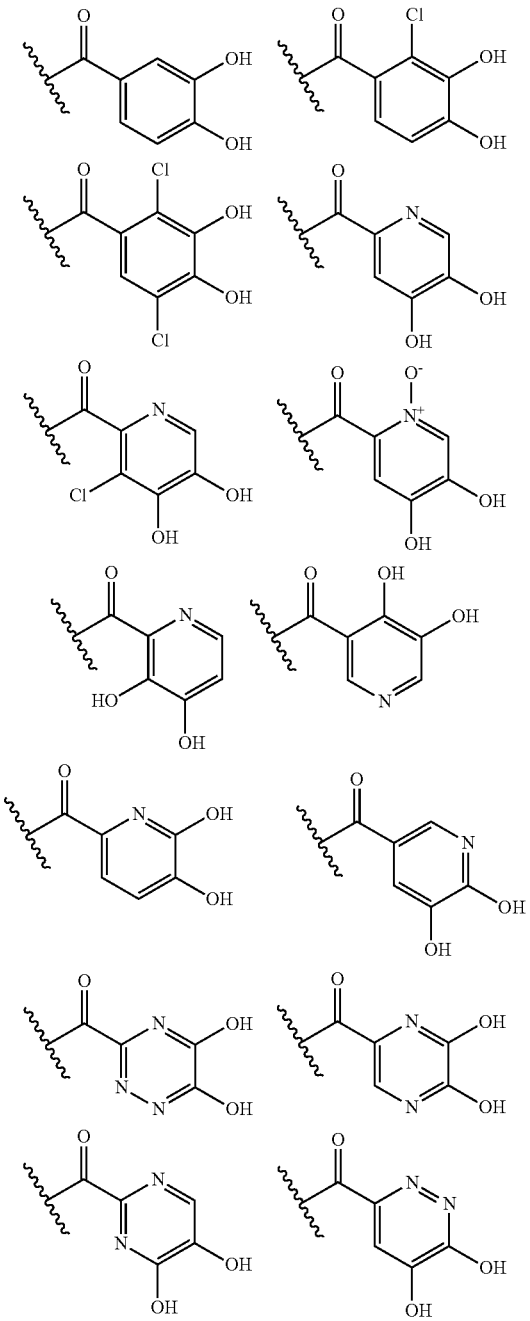

-continued

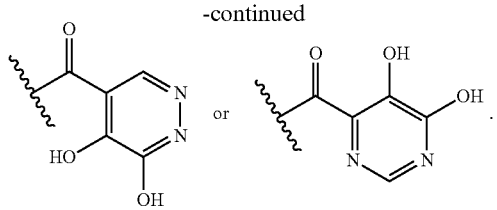

(Item 15)

The compound, or an ester, a protected compound at the amino on the ring in the 7-side chain, a pharmaceutically acceptable salt, or a solvate thereof according to any of items 1 to 13,
wherein the formula:

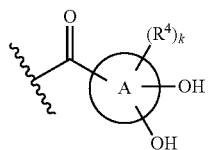
[Formula 8]

is selected from the following:

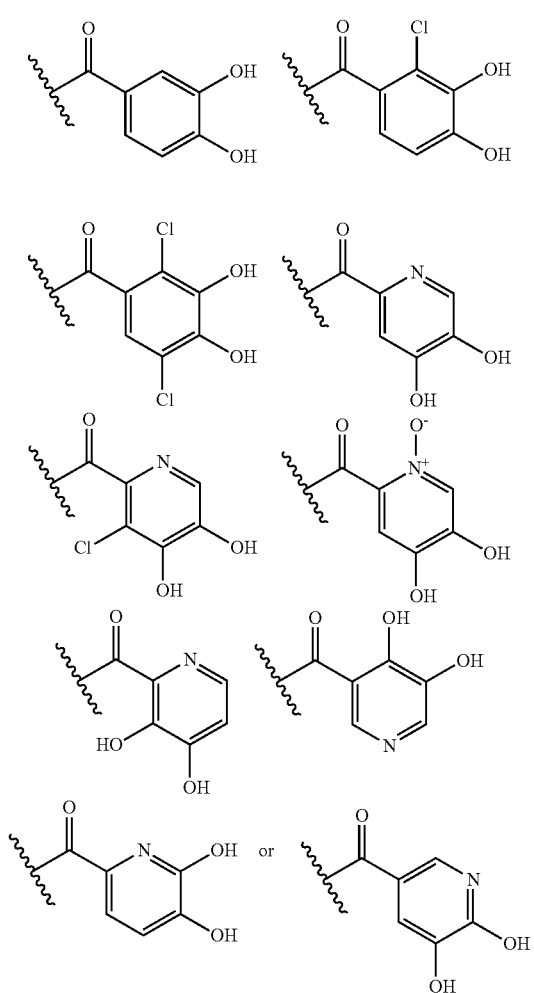
[Formula 9]

(Item 16)

The compound, or an ester, a protected compound at the amino on the ring in the 7-side chain, a pharmaceutically acceptable salt, or a solvate thereof according to any of items 1 to 13,
wherein the formula:

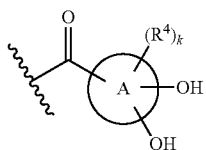
[Formula 10]

is selected from the following:

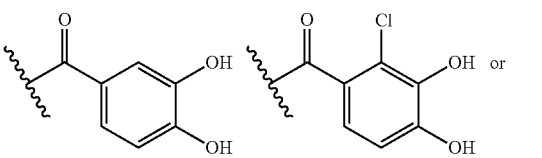
[Formula 11]

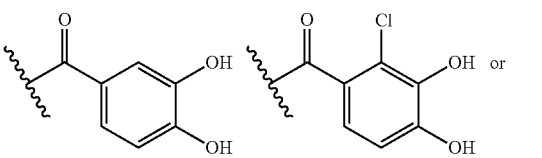

(Item 17)

The compound, or an ester, a protected compound at the amino on the ring in the 7-side chain, a pharmaceutically acceptable salt, or a solvate thereof according to any of items 1 to 16, wherein $R^1$ is an optionally substituted phenyl.

(Item 18)

The compound, or an ester, a protected compound at the amino on the ring in the 7-side chain, a pharmaceutically acceptable salt, or a solvate thereof according to any of items 1 to 17, wherein $R^{24}$ is a hydrogen atom, optionally substituted amino group, —SO$_3$H, optionally substituted aminosulfonyl group, carboxyl group, optionally substituted carbamoyl group, hydroxyl group, or substituted carbonyloxy group.

(Item 19)

The compound, or an ester, a protected compound at the amino on the ring in the 7-side chain, a pharmaceutically acceptable salt, or a solvate thereof according to any of items 1 to 17, wherein $R^{24}$ is selected from a substituted amino group shown below:

[Formula 12]

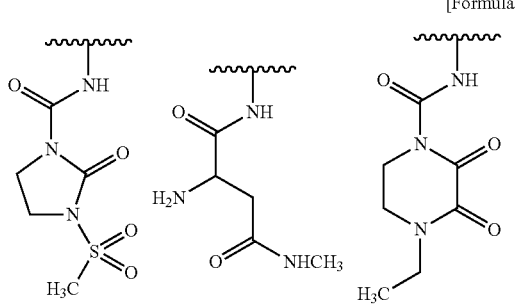

a substituted aminosulfonyl group shown below:

[Formula 13]

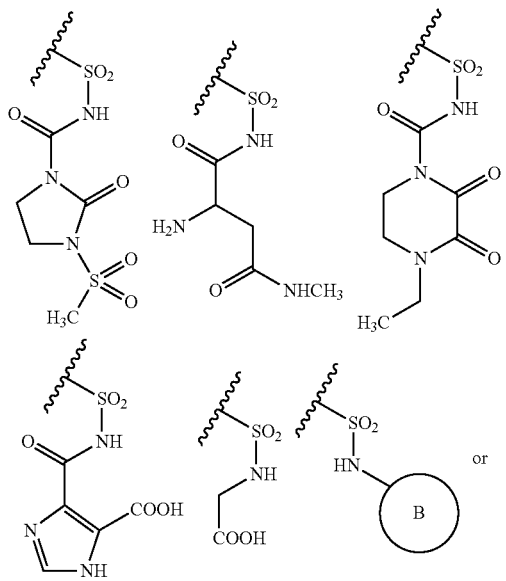

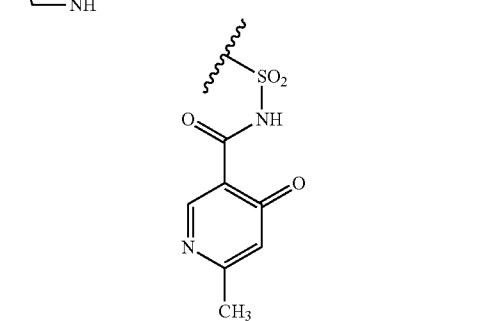

wherein ring B represents an optionally substituted heterocyclic group;

a substituted carbamoyl group shown below:

[Formula 14]

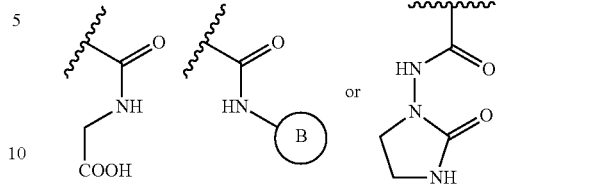

wherein ring B represents an optionally substituted heterocyclic group; or a substituted carbonyloxy group shown below:

[Formula 15]

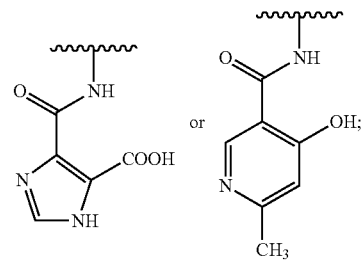

wherein ring B represents an optionally substituted heterocyclic group.

(Item 20)

The compound, or an ester, a protected compound at the amino on the ring in the 7-side chain, a pharmaceutically acceptable salt, or a solvate thereof according to any of items 1 to 17, wherein $R^{24}$ and $R^{23}$ are taken together to form a substituted alkenyl group shown below:

[Formula 16]

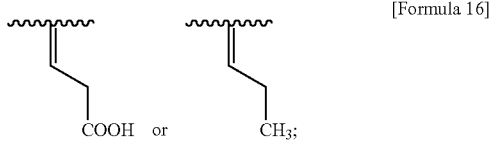

or a substituted oxime group shown below:

[Formula 17]

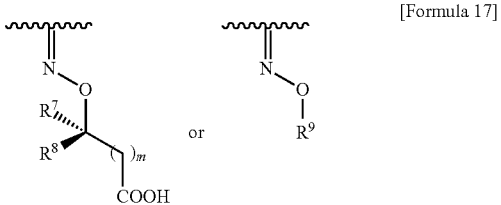

wherein $R^7$ and $R^8$ are each independently a hydrogen atom, halogen, hydroxy, carboxy, optionally substituted lower alkyl, optionally substituted carbocyclic group, or optionally substituted heterocyclic group, or $R^7$ and $R^8$ may be taken together with a neighboring atom to form an optionally substituted carbocyclic group or optionally substituted heterocyclic group;

$R^9$ is an optionally substituted lower alkyl; and m is an integer from 0 to 3.

(Item 21)

A pharmaceutical composition, which comprises a compound, or an ester, a protected compound at the amino on the ring in the 7-side chain, a pharmaceutically acceptable salt, or a solvate thereof according to any of items 1 to 20.

(Item 22)

The pharmaceutical composition according to item 21, which possesses antimicrobial activity.

(Item 23)

A method for treating an infectious disease, characterized in that an amount of the compound according to any of items 1 to 20 effective in exhibiting antimicrobial activity is administered to a human.

(Item 24)

The compound according to any of items 1 to 20, which is used for the prevention or treatment of an infectious disease.

(Item 25)

Use of the compound according to any of items 1 to 20 for manufacturing a medicine for the prevention or treatment of an infectious disease.

Effects of the Invention

The compounds of the subject invention are useful as a pharmaceutical product in that the compounds have at least one of the following features:
1) The compounds exhibit potent antimicrobial spectrum against a variety of bacteria including Gram negative bacteria and/or Gram positive bacteria;
2) the compounds exhibit potent antimicrobial activity against beta-lactamase producing Gram negative bacteria;
3) the compounds exhibit potent antimicrobial activity against multidrug-resistant bacteria, in particular, Class B type metallo-beta-lactamase producing Gram negative bacteria;
4) the compounds exhibit potent antimicrobial activity against extended-spectrum beta-lactamase (ESBL) producing bacteria;
5) the compounds do not exhibit cross resistance with known Cephem drugs and/or Carbapenem drugs; and
6) the compounds do not exhibit side effects such as fever after administration into the body.

EMBODIMENTS FOR CARRYING OUT THE INVENTION

Hereinafter, the subject invention is described with showing embodiments. It should be understood that, throughout the present specification, the expression of a singular form (for example, in the English language, "a", "an", "the", and the like; and in other languages, corresponding articles, adjectives, and the like) includes the concept of its plural form unless specified otherwise. Furthermore, it should be understood that the terms used herein are used in the meaning as generally used in the art unless specified otherwise. Thus, unless defined otherwise, all technical and scientific terms used herein have the same meaning as those generally understood by those skilled in the art in the field to which the subject invention pertains. If there is a contradiction, the present specification (including definitions) precedes. Each specific definition of the terms specifically used herein is described below.

Each term in the present specification is used alone or in combination with another word, and defined as below.

"Halogen" includes fluorine, chlorine, bromine and iodine. Preferably, halogen is fluorine, chlorine or bromine, and more preferably is chlorine.

"Lower alkyl" includes linear or branched alkyl having 1-8 carbons, preferably 1-6 carbons, and more preferably 1-4 carbons, and includes, for example, methyl, ethyl, n-propyl, isopropyl, n-butyl, isobutyl, sec-butyl, tert-butyl, n-pentyl, isopentyl, neopentyl, hexyl, isohexyl, n-heptyl, isoheptyl, n-octyl, and the like.

"Lower alkylene" includes linear alkylene having 1-8 carbons, preferably 1-6 carbons, more preferably 1-4 carbons, and most preferably one or two carbons, and includes, for example, methylene, ethylene, n-propylene, n-butylene, n-pentylene, n-hexylene, and the like.

"Halo(lower)alkyl" refers to a group in which at least one position of said "lower alkyl" is substituted with the above "halogen", and includes, for example, monofluoromethyl, difluoromethyl, trifluoromethyl, monochloromethyl, dichloromethyl, trichloromethyl, monobromomethyl, monofluoroethyl, monochloroethyl, chlorodifluoromethyl, and the like. Preferably, halo(lower)alkyl is trifluoromethyl, or trichloromethyl.

Substituent groups for "optionally substituted amino" or "optionally substituted carbamoyl" include mono- or di-(lower)alkyl, lower alkylcarbonyl, or lower alkylsulfonyl, optionally substituted lower alkyl (e.g., methyl, ethyl, isopropyl, benzyl, carbamoylalkyl (e.g., carbamoylmethyl), mono- or di-(lower)alkylcarbamoyl(lower)alkyl (e.g., dimethylcarbamoylethyl), hydroxy(lower)alkyl, heterocycle(lower)alkyl (e.g., morpholinoethyl, tetrahydropyranylethyl), alkoxycarbonyl(lower)alkyl (e.g., ethoxycarbonylmethyl, ethoxycarbonylethyl), mono- or di-(lower)alkylamino(lower)alkyl (e.g., dimethylaminoethyl)), (lower)alkoxy(lower)alkyl (e.g., methoxyethyl, ethoxymethyl, ethoxyethyl, isopropoxyethyl, and the like), acyl (e.g., formyl, optionally substituted lower alkylcarbonyl (e.g., acetyl, propionyl, butylyl, isobutylyl, valeryl, isovaleryl, pivaloyl, hexanoyl, octanoyl, methoxyethylcarbonyl, 2,2,2-trifluoroethylcarbonyl, ethoxycarbonylmethylcarbonyl), (lower)alkoxy(lower)alkylcarbonyl (e.g., methoxyethylcarbonyl), (lower)alkylcarbamoyl(lower)alkylcarbonyl (e.g., methylcarbamoylethylcarbonyl), alkoxycarbonylacetyl), optionally substituted arylcarbonyl (e.g., benzoyl, toluoyl), optionally substituted aralkyl (e.g., benzyl, 4-fluorobenzyl), hydroxy, optionally substituted lower alkylsulfonyl (e.g., methanesulfonyl, ethanesulfonyl, isopropylsulfonyl, 2,2,2-trifluoroethanesulfonyl, benzylsulfonyl, methoxyethylsulfonyl), arylsulfonyl optionally having a lower alkyl or halogen as a substituent (e.g., benzenesulfonyl, toluenesulfonyl, 4-fluorobenzenesulfonyl), cycloalkyl (e.g., cyclopropyl), aryl optionally having a lower alkyl as a substituent (e.g., phenyl, trityl), lower alkylaminosulfonyl (e.g., methylaminosulfonyl, dimethylaminosulfonyl), lower alkylaminocarbonyl (e.g., dimethylaminocarbonyl), lower alkoxycarbonyl (e.g., ethoxycarbonyl), cycloalkylcarbonyl (e.g., cyclopropylcarbonyl, cyclohexylcarbonyl), optionally substituted sulfamoyl (e.g., sulfamoyl, methylsulfamoyl, dimethylsulfamoyl), lower alkylcarbonylamino (e.g., methylcarbonylamino), heterocycle (e.g., morpholino, tetrahydropyranyl), optionally substituted amino (e.g., mono- or di-alkylamino (e.g., dimethylamino), formylamino), and the like.

"Alkenyl" refers to a linear or branched alkenyl having 2 to 8 carbons and having one or more double bonds on said "lower alkyl". Examples thereof include vinyl, 1-propenyl, 2-propenyl, 1-butenyl, 2-butenyl, 3-butenyl, 1,3-butadienyl, 3-methyl-2-butenyl, and the like. Preferred is lower alkenyl, which is alkenyl having 2 to 6 carbons, more preferably 2 to 4 carbons.

With regard to an amino group of an "optionally substituted amino" or "optionally substituted carbamoyl", two substituents of the amino group may be taken together with the adjacent nitrogen atom to form a nitrogen-containing heterocycle which optionally includes a sulfur atom and/or an oxygen atom in the ring (preferably, the heterocycle is a 5- to 7-membered ring, and is preferably saturated). The heterocycle is optionally substituted with oxo or hydroxy. A sulfur atom forming the heterocycle may have oxo as a substituent. Preferred are a 5- or 6-membered ring (e.g., piperazinyl, piperidino, morpholino, pyrrolidino, 2-oxopiperidino, 2-oxopyrrolidino, 4-hydroxymorpholino, and the like), and the like.

Substituent groups for "optionally substituted lower alkyl" include at least one group selected from Substituent Group Alpha. When substitution is carried out with a plurality of Substituent Group Alpha, the plurality of Substituent Group Alpha may be the same or different.

Substituent groups for "optionally substituted lower alkylene" include optionally substituted lower alkyl, and at least one group selected from Substituent Group Alpha. When substitution is carried out with a plurality of substituents, the substituents may be the same or different.

Substituent groups for "optionally substituted aminosulfonyl" include an optionally substituted lower alkyl, and at least one group selected from Substituent Group Alpha.

Substituent groups for "optionally substituted lower alkyloxycarbonyl" include an optionally substituted lower alkyl, and at least one group selected from Substituent Group Alpha.

Substituents groups for "substituted carbonyloxy" include an optionally substituted lower alkyl, an amino having a heterocyclic group as a substituent, and at least one group selected from Substituent Group Alpha.

Substituent groups for "optionally substituted oxime" include an optionally substituted (with carboxyl or the like in particular) lower alkyl (methyl, ethyl, isopropyl, or the like), an amino having a heterocyclic group as a substituent, and at least one group selected from Substituent Group Alpha.

Substituent groups for "optionally substituted quaternary ammonium group" include an optionally substituted lower alkyl, at least one group selected from Substituent Group Alpha, or two or more substituents that are taken together to form a carbocyclic group or heterocyclic group.

Here, "Substituent Group Alpha" is a group consisting of halogen, hydroxy, lower alkoxy, hydroxy(lower)alkoxy, (lower)alkoxy(lower)alkoxy, carboxy, amino, acylamino, lower alkylamino, imino, hydroxyimino, lower alkoxyimino, lower alkylthio, carbamoyl, lower alkylcarbamoyl, hydroxy(lower)alkylcarbamoyl, sulfamoyl, lower alkylsulfamoyl, lower alkylsulfinyl, cyano, nitro, a carbocyclic group, and a heterocyclic group.

The lower alkyl moiety in "lower alkoxy", "hydroxy(lower)alkoxy", "(lower)alkoxy(lower)alkoxy", "lower alkylamino", "lower alkoxyimino", "lower alkylthio", "lower alkylcarbamoyl", "hydroxy(lower)alkylcarbamoyl", and "lower alkylsulfamoyl" and "lower alkylsulfinyl" is defined the same as the above "lower alkyl".

Preferred embodiments of substituents in an "optionally substituted lower alkyl" include a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

Preferred embodiments of "optionally substituted lower alkyl" include methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, phenethyl, 4-hydroxybenzyl, 4-methoxybenzyl, 4-carboxybenzyl, and the like.

"Carbocyclic group" includes cycloalkyl, cycloalkenyl, aryl and non-aromatic fused carbocyclic groups, and the like.

"Cycloalkyl" is a carbocyclic group having 3-10 carbons, preferably 3-8 carbons, more preferably 4-8 carbons, and includes, for example, cyclopropyl, cyclobutyl, cyclopentyl, cyclohexyl, cycloheptyl, cyclooctyl, cyclononyl, cyclodecyl, and the like.

"Cycloalkenyl" includes those in which the ring of the cycloalkyl has at least one double bond at any position(s), and specifically includes, for example, cyclopropenyl, cyclobutenyl, cyclopentenyl, cyclohexenyl, cycloheptynyl, cyclooctynyl, and cyclohexadienyl, and the like.

"Aryl" includes phenyl, naphthyl, anthryl, phenanthryl, and the like, and in particular, phenyl is preferable.

"Non-aromatic fused carbocyclic group" includes a group in which two or more cyclic groups selected from the "cycloalkyl", "cycloalkenyl," and "aryl" are fused, and specifically includes, for example, indanyl, indenyl, tetrahydronaphthyl, and fluorenyl, and the like.

"Heterocyclic group" includes heterocyclic groups having at least one hetero atom selected from O, S, and N, in the ring thereof, and specifically includes, for example, 5- or 6-membered heteroaryl such as pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, triazolyl, thiadiazolyl, furyl, thienyl, and the like; bicyclic fused heterocyclic groups such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzotriazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, pyrazolopyridine, triazolopyridyl, imidazothiazolyl, pyrazinopyridazinyl, quinazolinyl, quinolyl, isoquinolyl, naphthyridinyl, dihydrobenzofuryl, tetrahydroquinolyl, tetrahydroisoquinolyl, dihydrobenzoxazine, tetrahydrobenzothienyl, and the like; tricyclic fused heterocyclic groups such as carbazolyl, acridinyl, xanthenyl, phenothiadinyl, phenoxathiinyl, phenoxazinyl, dibenzofuryl, imidazoquinolyl, and the like; non-aromatic heterocyclic groups such as dioxanyl, thiiranyl, oxiranyl, oxathiolanyl, azetidinyl, thianyl, thiazolidine, pyrrolidinyl, pyrrolinyl, imidazolidinyl, imidazolinyl, pyrazolidinyl, pyrazolinyl, piperidyl, piperazinyl, morpholinyl, thiomorpholinyl, thiomorpholino, dihydropyridyl, dihyrobenzimidazolyl, tetrahydropyridyl, tetrahydrofuryl, tetrahydropyranyl, tetrahydrothiazolyl, tetrahydroisothiazolyl, dihydrooxazinyl, hexahydroazepinyl, tetrahydrodiazepinyl, and the like. Preferably, heterocyclic group is a 5- or 6-membered heteroaryl or non-aromatic heterocyclic group, and more preferably, a 5- or 6-membered heteroaryl.

Substituents of an "optionally substituted carbocyclic group" and an "optionally substituted heterocyclic group" include optionally substituted lower alkyl, and at least one group selected from Substituent Group Alpha.

Preferred embodiments of substituents in an "optionally substituted carbocyclic group" and an "optionally substituted heterocyclic group" include methyl, ethyl-isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like.

"6-membered aromatic heterocyclic group having 1-3 nitrogen atoms" includes pyridine, pyrimidine, pyridazine, pyrazine, 1,3,5-triazine, 1,2,4-triazine, 1,2,3-triazine, and the like.

Examples of an "optionally substituted carbocyclic group or optionally substituted heterocyclic group" of $R^1$ include phenyl and hydroxyphenyl; phenyl and hydroxyphenyl which have a halogen as a substituent group; aminothiazole; aminothiazole which have a halogen as a substituent group; aminothiadiazole; thiophene; furan; benzothiazole; pyridine; pyrimidine; pyridazine; aminopyridine; and the like.

$R^{2A}$ and $R^{2B}$ are defined as below.

a) $R^{2A}$ is a hydrogen atom, optionally substituted amino group, —$SO_3H$, optionally substituted aminosulfonyl group, carboxyl group, optionally substituted lower alkyloxycarbonyl group, optionally substituted carbamoyl group, hydroxyl group, or substituted carbonyloxy group, and $R^{2B}$ is a hydrogen atom, or b) $R^{2A}$ and $R^{2B}$ are taken together to form an optionally substituted alkenyl group, or optionally substituted oxime group, provided that when $R^1$ is an aminothiazole of which the amino group may be protected, or an aminothiadiazole of which the amino group may be protected, $R^{2A}$ and $R^{2B}$ are not taken together to form an optionally substituted oxime group.

Furthermore, examples of $R^{2A}$ include a hydrogen atom, optionally substituted amino group, —$SO_3H$, optionally substituted aminosulfonyl group, carboxyl group, optionally substituted carbamoyl group, hydroxyl group, or substituted carbonyloxy group. Examples thereof include a substituted amino group shown below:

[Formula 18]

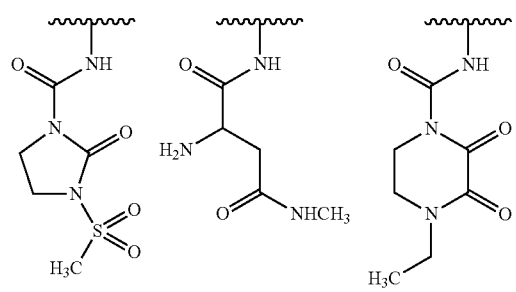

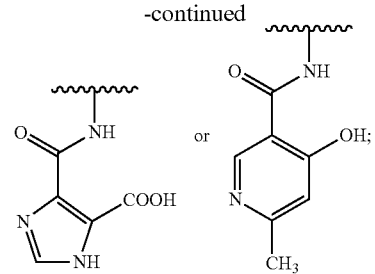

a substituted aminosulfonyl group shown below:

[Formula 19]

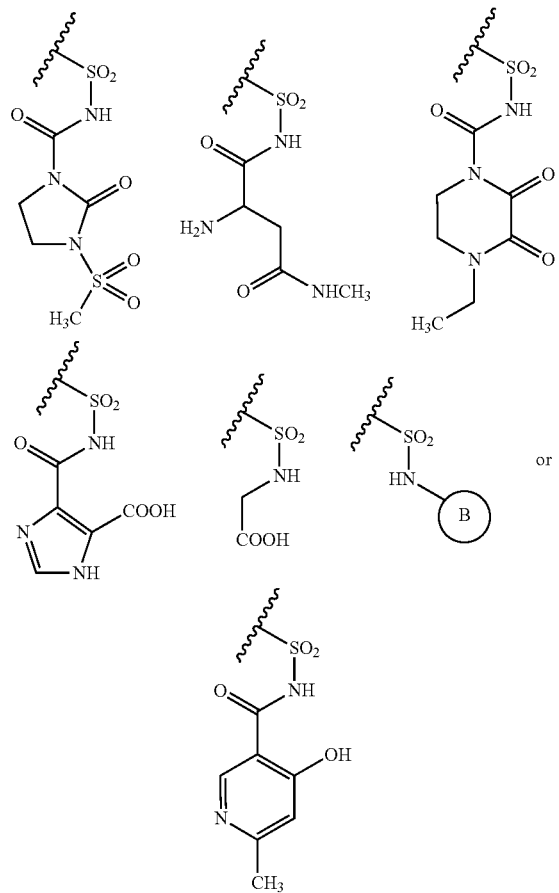

wherein ring B represents an optionally substituted heterocyclic group;

a substituted carbamoyl group shown below:

[Formula 20]

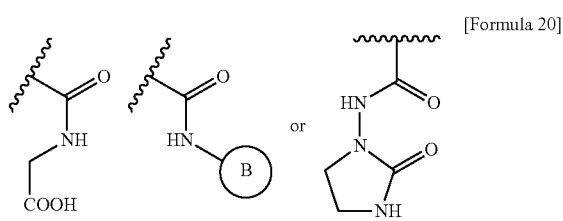

wherein ring B represents an optionally substituted heterocyclic group; or
a substituted carbonyloxy group shown below:

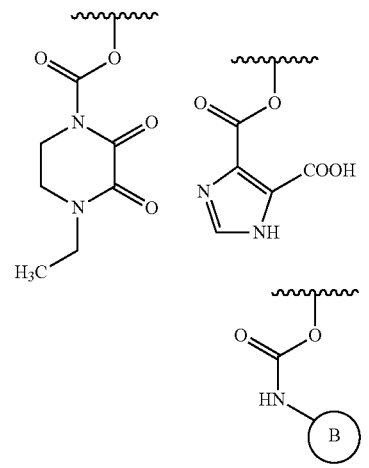

[Formula 21]

wherein ring B represents an optionally substituted heterocyclic group; or
$R^{2A}$ and $R^{2B}$ are taken together to form a substituted alkenyl group of the formula:

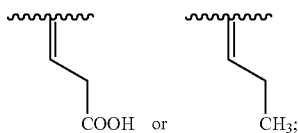

[Formula 22]

or
a substituted oxime group shown below:

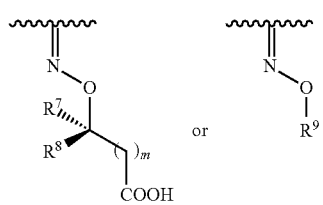

[Formula 23]

wherein
$R^7$ and $R^8$ are each independently a hydrogen atom, halogen, hydroxy, carboxy, optionally substituted lower alkyl, optionally substituted carbocyclic group, or optionally substituted heterocyclic group; or
$R^7$ and $R^8$ may be taken together with a neighboring atom to form an optionally substituted carbocyclic group or optionally substituted heterocyclic group;
$R^9$ is an optionally substituted lower alkyl;
m is an integer from 0 to 3.

Examples in which "$R^7$ and $R^8$ are taken together with a neighboring atom to form an optionally substituted carbocyclic group or optionally substituted heterocyclic group" include cases where $R^7$ and $R^8$ in the formula:

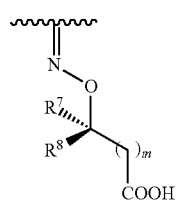

[Formula 24]

wherein each symbol is as defined in item 20, form a cycloalkyl, cycloalkenyl or non-aromatic heterocyclic group which optionally has a group selected from Substituent Group Alpha on the ring. Examples thereof include groups of the following formulae:

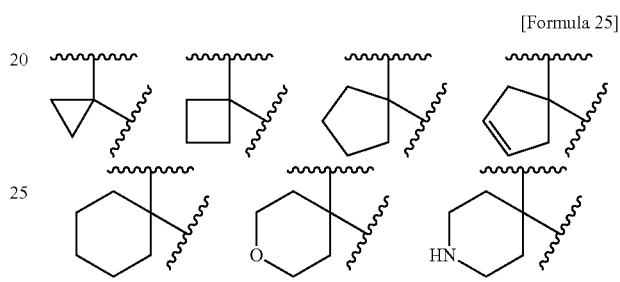

[Formula 25]

which optionally has a group selected from Substituent Group Alpha on the ring.

In the moiety E, "optionally substituted cyclic group selected from either formulae (1) to (40) or (42) to (53)" includes groups in which a hydrogen atom on a carbon atom of each cyclic group is substituted with one or more groups which are the same or different and are selected from optionally substituted lower alkyl or Substituent Group Alpha. Preferred embodiments of the substituents include methyl, ethyl, isopropyl, tert-butyl, a fluorine atom, a chlorine atom, a bromine atom, hydroxy, carboxy, methoxy, ethoxy, hydroxymethoxy, hydroxyethoxy, methoxymethoxy, methoxyethoxy, amino, acetylamino, methylamino, dimethylamino, imino, hydroxyimino, methoxyimino, methylthio, carbamoyl, methylcarbamoyl, hydroxymethylcarbamoyl, sulfamoyl, methylsulfamoyl, lower alkylsulfamoyl, cyano, nitro, phenyl, cyclopropyl, cyclobutyl, cyclohexyl, pyridyl, morpholinyl, and the like. More preferred embodiment is non-substitution.

Examples or embodiments of each site of Formula (I) are shown hereinafter. However, the scope of the subject invention is not limited to those described below.

In a preferred embodiment, "W" is —$CH_2$—, and "U" is —$CH_2$—, —S—, or —O—. More preferably, "W" is —$CH_2$—, and "U" is —S— or —O—. Still more preferably, "W" is —$CH_2$—, and "U" is —S—.

Examples of "$R^7$ and $R^8$" includes a hydrogen atom, a fluorine atom, a chlorine atom, hydroxy, carboxy, methyl, ethyl, isopropyl, tert-butyl, monofluoromethyl, difluoromethyl, trifluoromethyl, carboxymethyl, carboxyethyl, carbamoylmethyl, carbamoylethyl, hydroxymethyl, hydroxyethyl, methoxymethyl, ethoxymethyl, methoxyethyl, ethoxyethyl, methylthiomethyl, ethylthiomethyl, benzyl, 4-hydroxybenzyl, 4-methoxybenzyl, 4-carboxybenzyl, phenyl, naphthyl, cyclopropyl, cyclobutyl, cyclopentyl, cyclohexyl, pyrrolyl, imidazolyl, pyrazolyl, pyridyl, pyridazinyl, pyrimidinyl, pyrazinyl, triazolyl, triazinyl, tetrazolyl, isoxazolyl, oxazolyl, oxadiazolyl, isothiazolyl, triazolyl, thiadiazolyl, furyl, thienyl, and the like.

Preferred combinations of $R^7$ and $R^8$ include, as ($R^7$, $R^8$), (a hydrogen atom, a hydrogen atom), (methyl, a hydrogen atom), (a hydrogen atom, methyl), (methyl, methyl), (ethyl, a hydrogen atom), (a hydrogen atom, ethyl), (ethyl, ethyl), (phenyl, a hydrogen atom), (a hydrogen atom, phenyl), (carboxymethyl, a hydrogen atom), (a hydrogen atom, carboxymethyl), (carboxyethyl, a hydrogen atom), (a hydrogen atom, carboxyethyl), (hydroxyethyl, a hydrogen atom), (a hydrogen atom, hydroxylethyl), (carbamoylmethyl, a hydrogen atom), (a hydrogen atom, carbamoylmethyl), (trifluoromethyl, a hydrogen atom), (carboxy, a hydrogen atom), (carbamoylethyl, a hydrogen atom), (benzyl, a hydrogen atom), (4-hydroxybenzyl, a hydrogen atom), and the like.

Preferred embodiments in cases that "$R^7$ and $R^8$ are taken together with a neighboring atom to form an optionally substituted carbocyclic group, or optionally substituted heterocyclic group" include 3-8 membered cycloalkyl, 3-8 membered cycloalkenyl, or 3-8 membered non-aromatic heterocyclic groups. More preferred embodiments include cases where $R^7$ and $R^8$ in the formula:

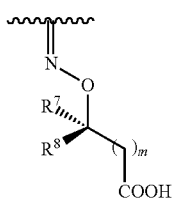

[Formula 26]

wherein each symbol is as defined in item 20, form any one of the following formulae:

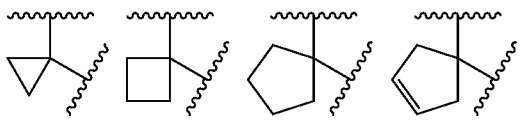

[Formula 27]

"$R^3$" is preferably a hydrogen atom or —$OCH_3$, and more preferably a hydrogen atom. Examples of "$R^4$" include a hydrogen atom, a chlorine atom, a fluorine atom, a bromine atom, cyano, hydroxy, acetyl, methoxy, ethoxy, trifluoromethyl, and the like. Preferably, $R^4$ is a hydrogen atom, hydroxy, or a chlorine atom.

In the present specification, with regard to D and E, a) D is a single bond, —$N(R^8)$—, or —$R^7$—$N(R^8)$—; $R^7$ is an optionally substituted lower alkylene; $R^8$ is a hydrogen or lower alkyl; and E is a quaternary ammonium group selected from the formulae (1) to (40) and (42) to (53) in item 1, which optionally has a substituent group; or b) D has the formula:

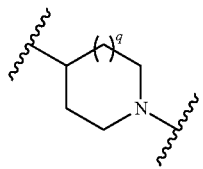

[Formula 28]

wherein q is an integer of 0 or 1; and E is a quaternary ammonium group represented by formula (10) or (41) in item 1.

Examples of "-E-D-(C=O)—" include the following formulae (1A) to (53A):

[Formula 29]

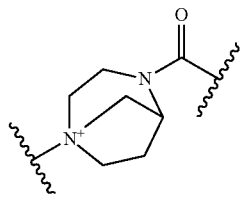
(1A)

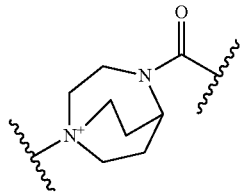
(2A)

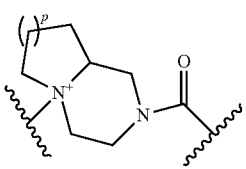
(3A)

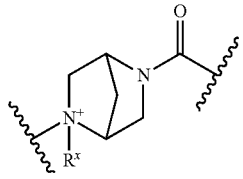
(4A)

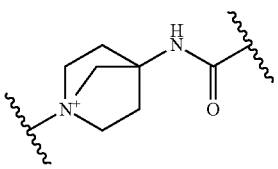
(5A)

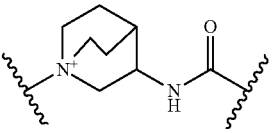
(6A)

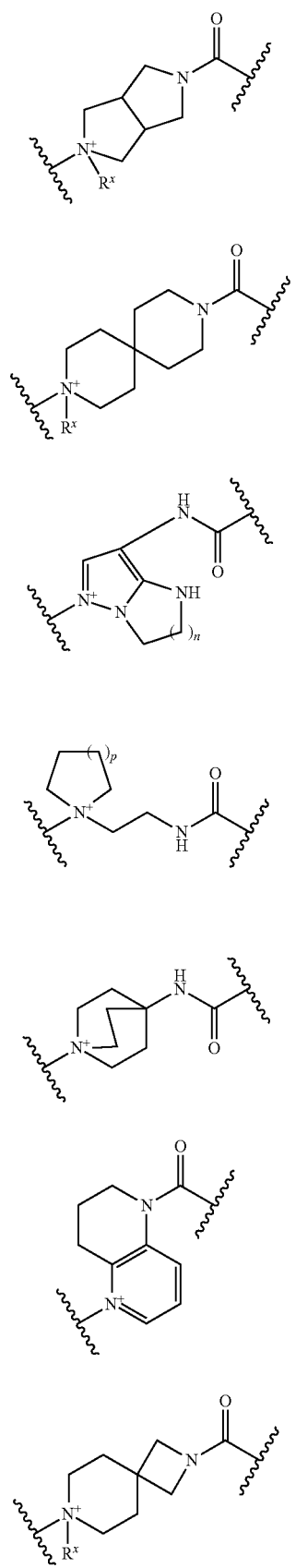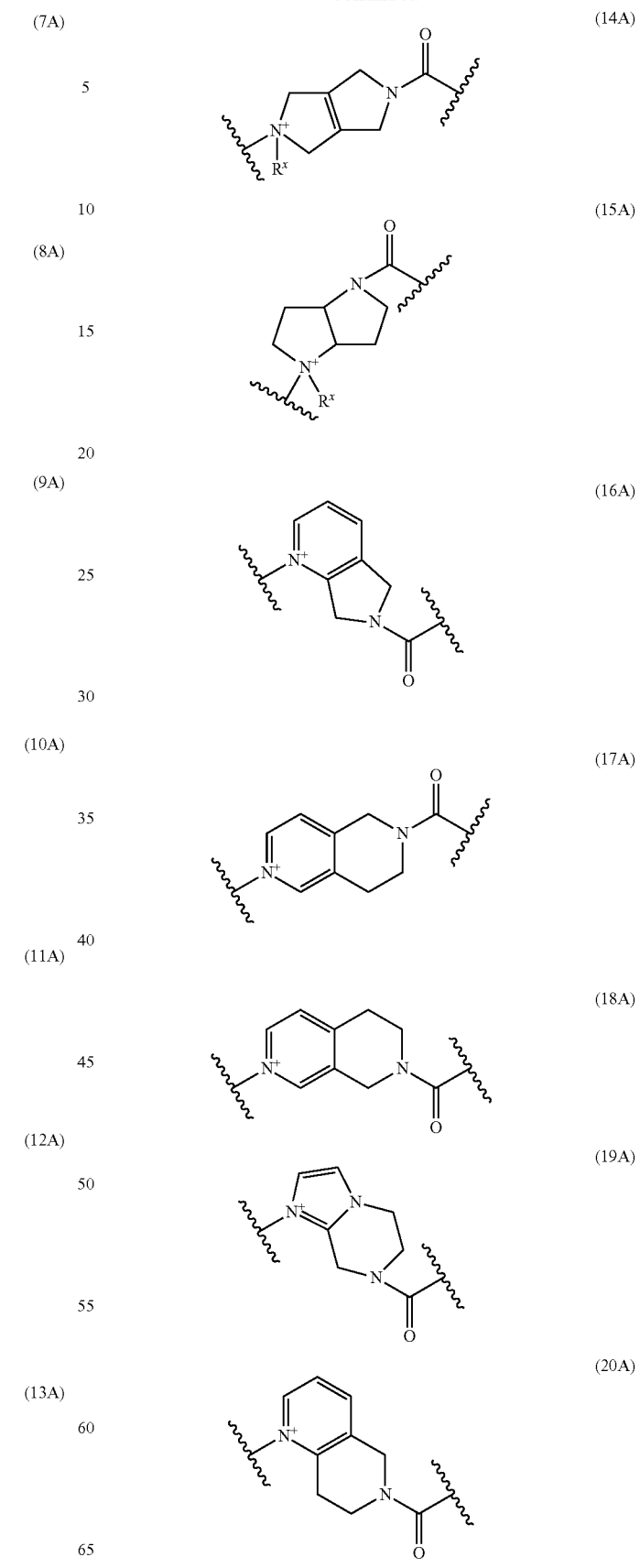

[Formula 30]
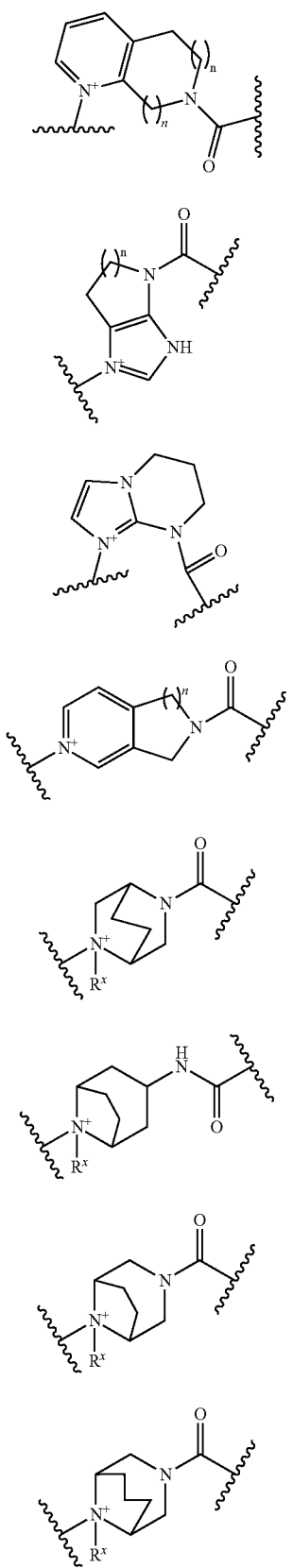
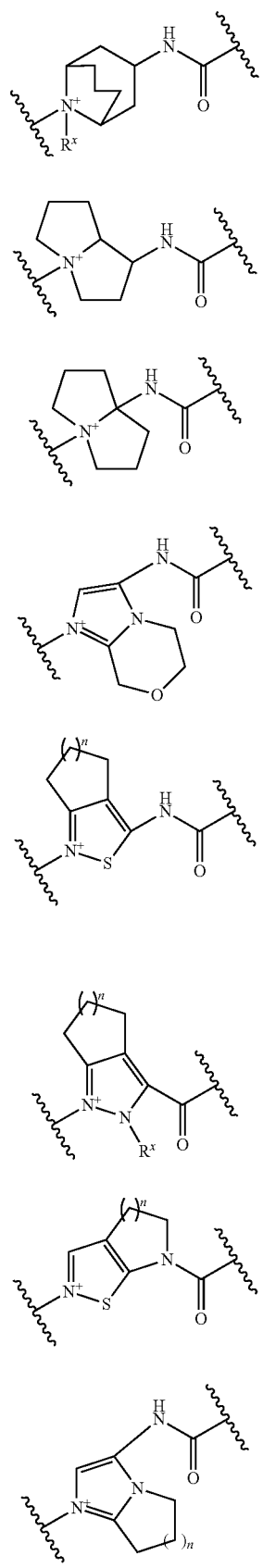

-continued
(37A) 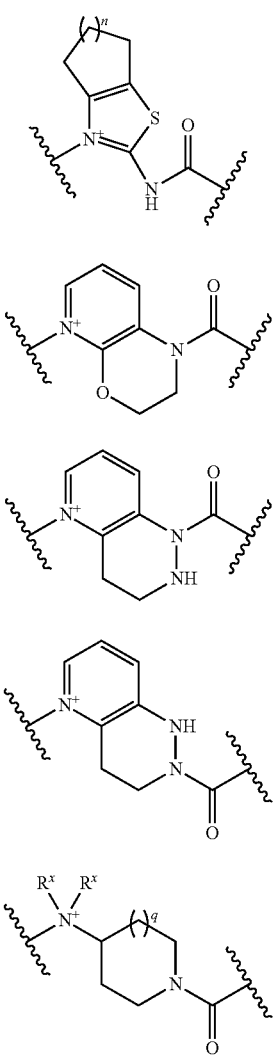
(38A)
(39A)
(40A)
(41A)
[Formula 31]
(42A) 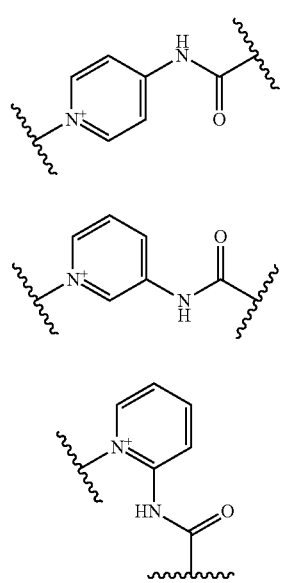
(43A)
(44A)
-continued
(45A) 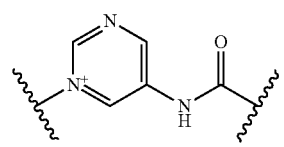
(46A) 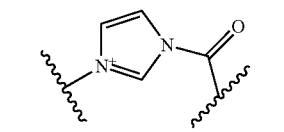
(47A) 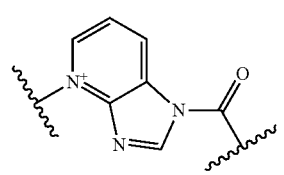
(48A) 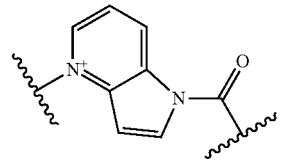
(49A) 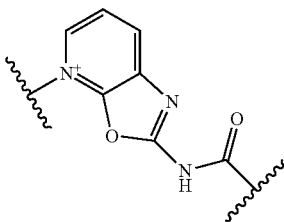
(50A) 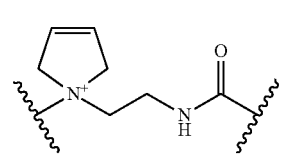
(51A) 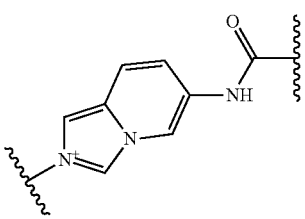
(52A) 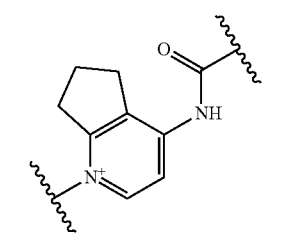

-continued (53A)
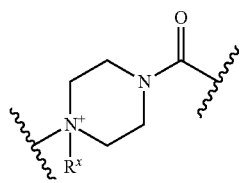

wherein the left side of attachment binds to methylene and the right side of attachment binds to ring A, p is an integer from 1 to 3; n is an integer of 1 or 2; and $R^X$ is an optionally substituted lower alkyl. Preferred examples of $R^X$ include methyl, ethyl, trifluoromethyl, carboxymethyl, carbamoylmethyl, hydroxyethyl, and the like.

Preferred embodiments of "-E-D-(C=O)—" have the following formulae (1B) to (53B):

[Formula 32]

(1B)
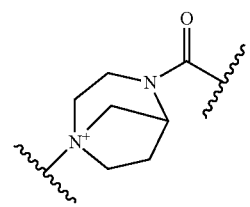

(2B)
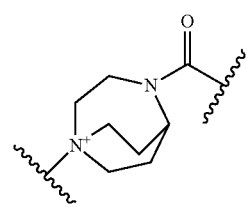

(3B)
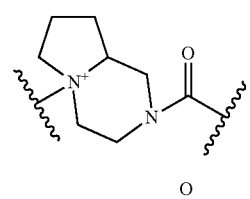

(4B)
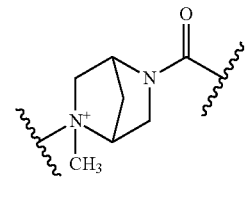

(5B)
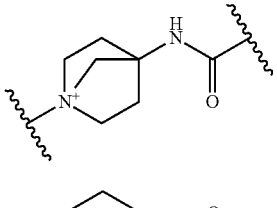

(6B)
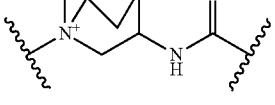

-continued (7B)
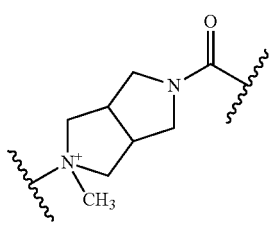

(8B)
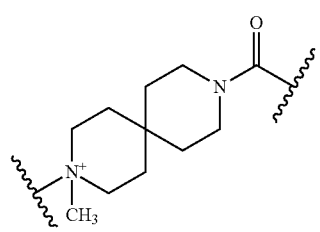

(9B)
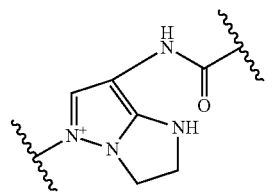

(10B)
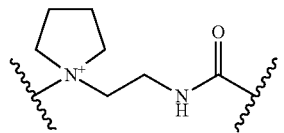

(11B)
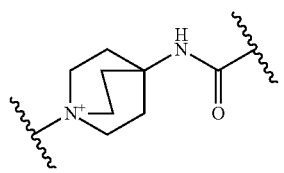

(12B)
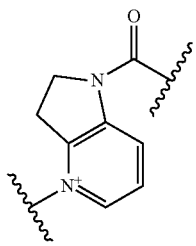

(13B)
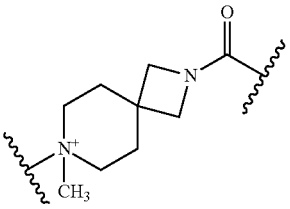

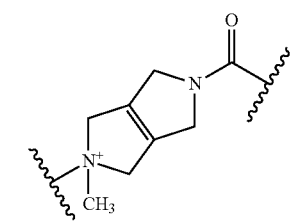 (14B)
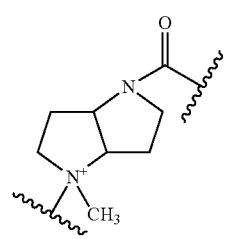 (15B)
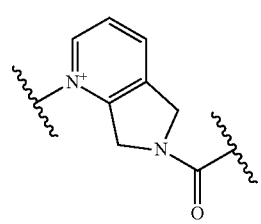 (16B)
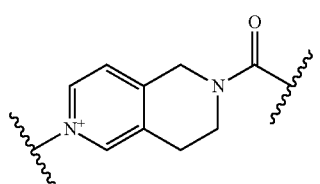 (17B)
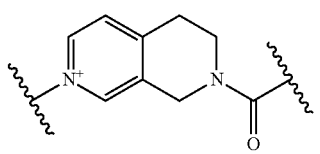 (18B)
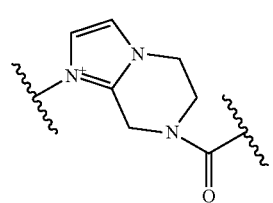 (19B)
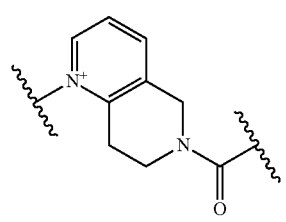 (20B)
[Formula 33]
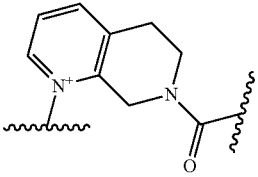 (21B)
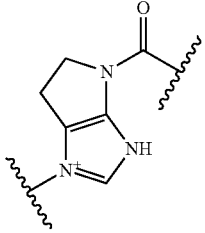 (22B)
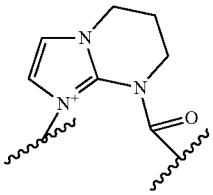 (23B)
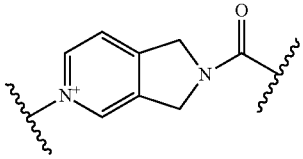 (24B)
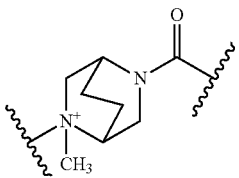 (25B)
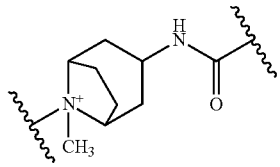 (26B)
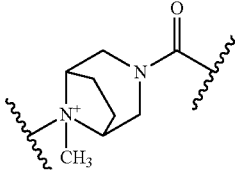 (27B)
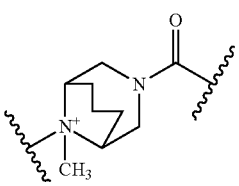 (28B)

-continued
(29B) 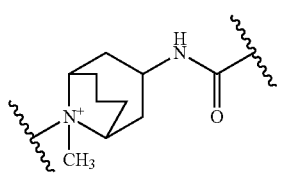
(30B) 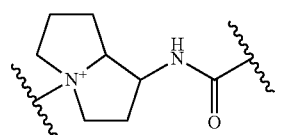
(31B) 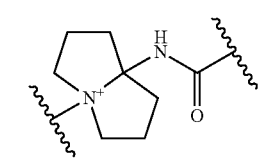
(32B) 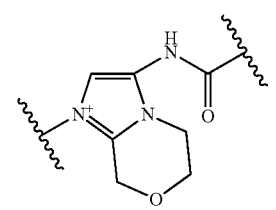
(33B) 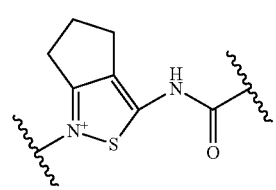
(34B) 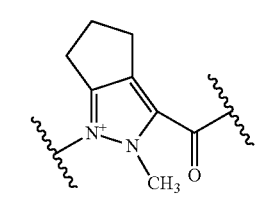
(35B) 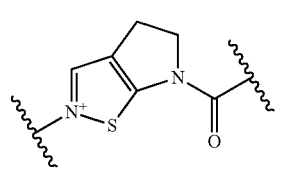
(36B) 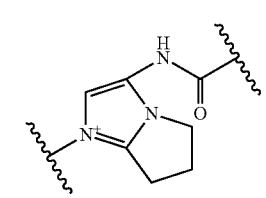
-continued
(37B) 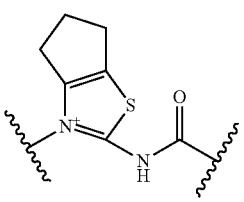
(38B) 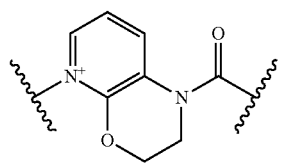
(39B) 
(40B) 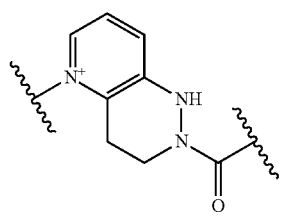
(41B) 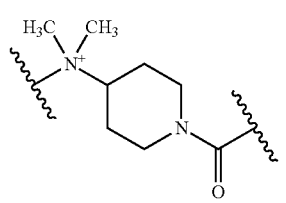
[Formula 34]
(42B) 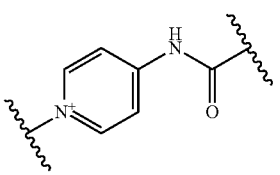
(43B) 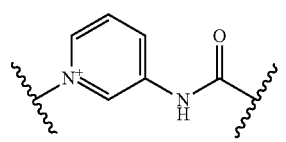
(44B) 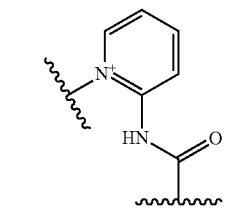

(45B)
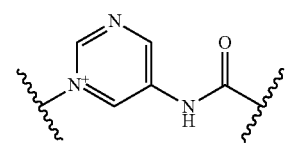
(46B)
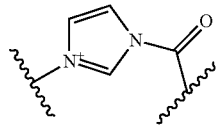
(47B)
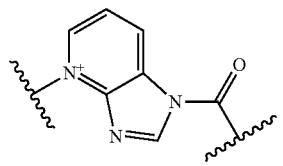
(48B)
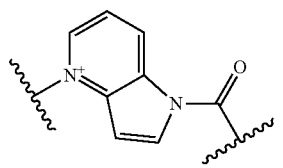
(49B)
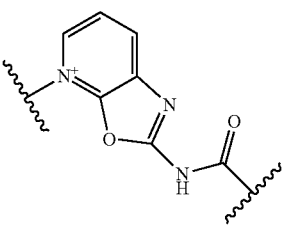
(50B)
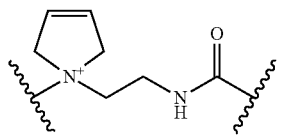
(51B)
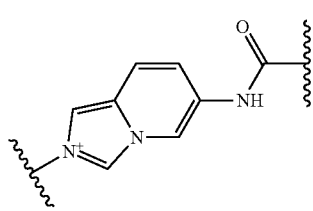
(52B)
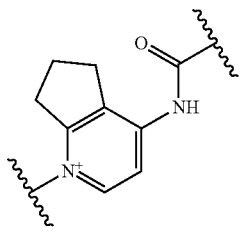
(53B)
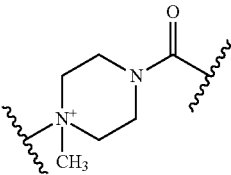
wherein the left side of attachment binds to methylene and the right side of attachment binds to ring A.
Still more preferred embodiments of "-E-D-(C=O)—" have the following formulae:
[Formula 35]
(1B)
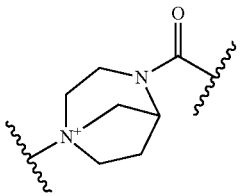
(2B)
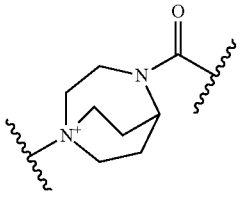
(3B)
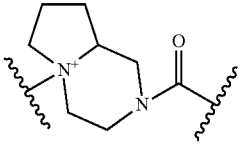
(4B)
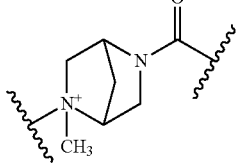
(7B)
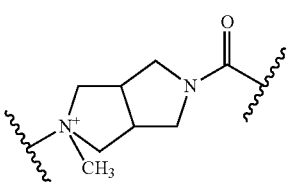
(12B)
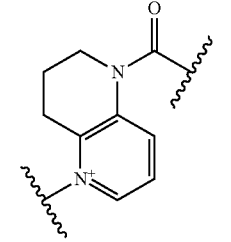

-continued

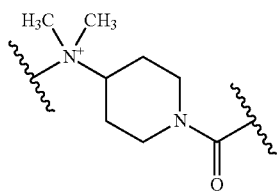
(41B)

wherein the left side of attachment binds to methylene and the right side of attachment binds to ring A.

It is also preferable that E has a formula selected from the following formulae:

[Formula 36]

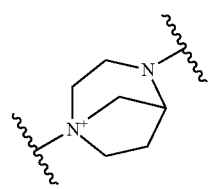
(1)

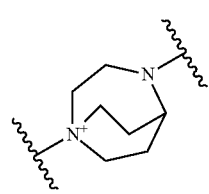
(2)

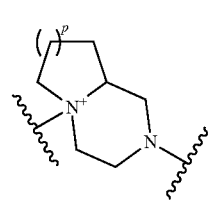
(3)

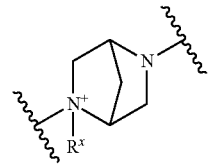
(4)

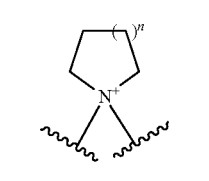
(10)

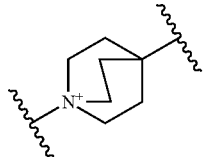
(11)

wherein each symbol is as defined in item 1.

A preferred embodiment of Ring A of the formula:

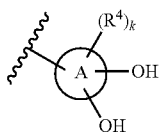
[Formula 37]

wherein each symbol is as defined in item 1, is a 6-membered aromatic heterocyclic group having 1-3 nitrogen atoms.

A preferred embodiment of $R^4$ is a hydrogen atom, chlorine atom or hydroxy.

It is preferable that k is 0 or 1.

More preferred embodiment of the formula:

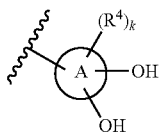
[Formula 38]

wherein each symbol is as defined in item 1, has the formula:

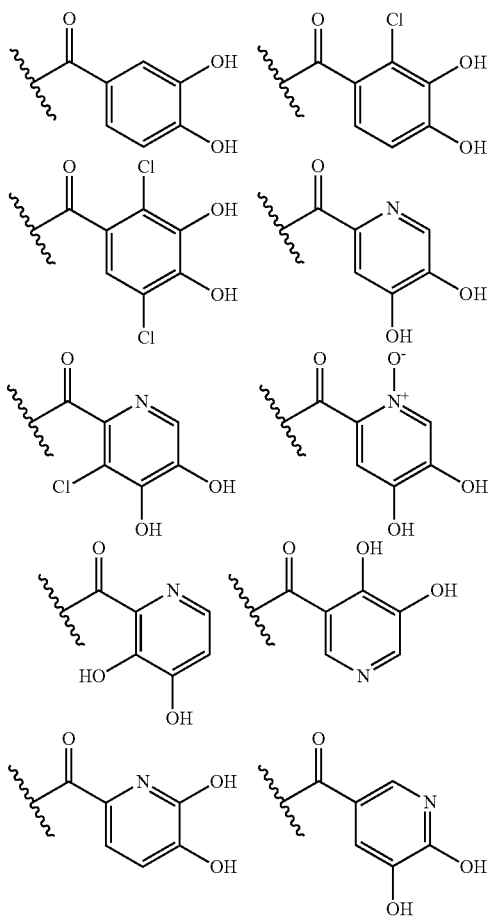
[Formula 39]

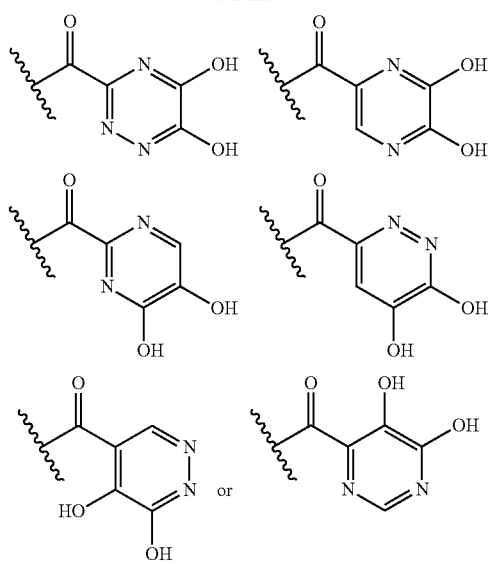

Still more preferred embodiment of the formula:

[Formula 40]

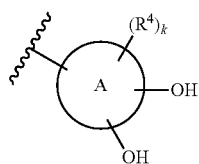

wherein each symbol is as defined in item 1,
has the formula:

[Formula 41]

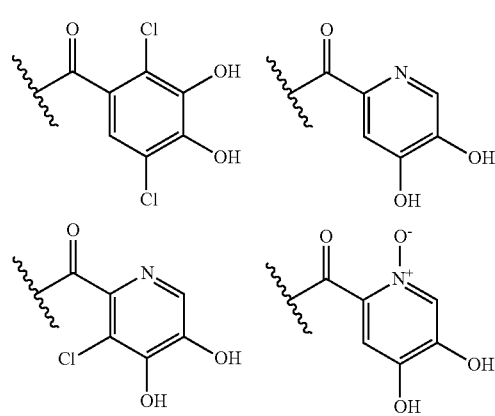

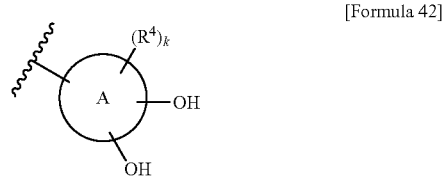

Most preferred embodiment of the formula:

[Formula 42]

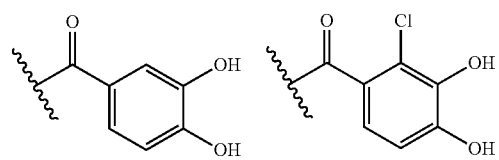

wherein each symbol is as defined in item 1,
has the formula:

[Formula 43]

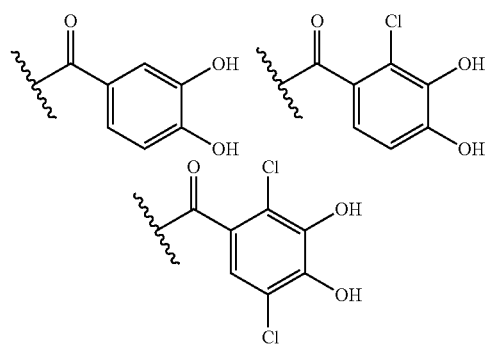

The nomenclature of the substitution position on the Cephem skeleton of Formula (I) is as follows. As used herein, 7-side chain and 3-side chain refer to groups binding to the 7-position and the 3-position of the Cephem skeleton as shown below, respectively.

[Formula 44]

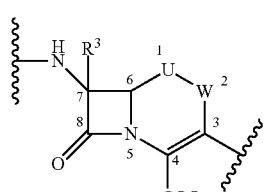

Esters of Formula (I) preferably include those esters at the carboxyl on the 7-side chain and/or at the 4-position. Esters at the carboxyl group on the 7-side chain can include compounds having a structure in which the carboxyl group of an optionally substituted amino group, optionally substituted aminosulfonyl group, carboxyl group, optionally substituted lower alkyloxycarbonyl group, optionally substituted carbamoyl group, substituted carbonyloxy group, or the like at the terminal of $R^1$, $R^{2A}$ or $R^{2B}$ shown in the formula:

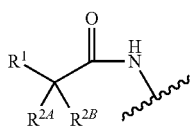

[Formula 45]

is esterified wherein each symbol is defined as in item 1 (for example, in the case of carboxyl (—COOH), such esters are represented by the structural formula —COOR$^a$, which is shown with R$^a$ representing an ester residue such as a carboxyl-protecting group or the like); and the like. Moreover, such esters encompass those esters that are easily metabolized in the body to form a carboxyl group.

Esters at the carboxyl group at the 4-position of Formula (I) refer to compounds having a structure in which the carboxyl group at the 4-position of the cephem skeleton is esterified as shown in the formula:

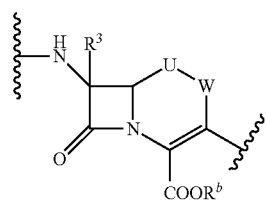

[Formula 46]

wherein each symbol is as defined in item 1, and R$^b$ is an ester residue such as a carboxyl-protecting group or the like. Such esters encompass those esters that are easily metabolized in the body to form a carboxyl group.

The aforementioned protecting groups for a carboxyl group may be of any group as long as it can be used for protection and/or deprotection by a method such as described in Protective Groups in Organic Synthesis, written by T. W. Green, John Wiley & Sons Inc. (1991) and for example include lower alkyl (e.g., methyl, ethyl, t-butyl), (lower)alkylcarbonyloxymethyl (e.g., pivaloyl), optionally substituted aralkyl (e.g., benzyl, benzhydryl, phenethyl, p-methoxybenzyl, p-nitrobenzyl), silyl groups (t-butyldimethylsilyl, diphenyl(t-butyl)silyl), and the like.

A protected compound at the amino on the 7-side chain of Formula (I) refers to the structures in which the amino on the ring has been protected, as shown in the formula:

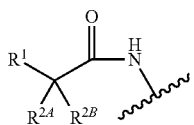

[Formula 47]

wherein each symbol is as defined in item 1; and when $R^1$ and/or $R^{2A}$ has an amino group, a protected form thereof is represented by the formula —NHR$^c$ wherein R$^c$ represents an amino-protecting group. Such amino-protecting groups include those groups that are readily metabolized in the body to form amino. The aforementioned amino-protecting groups may be of any group as long as it can be used for protection and/or deprotection by a method such as described in Protective Groups in Organic Synthesis, written by T. W. Green, John Wiley & Sons Inc. (1991) and for example include lower alkoxycarbonyl (e.g., t-butoxycarbonyl, benzyloxycarbonyl, p-nitrobenzyloxycarbonyl), optionally substituted aralkanoyl (e.g., benzoyl, p-nitrobenzoyl), acyl (e.g., formyl, chloroacetyl), and the like.

"$R^1$ is an aminothiazole of which the amino group is optionally protected, or an aminothiadiazole of which the amino group is optionally protected" refers to the formula:

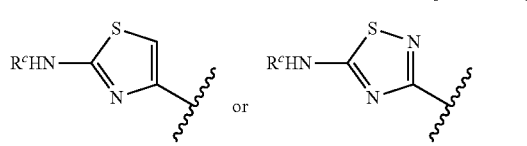

[Formula 48]

wherein R$^c$ is an amino-protecting group.

Salts of Formula (I) include those formed with a counter cation(s) after the hydrogen atom(s) of the carboxyl group at the 4-position, the carboxyl group at the 7-position, and/or the hydroxyl group of the pyridone derivative is dissociated; those formed with an inorganic or organic acid by the amino group in the 7-side chain; and those formed with a counter anion by the quaternary amine moiety in the 3-side chain.

Pharmaceutically acceptable salts of Formula (I) include, for example, salts or intramolecular salts formed with inorganic base, ammonia, organic base, inorganic acid, organic acid, basic amino acid, halogen ions, and the like. Such inorganic bases include, for example, alkali metal (Na, K, and the like) and alkali earth metal (Mg and the like). Organic bases include, for example, procaine, 2-phenylethylbenzyl amine, dibenzylethylenediamine, ethanolamine, diethanolamine, trishydroxymethylaminomethane, polyhydroxyalkylamine, N-methyl glucosamine, and the like. Inorganic acids include, for example, hydrochloric acid, hydrobromic acid, sulfuric acid, nitric acid, phosphoric acid, and the like. Organic acids include, for example, p-toluene sulfonic acid, methane sulfonic acid, formic acid, acetic acid, trifluoroacetic acid, maleic acid and the like. Basic amino acids include, for example, lysine, arginine, ornithine, histidine, and the like.

As used herein, "solvate" refers to a solvate with water or organic solvent (for example, methanol, ethanol, isopropyl alcohol, acetone), and preferably a hydrate.

The Compound (I) of the subject invention is not limited to particular isomers, but includes any possible isomers, racemates, and resonance structures as exemplified as follows:

For example, the formula in Formula (I):

[Formula 49]

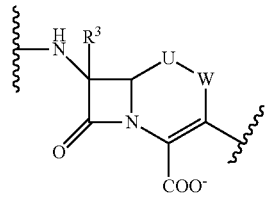

wherein each symbol is as defined in item 1, includes:

[Formula 50]

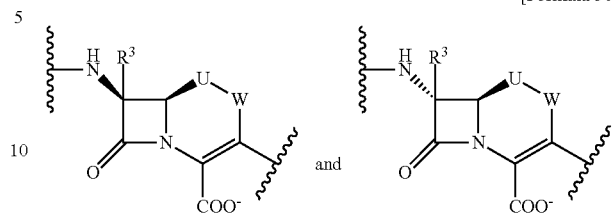

wherein each symbol is as defined in item 1.

For example, the formula in Formula (I):

[Formula 51]

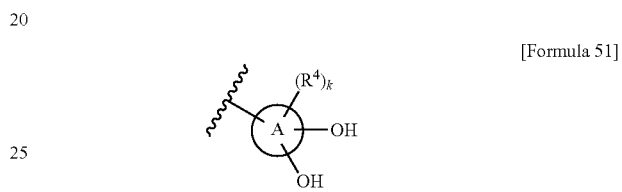

wherein each symbol is as defined in item 1, includes the following resonance structures:

[Formula 52]

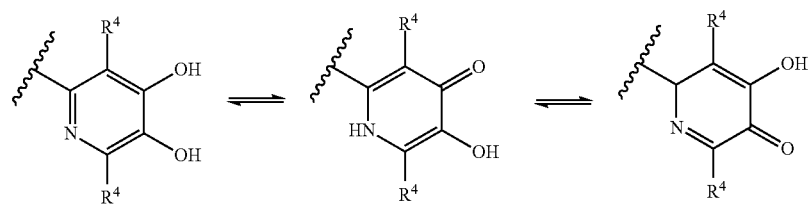

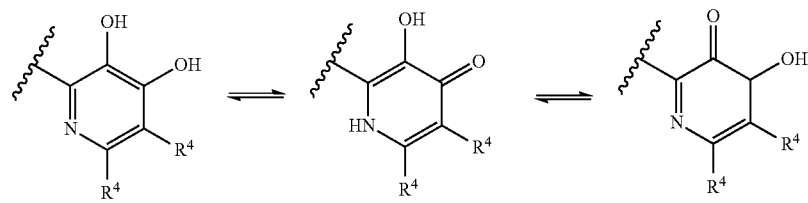

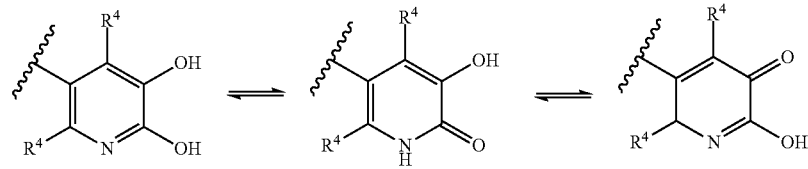

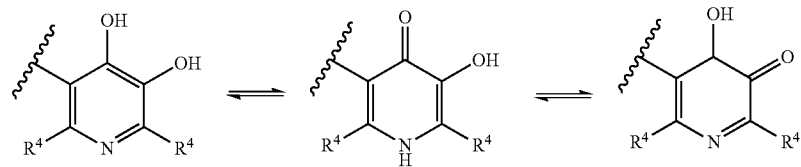

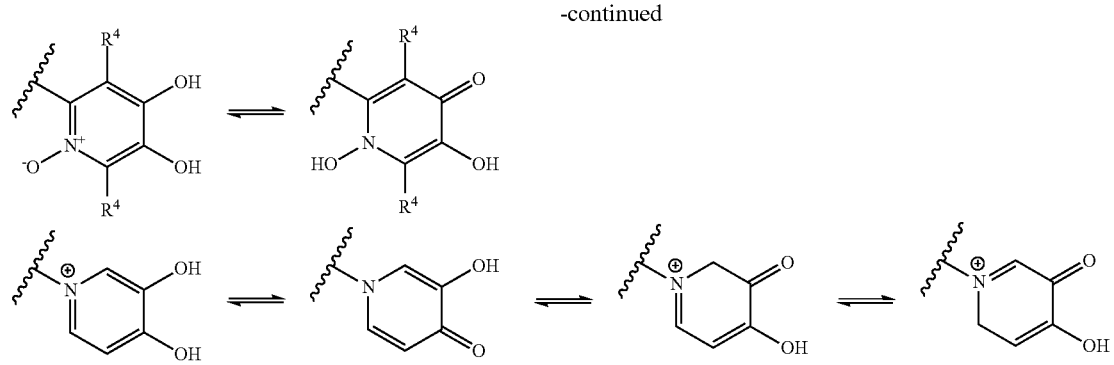
wherein $R^4$ is defined as in item 1,
and the like.
(Synthesis Method)
The compounds represented by Formula (I) of the subject invention can be manufactured, for example, by a general synthesis method described below:
[Formula 53]
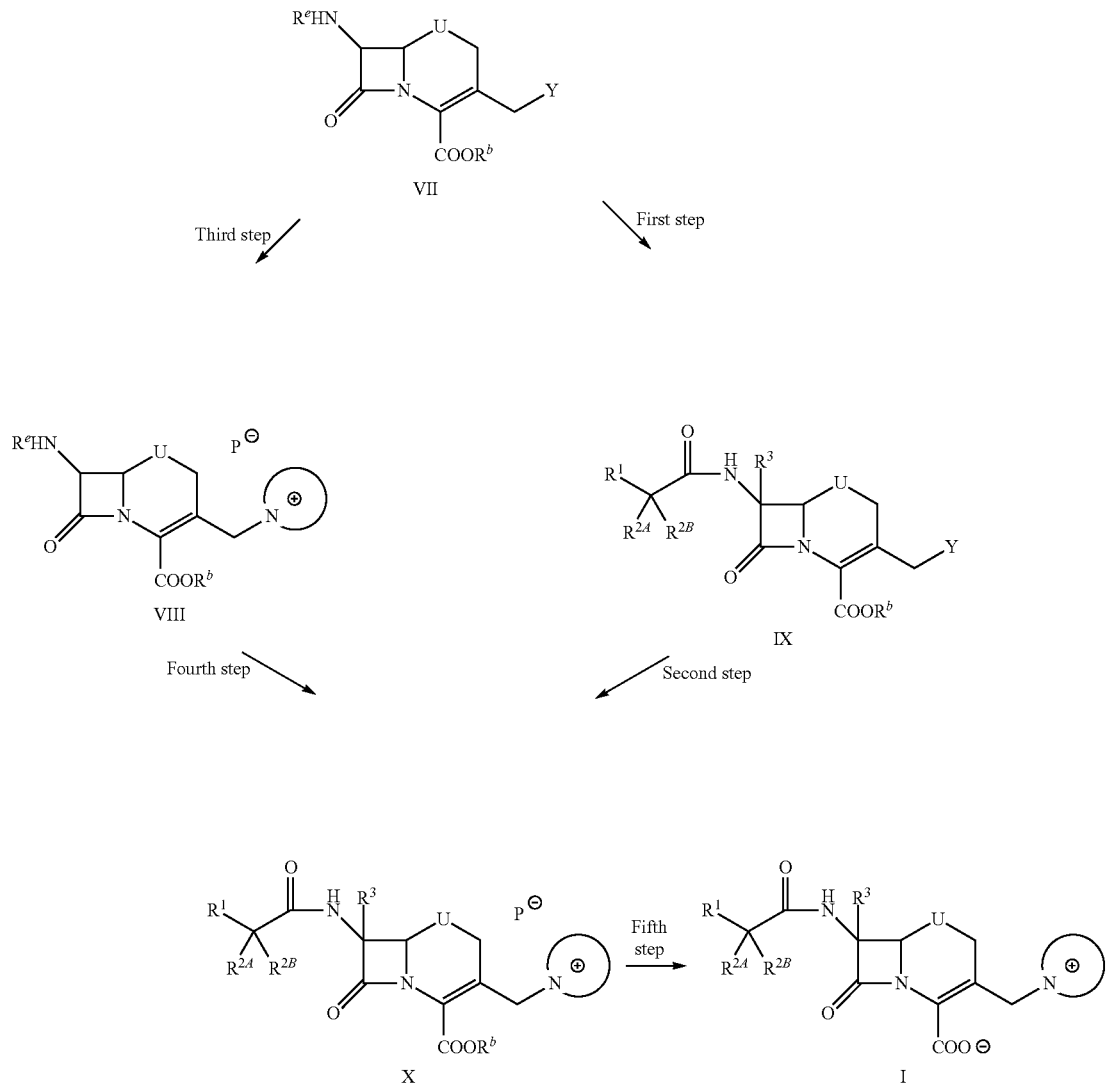

wherein U, $R^a$, and $R^b$ are as defined above, and $P^-$ is a counter anion of a quaternary amine; the formula:

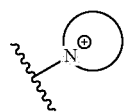
[Formula 54]

is a moiety of Formula (I) including a quaternary ammonium group moiety of the 3-side chain, as represented by the formula:

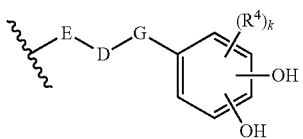
[Formula 55]

wherein each symbol is as defined above;
Y is a leaving group (for example, hydroxy, halogen (Cl, Br, I), and optionally substituted carbamoyloxy, acyloxy, methanesulfonyloxy, and toluenesulfonyloxy, etc.); and
$R^e$ is a hydrogen or an amino protecting group.
1) 7-Amidation and Formation of the 3-Side Chain; Synthesis of Compound (X)
The First Step (7-Amidation Reaction):
Compound (IX) is obtained by reacting Compound (VII), which is commercially available or synthesized according to methods described in a document (e.g., JP 60-231684 A, JP 62-149682 A, etc.), with a compound corresponding to a desired side chain as represented by the formula:

[Formula 56]

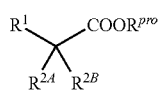
(VI)

wherein $R^{pro}$ is a hydrogen or carboxy-protecting group, and the other symbols are each as defined above. In this case, preferably, $R^b$ is a carboxy-protecting group, and $R^{pro}$ and $R^e$ are hydrogen. The compounds of formula (VI) can be obtained as commercially available reagents and/or by using known methods.
The amount of Compound (VI) used is in a range of, generally, about 1-5 moles, preferably 1-2 moles, relative to 1 mole of Compound (VII).
Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.
The reaction temperature is in a range of, generally, about −40 to 80° C., preferably about −20 to 50° C., more preferably about −10 to 30° C.

The above-described amidation reaction may be carried out after a carboxyl moiety is converted to a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, and the like), alkali earth metal (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide(WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.
The Second Step (3-Side Chain Forming Reaction):
Compound (X) is obtained by reacting Compound (IX) with a corresponding tertiary amine. In this case, preferably, $R^b$ is a carboxy protecting group.
The amount of the corresponding tertiary amine used is in a range of, generally, 1-5 moles, preferably 1-2 moles, relative to 1 mole of Compound (IX).
Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate); halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone); nitriles (e.g., acetonitrile (MeCN), propionitrile), dimethylsulfoxide, water, and the like, and mixed solvents and the like thereof.
The reaction temperature is in a range of, generally, −20 to 60° C., preferably −10 to 40° C., more preferably 0 to 20° C.
Furthermore, Compound (X) wherein U is S can be obtained by reducing Compound (X) wherein U=SO. Examples of reducing agents include potassium iodide-acetyl chloride, and the like.
3) 3-Side Chain Formation and 7-Amidation; Synthesis of Compound (X)
The Third Step (3-Side Chain Forming Reaction):
Compound (VIII) is obtained by reacting Compound (VII) with a corresponding tertiary amine. In this case, preferably, $R^b$ is a carboxy-protecting group, and $R^e$ is an amino-protecting group.
The amount of the corresponding tertiary amine used is in a range of, generally, 1-5 moles, preferably 1-2 moles, relative to 1 mole of Compound (VII).

Examples of reaction solvents include (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

The reaction temperature is in a range of, generally, −20 to 60° C., preferably −10 to 40° C., more preferably 0 to 20° C.

The tertiary amine moieties used in the 3-side chain forming reactions of the second and the third steps (corresponding to substituent E of item 1) can be obtained as a commercially available reagent, or by using a known method and/or a method described herein.

The Fourth Step (7-Amidation Reaction):

Compound (X) is obtained by reacting Compound (VIII) with Compound (VI). In this case, preferably, $R^b$ is a carboxy-protecting group, $R^c$ is an amino-protecting group, and $R^{pro}$ and $R^e$ are hydrogen.

The amount of Compound (VI) used is in a range of, generally, about 1-5 moles, preferably 1-2 moles, relative to 1 mole of Compound (VIII).

Examples of reaction solvents include ethers (e.g., dioxane, tetrahydrofuran, diethyl ether, tert-butyl methyl ether, diisopropyl ether), esters (e.g., ethyl formate, ethyl acetate, isopropyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), dimethylsulfoxide, water, and the like, and mixed solvents and the like thereof.

A reaction temperature is in a range of, generally, about −40 to 80° C., preferably about −20 to 50° C., more preferably about −10 to 30° C.

The above-described amidation reaction may be carried out after a carboxyl moiety is converted to a reactive derivative (e.g., inorganic base salt, organic base salt, acid halide, acid azide, acid anhydride, mixed acid anhydride, active amide, active ester, and active thioester). Examples of such inorganic bases include alkali metal (e.g., Na, K, and the like), alkali earth metal (e.g., Ca, Mg), and the like. Examples of organic bases include trimethylamine, triethylamine, tert-butyldimethylamine, dibenzylmethylamine, benzyldimethylamine, N-methylmorpholine, diisopropylethylamine, and the like. Examples of acid halides include acid chlorides, acid bromides, and the like. Examples of mixed acid anhydrides include mixed acid anhydrides of mono-alkyl carbonate, mixed acid anhydrides of aliphatic carboxylic acid, mixed acid anhydrides of aromatic carboxylic acid, mixed acid anhydrides of organic sulfonic acid, and the like. Examples of active amides include amides with nitrogen-containing heterocyclic compound, and the like. Examples of active esters include organic phosphoric esters (e.g., diethoxyphosphoric ester, diphenoxyphosphoric ester, and the like), p-nitrophenyl ester, 2,4-dinitrophenyl ester, cyanomethyl ester, and the like. Examples of active thioesters include esters with aromatic heterocyclic thiol compound (e.g., 2-pyridylthiol esters), and the like. Examples of active thioesters include esters with aromatic heterocyclic thiol compound (e.g., 2-pyridylthiol esters), and the like. Furthermore, in the above-described reaction, a suitable condensing agent may be used as desired. For example, hydrochloric acid salt of 1-dimethylaminopropyl-3-ethylcarbodiimide(WSCD.HCl), N,N'-dicyclohexylcarbodiimide, N,N'-carbonyldiimidazole, N,N'-thiocarbonyldiimidazole, N-ethoxycarbonyl-2-ethoxy-1,2-dihydroquinoline, phosphorus oxychloride, alkoxyacetylene, 2-chloromethylpyridinium iodide, 2-fluoromethylpyridinium iodide, trifluoroacetic anhydride, and the like can be used as a condensing agent.

Furthermore, Compound (X) wherein U is O can be obtained by using Compound (VII) wherein U is O.

4) Deprotection Reaction:

The Fifth Step:

Compound (I) is obtained by subjecting Compound (X) to a deprotection reaction by a method well-known to those skilled in the art.

Examples of reaction solvents include ethers (e.g., anisole, dioxane, tetrahydrofuran, diethyl ether, tert-butyl methyl ether, diisopropyl ether), esters (e.g., ethyl formate, ethyl acetate, n-butyl acetate), halogenated hydrocarbons (e.g., dichloromethane, chloroform, carbon tetrachloride), hydrocarbons (e.g., n-hexane, benzene, toluene), amides (e.g., formamide, N,N-dimethylformamide, N,N-dimethylacetamide, N-methylpyrrolidone), ketones (e.g., acetone, methyl ethyl ketone), nitriles (e.g., MeCN, propionitrile), nitro compounds (e.g., nitromethane, nitroethane, nitrobenzene), dimethylsulfoxide, water, and the like. These solvents may be used alone or in a combination using two or more of such solvents.

The reaction temperature is in a range of, generally, about −30 to 100° C., preferably about 0 to 50° C., more preferably about 0 to 10° C.

As a catalyst, Lewis acid (e.g., $AlCl_3$, $SnCl_4$, $TiCl_4$), protonic acid (e.g., HCl, HBr, $H_2SO_4$, HCOOH), and the like can be used.

The obtained Compound (I) is further chemically modified to obtain an ester, or a compound wherein the amino on the thiazole ring at the 7-position is protected, or a pharmaceutically acceptable salt, or a solvate thereof.

Examples of protecting groups (amino-protecting group, hydroxy-protecting group, and the like) can include protecting groups, such as ethoxycarbonyl, t-butoxycarbonyl, acetyl, benzyl, and the like, as described in Protective Groups in Organic Synthesis, written by T. W. Green, John Wiley & Sons Inc. (1981). Methods for the introduction and removal of a protecting group are those commonly used in synthetic organic chemistry (see, for example, methods described in Protective Groups in Organic Synthesis, written by T. W. Greene, John Wiley & Sons Inc. (1981)) or the like, or can be obtained in accordance therewith. Furthermore, a functional group included in each substituent can be converted by a known method (for example, those described in Comprehensive Organic Transformations, written by R. C. Larock (1989), and the like) in addition to the above production methods. Some of the compounds of the subject invention can be used as a synthetic intermediate, leading to a new derivative. Intermediates and target compounds produced in each of the above production methods can be isolated and purified by a purification method commonly used in synthetic organic chemistry, for example, subjecting them to neutralization, filtration, extraction, washing, drying, concentration, recrystallization, any kind of chromatography, or the like. Furthermore, intermediates can be subjected to a next reaction without any purification.

The compounds of the subject invention have a wide antimicrobial activity spectrum, and may be used for prevention or treatment against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

The compounds of the subject invention exhibit high antimicrobial activity in particular against Gram negative bacteria, preferably, Gram negative bacteria of enterobacteria (*E. coli, Klebsiella, Serratia, Enterobacter, Citrobacter, Morganella, Providencia, Proteus* and the like), Gram negative bacteria colonized in respiratory system (*Haemophilus, Moraxella* and the like), and Gram negative bacteria of glucose non fermentation (*Pseudomonas aeruginosa, Pseudomonas* other than *P. aeruginosa, Stenotrophomonas, Burkholderia, Acinetobacter* and the like). The compounds are stable against beta-lactamase belonging to classes A, B, C and D in which the beta-lactamase is produced by these Gram negative bacteria, and have high antimicrobial activity against a variety of beta-lactam drug resistant Gram negative bacteria, such as ESBL producing bacteria and the like. These are extremely stable against metallo-beta-lactamase belonging to Class B including in particular IMP type, VIM type, L-1 type and the like. Thus, these are effective against a variety of beta-lactam drug resistant Gram negative bacteria including Cephem and Carbapenem. Moreover, the compounds of the subject invention have antimicrobial activity against Gram positive bacteria including methicillin-resistant *Staphylococcus aureus* (MRSA), penicillin-resistant *Streptococcus pneumoniae* (PRSP), and the like. Still more preferable compounds have features regarding kinetics in the body, such as blood concentration in which such is highly bioavailable, long duration of effects, and/or significant tissue migration. More preferable compounds are safe in terms of side effects. More preferable compounds have high water solubility, and thus preferable as an injecting drug, in particular.

The compounds of the subject invention can be administered orally or parenterally. The compounds of the subject invention, when administered orally, can be used in any dosage form of normal formulations, for example, solid formulations such as tablet, powder, granule, capsule, and the like; liquid formulations such as solution, suspension in oil, or syrup or elixir. The compounds of the subject invention, when administered parenterally, can be used as an aqueous or oleaginous suspended injecting formulation, or nasal drops. In preparation thereof, any conventional excipient, binder, lubricant, aqueous solvent, oleaginous solvent, emulsifier, suspending agent, preservative, stabilizer, and the like can be used. As an anti-HIV agent, an oral agent is particularly preferred. A formulation of the subject invention is produced by combining (for example, mixing) a therapeutically effective amount of a compound of the subject invention with a pharmaceutically acceptable carrier or diluent.

The compounds of the subject invention may be administered parenterally or orally as injectable formulations, capsules, tablets, and granules, and preferably, administered as an injectable formulation. The dosage may usually be about 0.1 to 100 mg/day, preferably, about 0.5 to 50 mg/day, per 1 kg of body weight of a patient or animal, and optionally be divided into 2 to 4 times per day. The carriers for use in injectable formulation may be, for example, distilled water, saline, and the like, and further bases may be used for pH adjustment. The carriers for used in capsules, granules, or tablets includes known excipients (e.g., starch, lactose, sucrose, calcium carbonate, calcium phosphate and the like), binders (e.g., starch, acacia gum, carboxymethyl cellulose, hydroxypropyl cellulose, crystalline cellulose, and the like), lubricants (e.g., magnesium stearate, talc and the like), and the like.

EXAMPLES

Hereinafter, the subject invention is described in more details with working examples and experimental examples. However, the subject invention is not limited to them.

In the Examples, the meaning of each abbreviation is as described below.
ODS: Octadodecylsilyl
PMB: para-Methoxybenzyl
BH: Benzhydryl
Boc: tert-Butoxycarbonyl
t-Bu: tert-buthyl
Bn: benzyl
Trt: trithyl
Me: methyl
Cbz: benzylokycarbonyl Example 1

Synthesis of Compound (I-1)

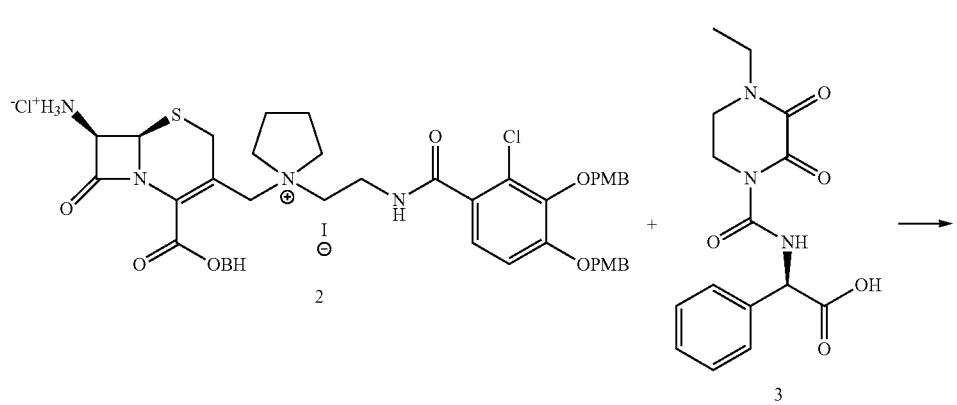

[Formula 57]

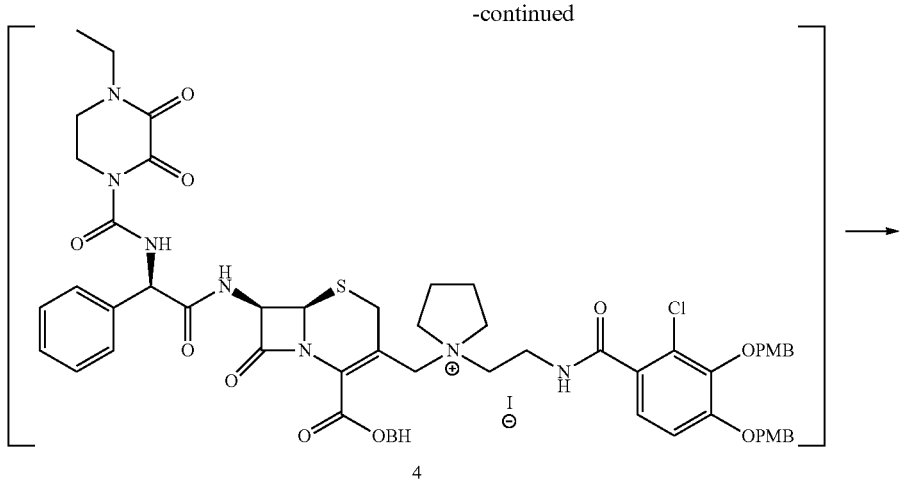

4

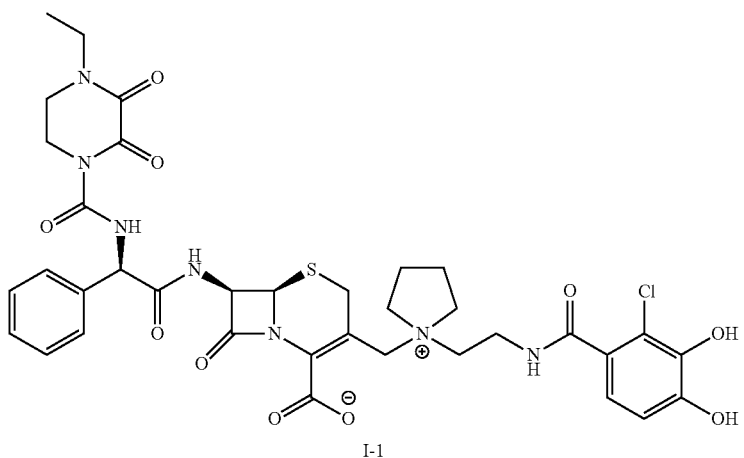

I-1

Step: Production of Compound (I-1) from Compound 2+Compound 3 via Compound 4

A solution of Compound 2 (1.07 g, 1.0 mmol) in methylene chloride (10 ml) was cooled to 0° C. Compound 3 (303 mg, 0.95 mmol), pyridine (105 μl, 1.3 mmol), and hydrochloric acid salt of 1-ethyl-3-(3-dimethylaminopropyl)carbodiimide (230 mg, 1.2 mmol) were added successively thereto, and then stirred at 0° C. for 3.5 hours. To the reaction mixture, 0.1 mol/L hydrochloric acid, ethyl acetate, and tetrahydrofuran were added, and then methylene chloride was evaporated under reduced pressure, followed by extraction with mixed solvent of ethyl acetate/tetrahydrofuran. The organic layer was washed with 0.1 mol/L hydrochloric acid, aqueous sodium hydrogen sulfite solution, then saturated brine, and then the solvent was evaporated under reduced pressure. The resulting concentrated residue was dissolved in methylene chloride, and then dried with anhydrous magnesium sulfate. After removing the inorganic substance by filtration, the filtrate was concentrated in vacuo, and then dried under reduced pressure to yield Compound 4 as a brown foam.

The whole amount of Compound 4 obtained was dissolved in methylene chloride (10 ml), and then cooled to −40° C. Subsequently, anisole (1.09 ml, 10 mmol) followed by 2 mol/L-aluminum chloride/nitromethane solution (5.0 ml, 10 mmol) were added, and then stirred at −40° C. for 1 hour. To the reaction solution, aqueous 2 mol/L hydrochloric acid, acetonitrile, and diisopropyl ether were added, and then stirred. The insoluble material was separated from the supernatant by decantation. The aqueous layer was separated from the supernatant. Meanwhile, aqueous diluted hydrochloric acid and acetonitrile were added to the insoluble attached to the container, and then stirred to dissolve the insoluble material completely. Diisopropyl ether was added thereto, and then the aqueous layer was separated. The organic layer was extracted with water again. All the aqueous layers were combined, and then HP20-SS resin was added thereto, subsequently evaporating acetonitrile in vacuo. The resulting mixed solution was then purified by ODS column chromatography. The fractions containing the desired compound were concentrated in vacuo, and then lyophilized to yield Compound (I-1) as a pale yellow powder.

Yield: 240 mg (30%)

$^1$H-NMR (DMSO-$d_6$) δ: 1.08 (3H, t, J=7.2 Hz), 2.02-2.08 (4H, m), 3.37-3.95 (17H, m), 4.99 (1H, d, J=5.1 Hz), 5.04 (1H, d, J=13.2 Hz), 5.58-5.64 (2H, m), 6.76 (2H, s), 7.26-7.44 (5H, m), 8.41 (1H, br), 9.46 (1H, d, J=7.8 Hz), 9.85 (1H, d, J=6.9 Hz)

MS (m+1)=798.35

Elemental analysis for: $C_{36}H_{40}ClN_7O_{10}S \cdot 3.4H_2O$

Calcd.: C, 50.31; H, 5.49; Cl, 4.12; N, 11.41; S, 3.73(%)

Found.: C, 50.27; H, 5.35; Cl, 4.22; N, 11.31; S, 3.88(%).

Example 2

Synthesis of Compound (I-2)

and then cooled to −60° C. Subsequently, tributylamine (951 μl, 4.0 mmol) was added thereto. To the resulting mixed solution, the above-described solution of the acid chloride was added dropwise over 30 minutes. After stirring at 0° C. for 1 hour, 0.5 mol/L hydrochloric acid was added to the reaction mixture, followed by extraction with methylene chloride. The organic layer was washed with 0.2 mol/L hydrochloric acid, aqueous sodium hydrogen sulfite solution, then saturated brine, and then dried with anhydrous magnesium sulfate. After removing the insoluble material through filtration, the filtrate was concentrated in vacuo, and then dried under reduced pressure to yield Compound 7 as a brown foam solid.

The whole amount of Compound 7 obtained was dissolved in methylene chloride (10 ml), and then cooled to −40° C. Subsequently, anisole (1.09 ml, 10 mmol) followed by 2 mol/L-aluminum chloride/nitromethane solution (5.0 ml, 10 mmol) were added, and then stirred at −40° C. for 1 hour. To

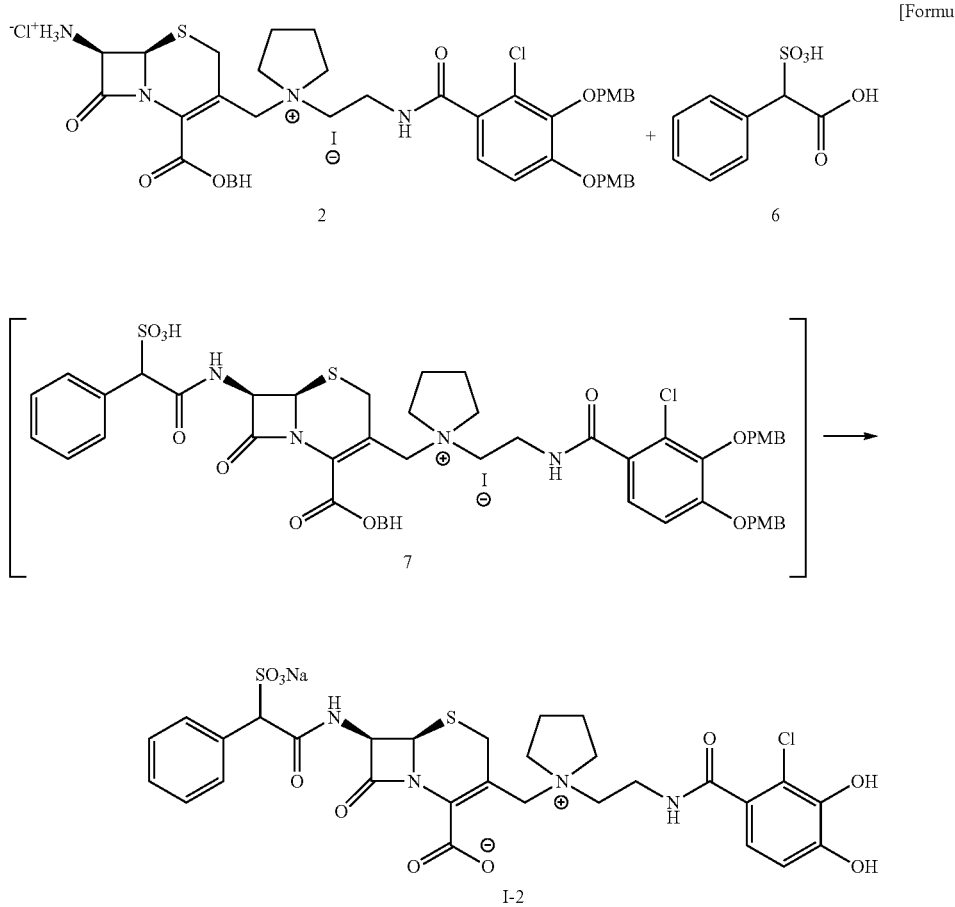

[Formula 58]

Step: Production of Compound (I-2) from Compound 2+Compound 6 via Compound 7

A solution of Compound 6 (238 mg, 1.1 mmol) in methylene chloride (10 ml) was cooled to 0° C. Diisopropylethylamine (480 μl, 2.75 mmol) followed by trimethylchlorosilane (422 μl, 3.3 mmol) were added, and then stirred at room temperature for 2 hours. After the reaction mixture was cooled to −30° C., thionyl chloride (96 μl, 1.32 mmol) was added thereto, and then stirred at 0° C. for 1 hour to form a solution of the acid chloride. Meanwhile, Compound 2 (1.07 g, 1.0 mmol) was dissolved in methylene chloride (10 ml), the reaction solution, aqueous 2 mol/L hydrochloric acid, acetonitrile, and diisopropyl ether were added, and then stirred. The insoluble material was then separated from the supernatant by decantation. The aqueous layer was separated from the supernatant. Meanwhile, aqueous diluted hydrochloric acid and acetonitrile were added to the insoluble material attached to the container, and then stirred to dissolve the insoluble material completely. Diisopropyl ether was added thereto, and then the aqueous layer was separated. The organic layer was extracted with water again, and then all the aqueous layers were combined. HP20-SS resin was added thereto, and then acetonitrile was evaporated in vacuo. The resulting mixed solution was purified by ODS column chromatography. To the fractions containing the desired compound, aqueous 0.2 mol/L sodium hydroxide solution was added to adjust pH=6.0, and then a piece of dry ice was added. The resulting solution was concentrated in vacuo, and then lyophilized to yield Compound (I-2) as a white powder.

Yield: 155 mg (22%)

$^1$H-NMR (D$_2$O) δ: 2.21 (4H, br), 3.35-4.56 (12H, m), 5.05 (1H, d, J=3.3 Hz), 5.25 (1H, dd, J=4.8, 19.8 Hz), 5.72 (1H, t, J=4.2 Hz), 6.85-6.95 (2H, m), 7.45 (3H, br), 7.60 (2H, br)

MS (m+1)=695.27

Elemental analysis for: C$_{29}$H$_{30}$ClN$_4$O$_{10}$S$_2$Na.0.1NaHCO$_3$.4.3H$_2$O Calcd.: C, 43.72; H, 4.83; Cl, 4.43; N, 7.01; S, 8.02; Na, 3.16(%).

Found.: C, 43.60; H, 4.70; Cl, 4.46; N, 7.26; S, 8.08; Na, 3.30(%).

Example 3

Synthesis of Compound (I-3)

Step: Production of Compound (I-3) from Compound 2+Compound 9 via Compound 10

The synthesis was carried out as described in Example 1 using Compound 2 (1.07 g, 1.0 mmol) and Compound 9 (415 mg, 0.95 mmol). After purification by ODS column chromatography, to the fractions containing the desired compound, aqueous 0.2 mol/L sodium hydroxide solution was added to adjust pH=6.0, and then a piece of dry ice was added. The resulting solution was concentrated in vacuo, and then lyophilized to yield Compound (I-3) as a white powder.

Yield: 160 mg (23%)

$^1$H-NMR (D$_2$O) δ: 2.14 (4H, br), 3.31-4.06 (12H, m), 4.42 (1H, d, J=5.7 Hz), 5.15 (1H, dd, J=5.1, 14.7 Hz), 5.63 (1H, dd, J=4.8, 8.1 Hz), 6.81 (1H, d, J=8.4 Hz), 6.87 (2H, br), 7.17 (1H, d, J=7.2 Hz)

MS (m+1)=675.27

Elemental analysis for: C$_{30}$H$_{30}$ClN$_4$O$_{10}$SNa.4.0H$_2$O

Calcd.: C, 46.85; H, 4.98; Cl, 4.61; N, 7.28; S, 4.17; Na, 2.99(%).

Found. C, 46.83; H, 4.88; Cl, 4.88; N, 7.20; S, 3.78; Na, 3.00(%).

[Formula 59]

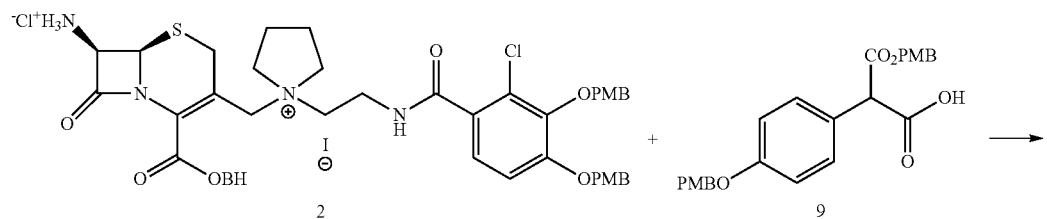

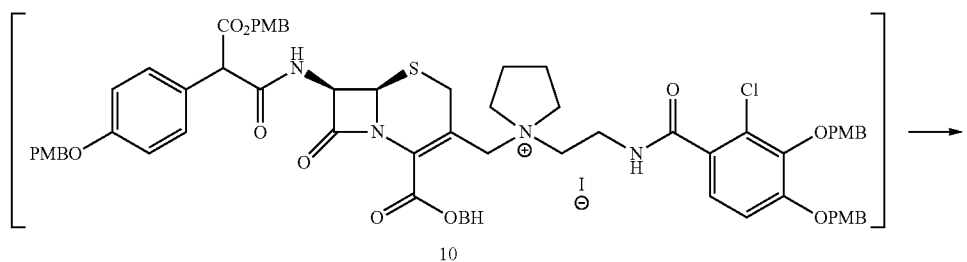

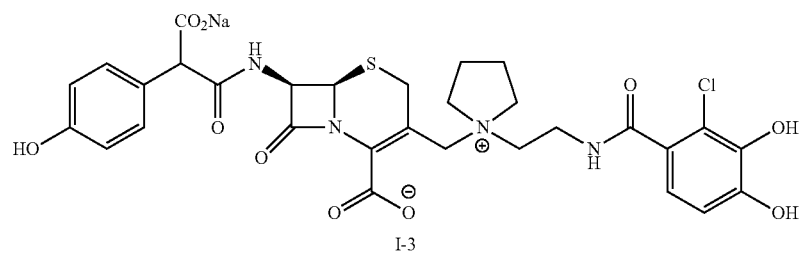

Example 4

Synthesis of Compound (I-4)

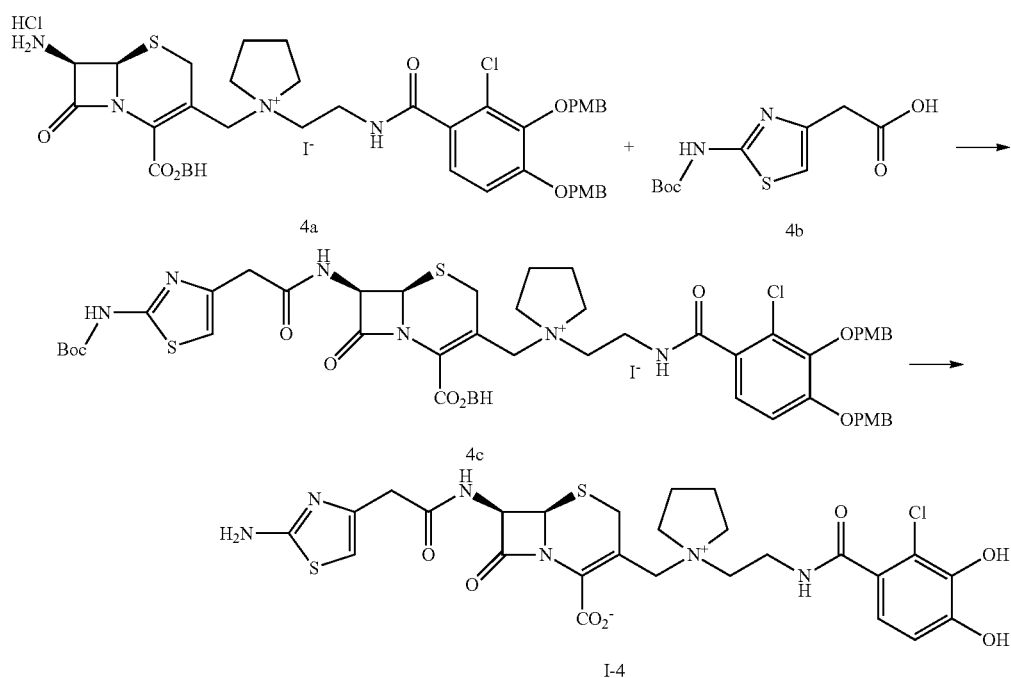

[Formula 60]

Step (1): Compound 4a+Compound 4b→Compound 4c

To Compound 4a (1.07 g, 1.00 mmol) in dichloromethane (10 mL) were added 4b (258 mg, 1.00 mmol), pyridine (105 μl, 1.30 mmol) and 1-ethyl-3-(3-dimethylaminopropyl)carbodiimide hydrochloride (230 mg, 1.20 mmol), and the liquid was stirred at 0° C. for 3.5 hours under ice-cooling. The reaction liquid was diluted with ethyl acetate/tetrahydrofurane, washed with aqueous hydrochloric acid, water, aqueous sodium hydrogen sulfite and brine, and dried over magnesium sulfate. Magnesium sulfate was filtrated off, and then the liquid was concentrated under reduced pressure to yield compound 4c.

Step (2): Compound 4c→Compound (I-4)

The total amount of compound 4c yielded was dissolved in methylene chloride (10 mL), and the solution was cooled to −40° C. Thereto were then added anisole (874 μl, 8.00 mmol) and 2 mol/L aluminum chloride solution (4.00 mL, 8.00 mmol) in nitromethane in turn. The resultant was stirred at 0° C. for 1 hour. The reaction liquid was dissolved in water, 2 mol/L aqueous hydrochloric acid solution, and acetonitrile. The resultant solution was then washed with diisopropyl ether. To the aqueous layer was added HP20SS resin, and then acetonitrile was distilled off under reduced pressure. The resultant mixed liquid was purified by ODS column chromatography. The resultant solution was concentrated under reduced pressure, and then freeze-dried to yield compound (I-4) as a pale orange powder.

Yield: 186.4 mg, (29%)

$^1$H-NMR (DMSO-$d_6$) δ: 10.31 (1H, br s), 9.36 (1H, br s), 8.84 (1H, d, J=8.39 Hz), 8.42 (1H, br s), 6.91 (2H, br s), 6.77 (2H, s), 6.24 (1H, s), 5.58 (1H, dd, J=8.16, 5.11 Hz), 5.09-5.07 (2H, m), 3.92-3.76 (3H, m), 3.41-3.57 (7H, m), 1.97-2.15 (4H, m).

Elemental analysis for: C26H29ClN6O7S2(H2O)2.1

Calcd.: C, 46.27; H, 4.96; Cl, 5.25; N, 12.45; S, 9.50(%).

Found.: C, 46.42; H, 5.02; Cl, 5.16; N, 12.43; S, 9.29(%).

Example 5

Synthesis of Compound (I-5)

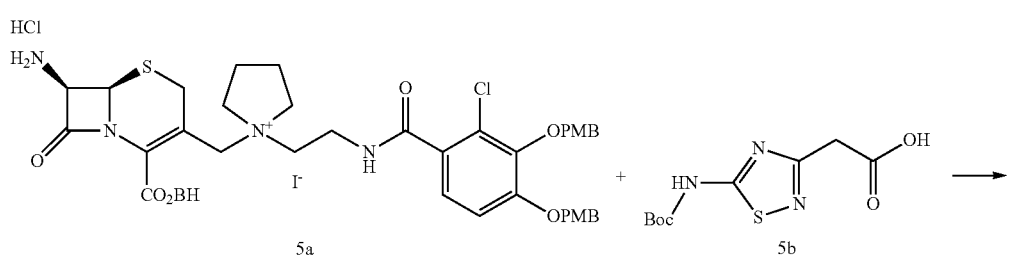

[Formula 61]

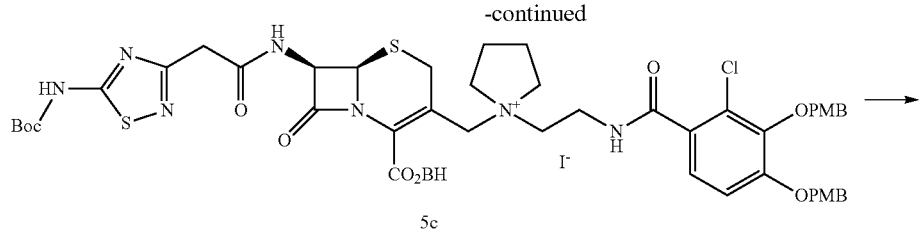

5c

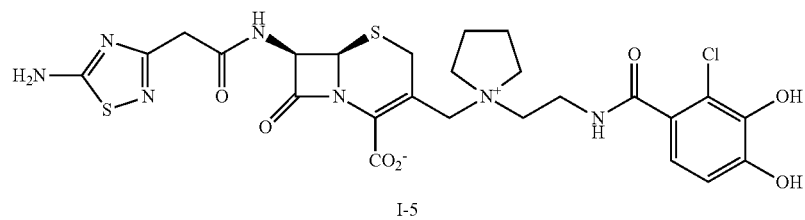

I-5

Step (1): Compound 5a+Compound 5b→Compound 5c

Compound 5a (1.07 g, 1.00 mmol) and compound 5b (259 mg, 1.00 mmol) were used to synthesize the target compound in the same way as in Example 4.

Step (2): Compound 5c→Compound (I-5)

The total amount of compound 5c yielded was used to synthesize the target compound in the same way as in Example 4.

Yield: 133.0 mg, (18%)

Elemental analysis for: C25H28ClN7O7S2(H2O)2.2
Calcd.: C, 44.30; H, 4.82; Cl, 5.23; N, 14.47; S, 9.46(%).
Found.: C, 44.36; H, 4.82; Cl, 5.26; N, 14.36; S, 9.41(%).

Example 6

Synthesis of Compound (I-6)

[Formula 62]

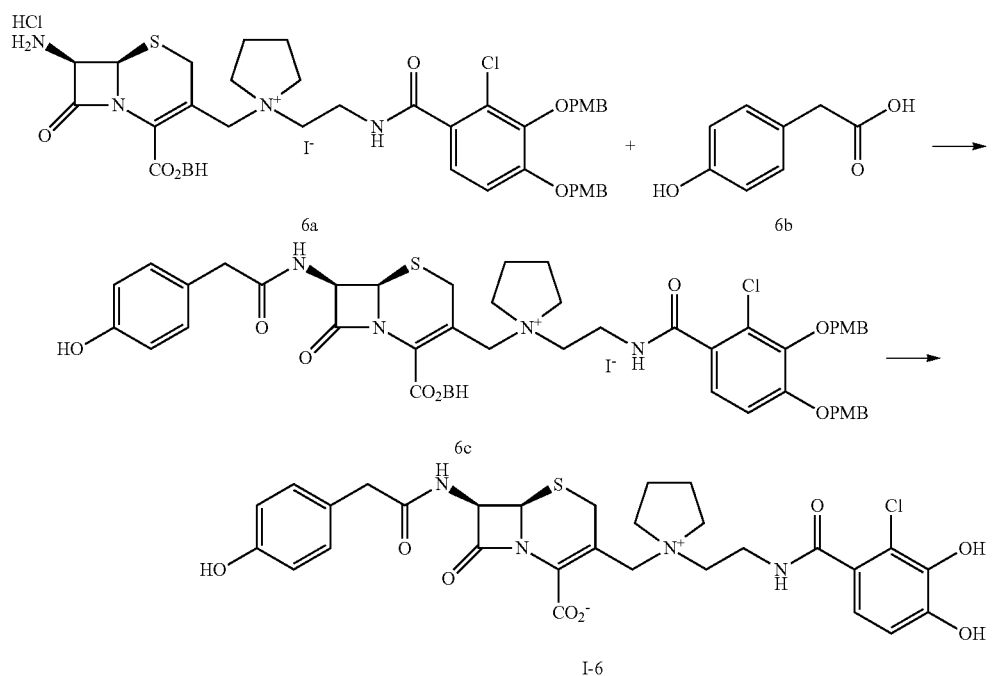

$^1$H-NMR (DMSO-$d_5$) δ: 10.33 (1H, br s), 9.36 (1H, br s), 9.00 (1H, d, J=8.39 Hz), 8.42 (1H, t, J=5.49 Hz), 7.92 (2H, br s), 6.77 (2H, s), 5.59 (1H, dd, J=8.39, 5.03 Hz), 5.10-5.08 (2H, m), 3.93-3.42 (13H, m), 1.96-2.15 (4H, m).

Step (1): Compound 6a+Compound 6b→Compound 6c

Compound 6a (1.07 g, 1.00 mmol) and compound 6b (152 mg, 1.00 mmol) were used to synthesize the target compound in the same way as in Example 4.

Step (2): Compound 6c→Compound (I-6)

The total amount of compound 6c yielded was used to synthesize the target compound in the same way as in Example 4.

Yield 110.0 mg, (15%)

$^1$H-NMR (DMSO-d$_6$) δ: 10.15 (1H, br s), 9.25 (2H, br s), 8.95 (1H, d, J=8.23 Hz), 8.40 (1H, t, J=5.46 Hz), 7.05 (2H, d, J=8.39 Hz), 6.79 (1H, d, J=8.39 Hz), 6.75 (1H, d, J=8.39 Hz), 6.66 (2H, d, J=8.39 Hz), 5.52 (1H, dd, J=8.06, 5.04 Hz), 5.09 (1H, d, J=13.43 Hz), 5.05 (1H, d, J=5.04 Hz), 3.91-3.74 (3H, m), 3.57-3.44 (7H, m), 2.14-1.99 (4H, m).

Elemental analysis for: C29H31ClN4O8S(H2O)2.5

Calcd.: C, 51.51; H, 5.37; Cl, 5.24; N, 8.29; S, 4.74(%).

Found.: C, 51.57; H, 5.36; Cl, 5.23; N, 8.19; S, 4.86(%).

Example 7

Synthesis of Compound (I-7)

Step (1): Compound 7a+Compound 7b→Compound 7c

Compound 7a (1.07 g, 1.00 mmol) and compound 7b (439 mg, 1.00 mmol) were used to synthesize the target compound in the same way as in Example 4.

Step (2): Compound 7c→Compound (I-7)

The total amount of compound 7c yielded was used to synthesize the target compound in the same way as in Example 4.

Yield 206.3 mg, (28%)

$^1$H-NMR (DMSO-d$_6$) δ: 11.45 (1H, br s), 10.47 (1H, br s), 9.59 (1H, d, J=7.89 Hz), 8.42 (1H, t, J=5.46 Hz), 7.25 (1H, dd, J=12.42, 2.01 Hz), 7.15 (1H, dd, J=8.39, 1.68 Hz), 7.00 (1H, t, J=8.73 Hz), 6.78 (2H, s), 5.72 (1H, dd, J=7.72, 5.04 Hz), 5.17 (1H, d, J=5.04 Hz), 5.06 (1H, d, J=13.43 Hz), 3.95-3.73 (4H, m), 3.59-3.44 (9H, m), 1.97-2.15 (4H, m).

Elemental analysis for: C29H29ClFN5O9S(H2O)2.2

Calcd.: C, 48.53; H, 4.69; Cl, 4.94; F, 2.65; N, 9.76; S, 4.47(%).

Found.: C, 48.51; H, 4.78; Cl, 4.95; F, 2.54; N, 9.69; S, 4.52(%).

[Formula 63]

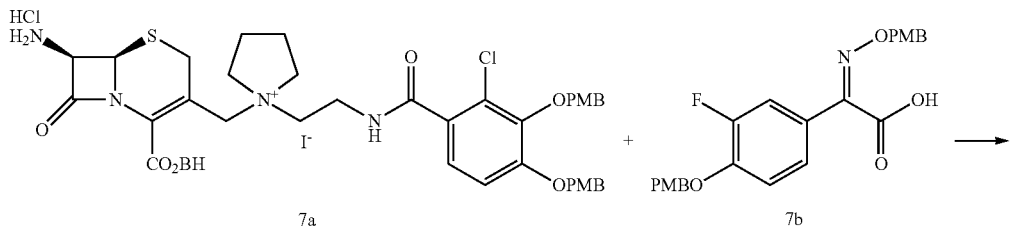

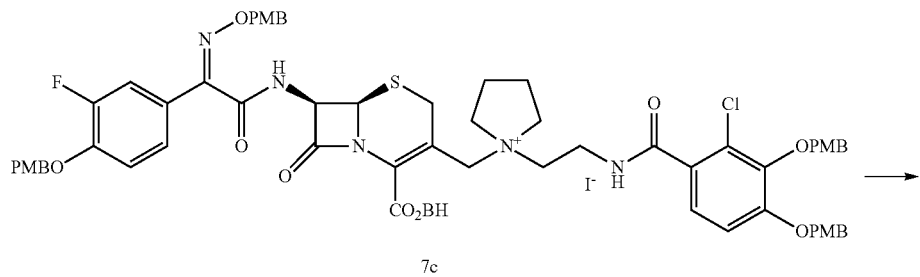

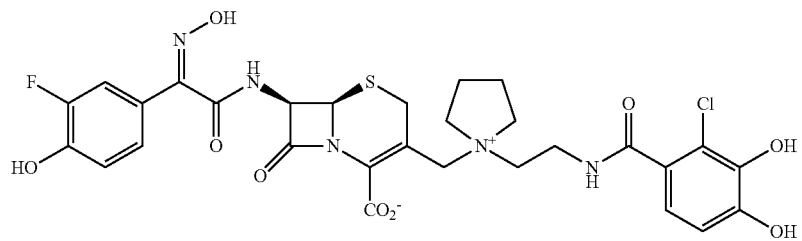

Example 8

Synthesis of Compound (I-8)

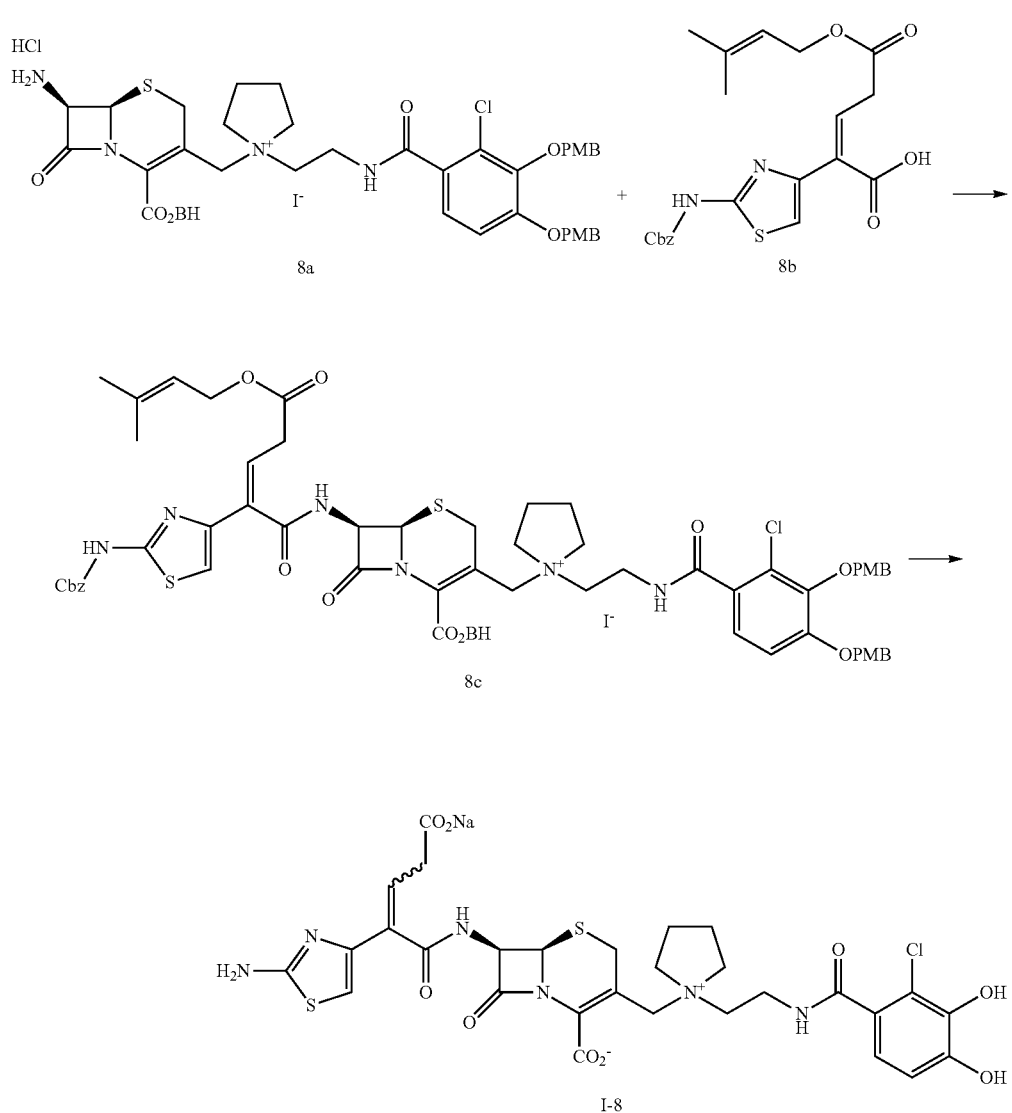

Step (1): Compound 8a+Compound 8b→Compound 8c

Compound 8a (1.07 g, 1.00 mmol) and compound 8b (430 mg, 1.00 mmol) were used to synthesize the target compound in the same way as in Example 4.

Step (2): Compound 8c→Compound (I-8)

The total amount of compound 8c yielded was dissolved in methylene chloride (10 mL), and the solution was cooled to −40° C. Thereto were then added anisole (1.092 mL, 10.0 mmol) and a 2 mol/L aluminum chloride solution (5.00 mL, 10.0 mmol) in nitromethane in turn. The resultant was stirred for 1 hour under ice-cooling. Thereto was added 2 mol/L aluminum chloride solution (5.00 mL, 10.0 mmol) in nitromethane, and the resultant was stirred at room temperature for 1 hours. The reaction liquid was dissolved in water, 2 mol/L aqueous hydrochloric acid solution, and acetonitrile, and the resultant solution was then washed with diisopropyl ether. To the aqueous layer was added HP20SS resin, and then acetonitrile was distilled off under reduced pressure. The resultant mixed liquid was purified by ODS column chromatography. To the resultant target-compound solution was added 0.2 mol/L aqueous sodium hydroxide solution until the whole gave pH of 6.0. Thereafter, a piece of dry ice was added thereto. The resultant solution was concentrated under reduced pressure, and then freeze-dried to yield compound (I-8) as a pale yellow powder.

Yield 96.9 mg, (11%)

$^1$H-NMR (D$_2$O) δ: 6.97-6.87 (2H, m), 6.68-6.59 (1H, m), 6.52-6.47 (1H, m), 5.85-5.78 (1H, m), 5.37-5.29 (1H, m), 4.17-4.11 (1H, m), 3.97-3.50 (10H, m), 3.24-3.22 (2H, m), 2.87 (1H, s), 2.23 (4H, br s)

Elemental analysis for: C29H30ClN6O9S2Na(H2O)3.7

Calcd.: C, 43.77; H, 4.74; Cl, 4.45; N, 10.56; S, 8.06; Na, 2.89(%).

Found.: C, 43.57; H, 4.83; Cl, 4.41; N, 10.84; S, 8.06; Na, 2.39(%).

71
Example 9
Synthesis of Compound (I-9)
72
Step (1): Compound 9a→Compound 9b
To Compound 9a (10.0 g, 44.2 mmol) in pyridine (100 mL) was added selenium dioxide (9.81 g, 88 mmol), and the solution was stirred at 80° C. for 10 hours. The reaction liquid
[Formula 65]
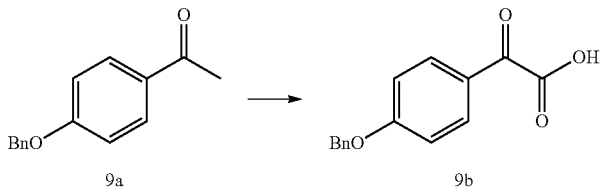
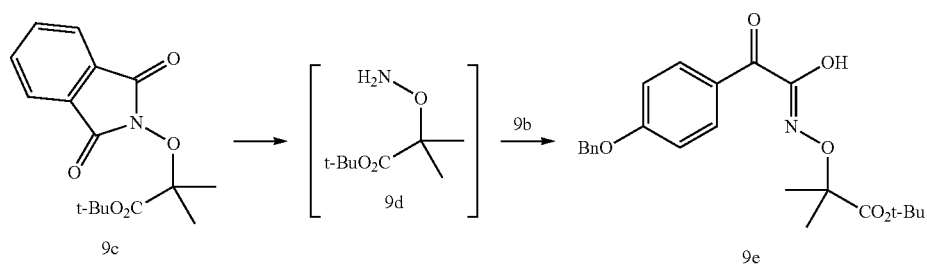
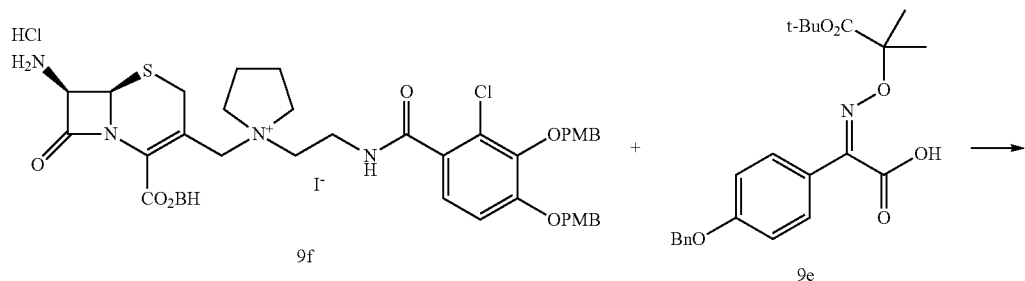
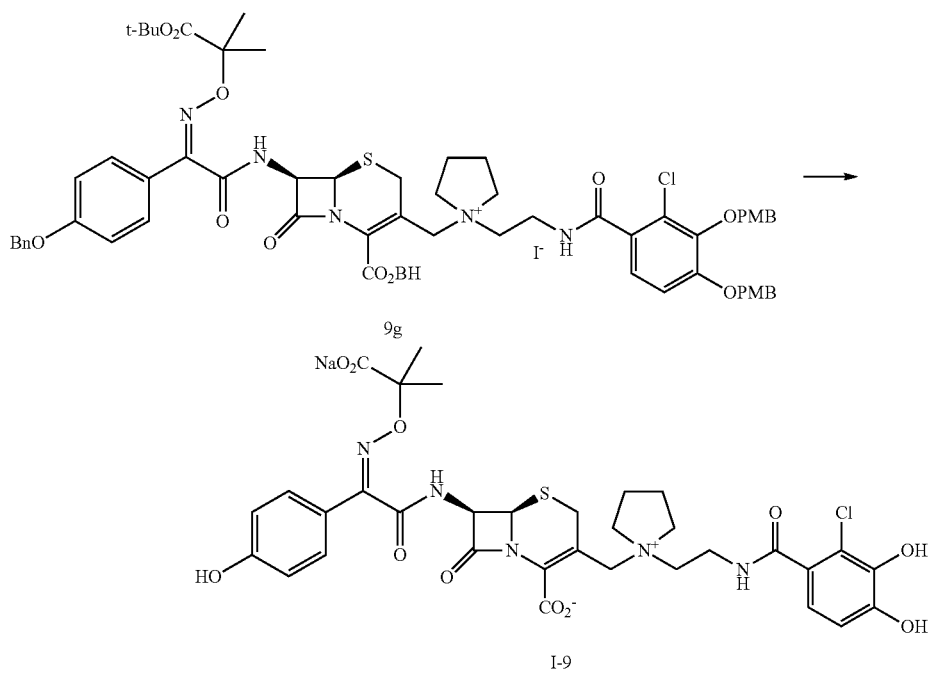

was filtrated off, and then the filtrate was concentrated under reduced pressure. The residue was diluted with ethyl acetate, washed with an aqueous hydrochloric acid solution, water and brine, and dried over magnesium sulfate. Magnesium sulfate was filtrated off, and then the liquid was concentrated under reduced pressure to yield compound 9b (10.37 g, 92%).

$^1$H-NMR (DMSO-$d_6$) δ: 7.90 (2H, d, J=8.90 Hz), 7.32-7.48 (5H, m), 7.22 (2H, d, J=8.90 Hz), 5.25 (2H, s).

Step (2): Compound 9c→Compound 9d+Compound 9b→Compound 9e

A solution of compound 9c (3.00 g, 9.83 mmol) in methylene chloride (30 mL) was cooled to −30° C., and then methylhydrazine (575 µl, 10.8 mmol) was added thereto, followed by stirring at room temperature for 30 minutes. The reaction solution was filtrated, and toluene was added to the filtrate, which was then concentrated under reduced pressure. Thereto were added methanol (30 mL) and Compound 9b (2.52 g, 9.83 mmol) in turn, and the liquid was stirred at room temperature for 1 hour. The reaction liquid was concentrated under reduced pressure. Thereto was added diisopropyl ether to precipitate a solid. The solid was collected by filtration to yield Compound 9e (1.83 g, 45%).

$^1$H-NMR (DMSO-$d_6$) δ: 13.95 (1H, s), 7.33-7.46 (7H, m), 7.11 (2H, d, J=8.90 Hz), 5.15 (2H, s), 1.43 (6H, s), 1.38 (9H, s).

Step (3): Compound 9f+Compound 9e→Compound 9g

Compound 9f (1.07 g, 1.00 mmol) and compound 9e (413 mg, 1.00 mmol) were used to synthesize the target compound in the same way as in Example 4.

Step (4): Compound 9g→Compound (I-9)

The total amount of compound 9g yielded was dissolved in methylene chloride (10 mL), and the solution was cooled to −40° C. Thereto were then added anisole (1.092 mL, 10.0 mmol) and 2 mol/L aluminum chloride solution (5.00 mL, 10.0 mmol) in nitromethane in turn, and the resultant was stirred for 1 hour under ice-cooling. The reaction liquid was dissolved in water, 2 mol/L aqueous hydrochloric acid solution, and acetonitrile, and the resultant solution was then washed with diisopropyl ether. To the aqueous layer was added HP20SS resin, and then acetonitrile was distilled off under reduced pressure. The resultant mixed liquid was purified by ODS column chromatography. To the resultant target-compound solution was added 0.2 mol/L aqueous sodium hydroxide solution until the solution become pH=6.0. Thereafter, a piece of dry ice was added thereto. The resultant solution was concentrated under reduced pressure, and then freeze-dried to yield Compound (I-9) as a pale yellow powder.

Yield: 132.6 mg, (15%).

$^1$H-NMR ($D_2O$) δ: 7.55 (2H, d, J=8.73 Hz), 6.96-6.86 (4H, m), 5.90 (1H, d, J=4.95 Hz), 5.39 (1H, d, J=4.95 Hz), 4.15 (1H, d, J=14.27 Hz), 3.99-3.48 (11H, m), 2.24 (4H, br s), 1.51 (3H, s), 1.50 (3H, s).

Elemental analysis for: C33H35ClN5O11SNa(H2O)5.3

Calcd.: C, 45.89; H, 5.32; Cl, 4.11; N, 8.11; S, 3.71; Na, 2.66(%).

Found.: C, 45.74; H, 5.06; Cl, 4.94; N, 8.04; S, 3.86; Na, 2.54(%).

Example 10

Synthesis of Compound (I-10)

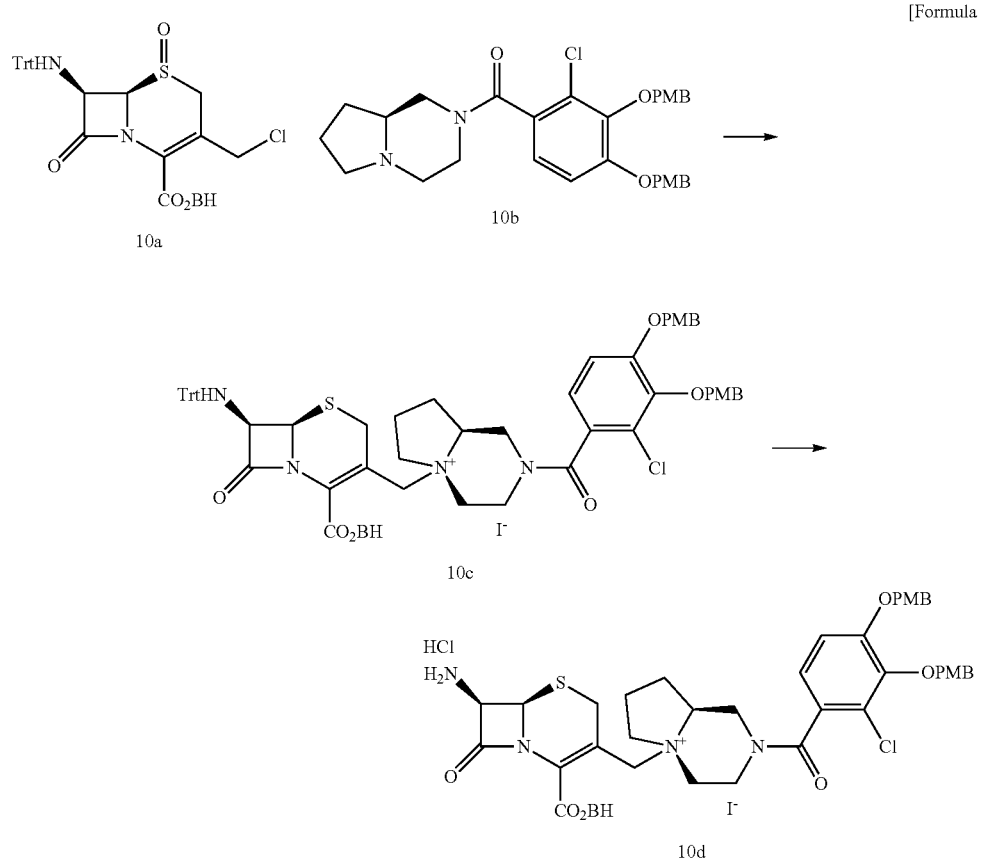

[Formula 66]

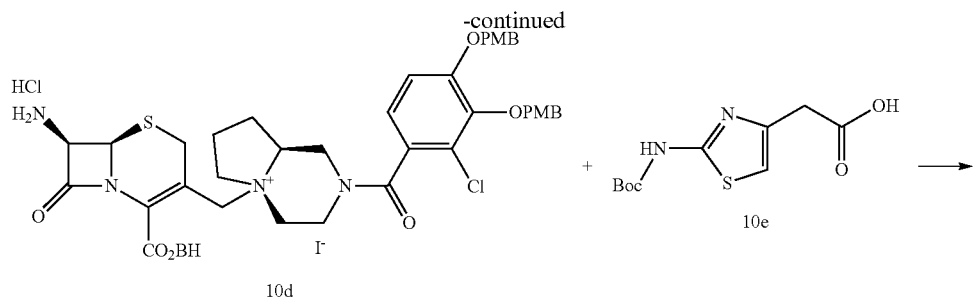

10d

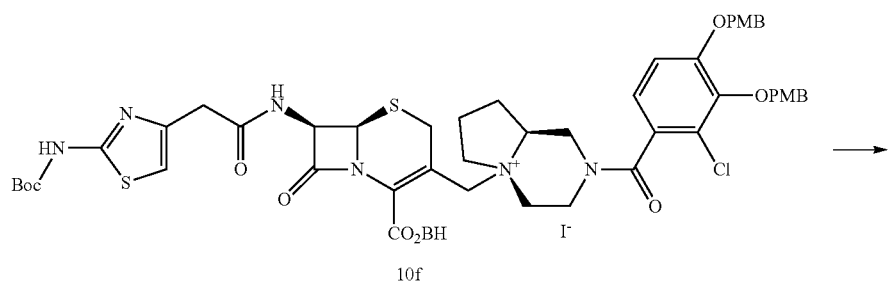

10f

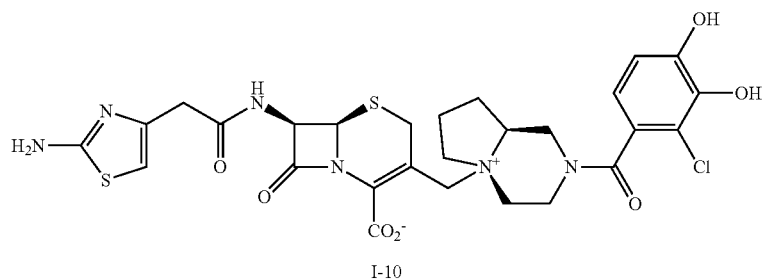

I-10

Step (1): Compound 10a+Compound 10b→Compound 10c

To Compound 10a (13.5 g, 20.0 mmol) and Compound 10b (10.7 g, 20.0 mmol) in dimethylacetamide (60 mL) was added sodium iodide (8.99 g, 60.0 mL), followed by stirring at room temperature for 3 hours. Dimethylformamide (60 mL) was added to the reaction solution under ice-cooling, and then potassium iodide (26.6 g, 160 mmol) and acetyl chloride (8.56 mL, 120 mL) were added thereto in turn, subsequently stirring for 2 hours under ice-cooling. The reaction solution was then poured into a solution of sodium hydrogen sulfite (20.8 g, 200 mmol) in 5% sodium chloride solution (600 mL) under ice-cooling. The precipitated solid was collected by filtration, washed with water, and then suspended into water. The suspension was freeze-dried to yield compound 10c (28.5 g) as a pale yellow solid. The obtained compound 10c was used in the next reaction without purification.

Step (2): Compound 10c→Compound 10d

The total amount of compound 10c yielded (28.5 g) was dissolved in acetone (80 mL), and then aqueous 6 mol/L hydrochloric acid solution (5.00 mL, 30.0 mmol) was added, and the solution was stirred at room temperature for 6 hours. The reaction liquid was diluted with dichloromethane, and then dried over magnesium sulfate. Magnesium sulfate was filtrated off, and then the liquid was concentrated under reduced pressure to yield compound 10d (26.96 g, 125%).

Step (3): Compound 10d+Compound 10e→Compound 10f

Compound 10d (1.08 g, 1.00 mmol) and compound 10e (258 mg, 1.00 mmol) were used to synthesize the target compound in the same way as in Example 4.

Step (4): Compound 10f→Compound (I-10)

The total amount of compound 10f yielded was used to synthesize the target compound in the same way as in Example 4.

Yield 183.0 mg, (25%)

$^1$H-NMR (DMSO-$d_6$) δ: 10.27 (1H, br s), 9.52 (1H, br s), 8.83 (1H, d, J=8.39 Hz), 6.91 (2H, br s), 6.81 (1H, d, J=8.16 Hz), 6.63 (1H, d, J=8.16 Hz), 6.24 (1H, s), 5.60-5.55 (1H, m), 5.21-5.01 (2H, m), 4.31-3.45 (10H, m), 1.87-2.27 (5H, m).

Elemental analysis for: $C_{27}H_{29}ClN_6O_7S_2(H_2O)_3$

Calcd.: C, 46.12; H, 5.02; Cl, 5.04; N, 11.95; S, 9.12(%)

Found.: C, 46.17; H, 5.07; Cl, 5.08; N, 11.89; S, 9.00(%).

Example 11

Synthesis of Compound (I-11)

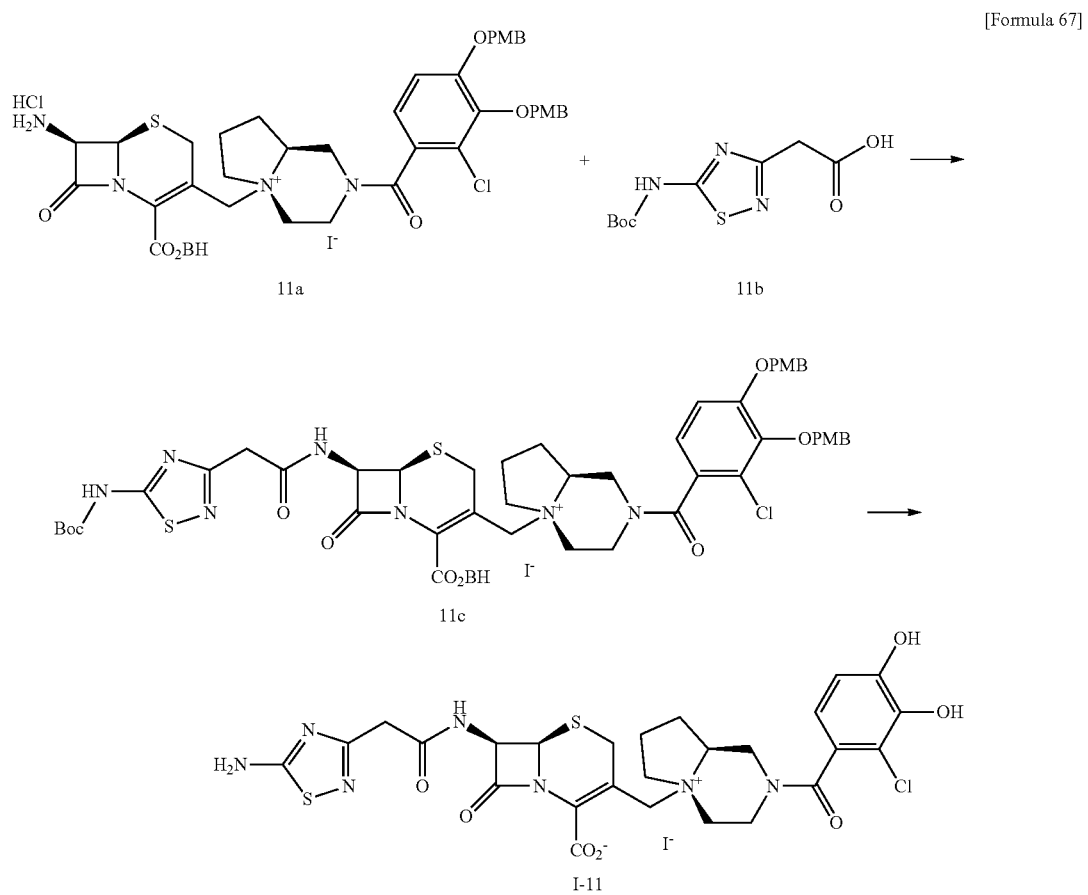

[Formula 67]

Step (1): Compound 11a+Compound 11b→Compound 11c

Compound 11a (1.08 g, 1.00 mmol) and compound 11b (259 mg, 1.00 mmol) were used to synthesize the target compound in the same way as in Example 4.

Step (2): Compound 11c→Compound (I-11)

The total amount of compound 11c yielded was used to synthesize the target compound in the same way as in Example 4.

Yield 301.9 mg, (39%)

$^1$H-NMR (DMSO-$d_6$) δ: 10.41 (1H, br s), 9.56 (1H, br s), 9.01 (1H, d, J=8.08 Hz), 7.93 (2H, br s), 6.83 (1H, d, J=8.16 Hz), 6.63 (1H, d, J=8.16 Hz), 5.61-5.57 (1H, m), 5.22-5.02 (2H, m), 4.29-3.47 (12H, m), 1.91-2.27 (5H, m).

Elemental analysis for: C26H28ClN7O7S2(H2O)3.3

Calcd.: C, 44.01; H, 4.91; Cl, 5.00; N, 13.82; S, 9.04(%).

Found.: C, 44.00; H, 4.88; Cl, 5.04; N, 13.67; S, 9.21(%).

Example 12

Synthesis of Compound (I-12)

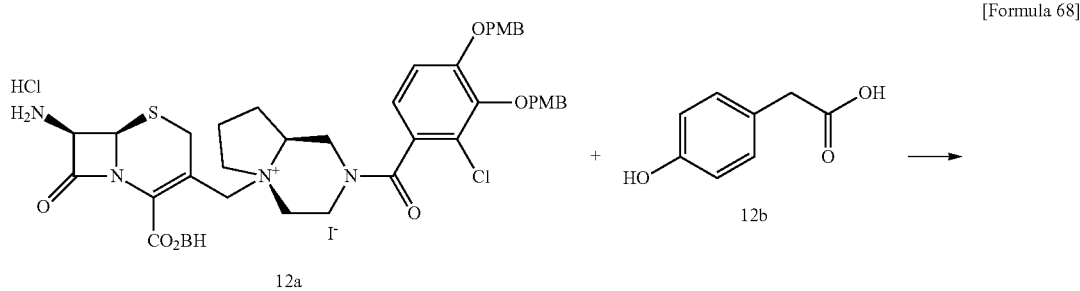

[Formula 68]

-continued

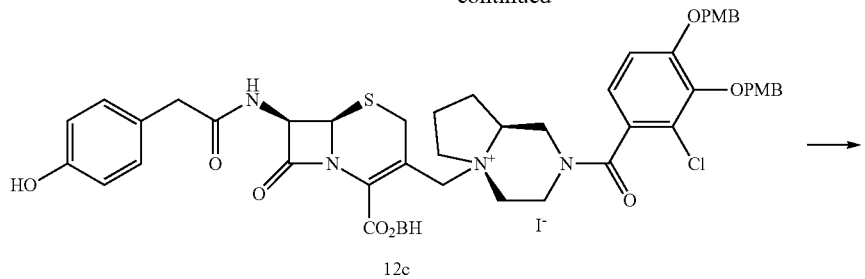

12c

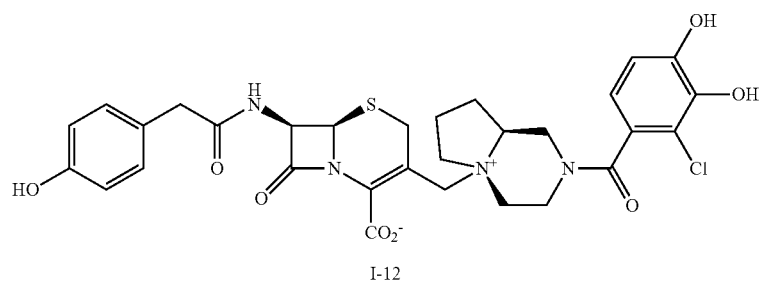

I-12

Step (1): Compound 12a+Compound 12b→Compound 12c
Compound 12a (1.08 g, 1.00 mmol) and compound 12b (152 mg, 1.00 mmol) were used to synthesize the target compound in the same way as in Example 4.

Step (2): Compound 12c→Compound (I-12)
The total amount of compound 12c yielded was used to synthesize the target compound in the same way as in Example 4

Yield 153.1 mg, (21%)

$^1$H-NMR (DMSO-$d_6$) δ: 10.31 (1H, br s), 9.52 (1H, br s), 9.27 (1H, br s), 8.97 (1H, d, J=8.39 Hz), 7.06-7.02 (2H, m), 6.82 (1H, d, J=8.24 Hz), 6.68-6.62 (3H, m), 5.54-5.50 (1H, m), 5.18-4.98 (2H, m), 4.32-3.44 (11H, m), 1.88-2.27 (5H, m).

Elemental analysis for: C30H31ClN4O8S(H2O)2.9
Calcd.: C, 51.82; H, 5.33; Cl, 5.10; N, 8.06; S, 4.61(%).
Found.: C, 51.81; H, 5.31; Cl, 5.11; N, 8.15; S, 4.63(%).

Example 13

Synthesis of Compound (I-13)

[Formula 69]

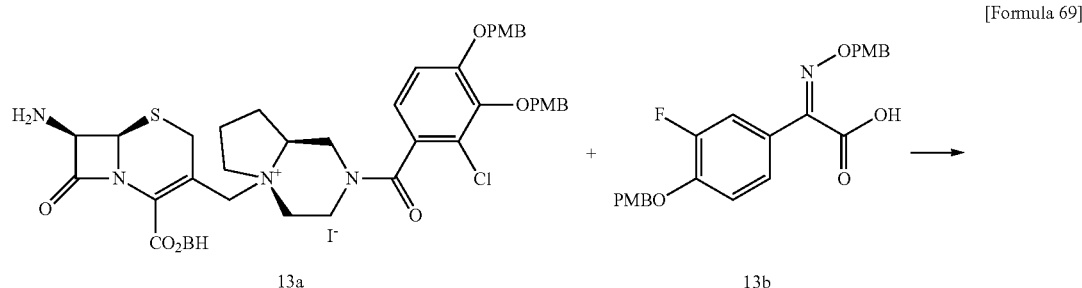

13a                13b

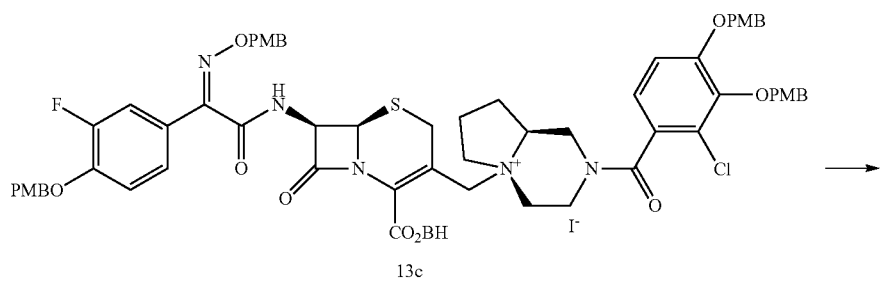

13c

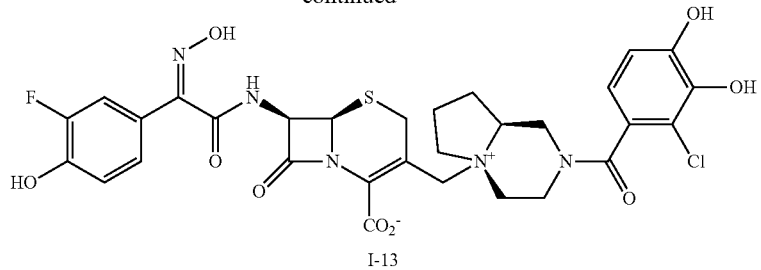

I-13

Step (1): Compound 13a+Compound 13b→Compound 13c

Compound 13a (1.08 g, 1.00 mmol) and compound 13b (439 mg, 1.00 mmol) were used to synthesize the target compound in the same way as in Example 4.

Step (2): Compound 13c→Compound (I-13)

The total amount of compound 13c yielded was used to synthesize the target compound in the same way as in Example 4.

Yield 172.3 mg, (19%)

$^1$H-NMR (DMSO-$d_6$) δ: 11.45 (1H, br s), 10.43 (1H, br s), 10.25 (1H, br s), 9.60-9.42 (2H, m), 7.27-7.13 (2H, m), 6.98 (1H, t, J=8.31 Hz), 6.83-6.62 (3H, m), 5.72-5.69 (1H, m), 5.15-5.02 (2H, m), 3.90-3.45 (11H, m), 2.27-1.85 (5H, m).

Elemental analysis for: C30H29ClFN5O9S(H2O)3.5

Calcd.: C, 47.84; H, 4.82; Cl, 4.71; F, 2.52; N, 9.30; S, 4.26(%).

Found.: C, 47.86; H, 4.73; Cl, 4.73; F, 2.53; N, 9.29; S, 4.42(%).

Example 14

Synthesis of Compound (I-14)

[Formula 70]

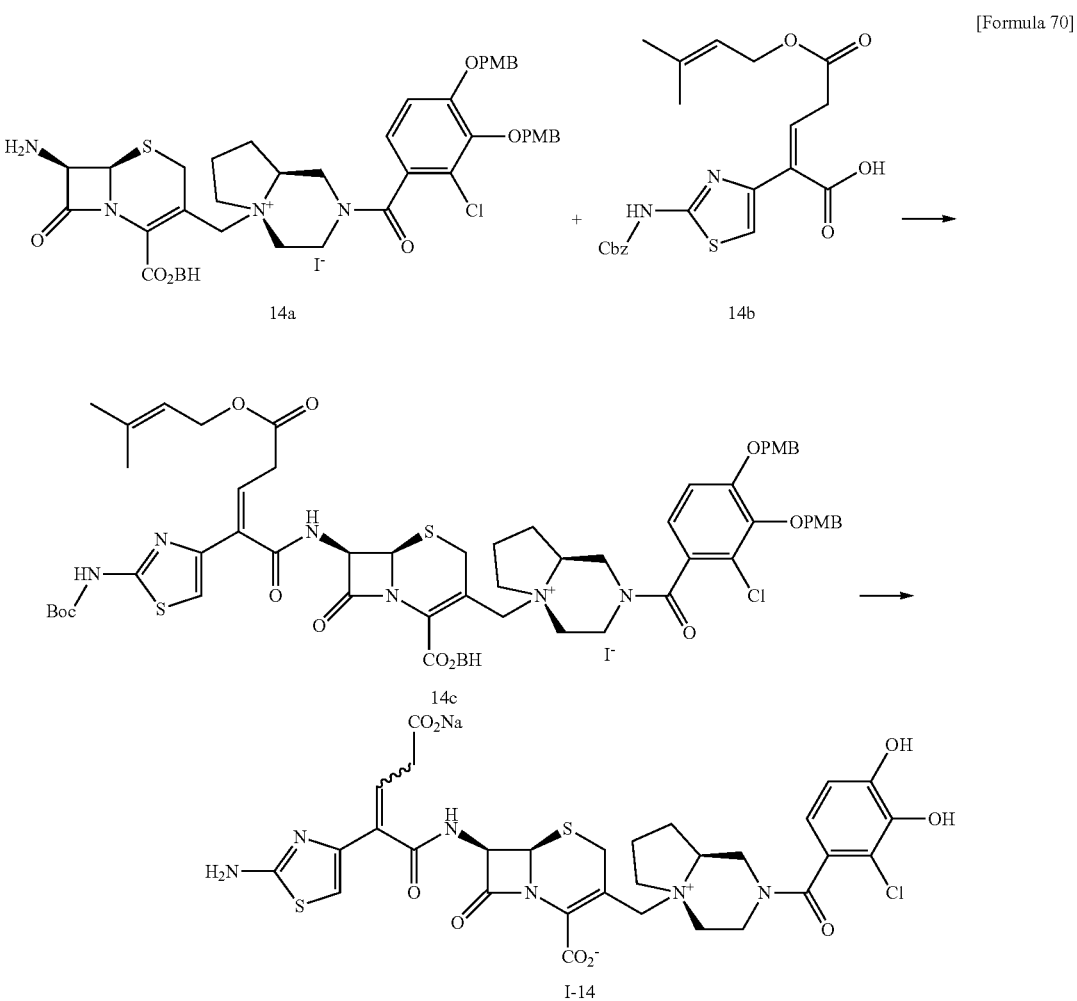

I-14

Step (1): Compound 14a+Compound 14b→Compound 14c

Compound 14a (1.08 g, 1.00 mmol) and compound 14b (430 mg, 1.00 mmol) were used to synthesize the target compound in the same way as in Example 4.

Step (2): Compound 14c→Compound (I-14)

The total amount of compound 14c yielded was used to synthesize the target compound in the same way as in Example 4.

Yield 96.9 mg, (11%)

$^1$H-NMR (D$_2$O) δ: 6.96-6.47 (4H, m), 5.87-5.77 (1H, m), 5.37-5.27 (1H, m), 4.41-4.23 (1H, m), 3.98-3.21 (12H, m), 2.87 (1H, s), 2.50-2.04 (5H, m).

Elemental analysis for: C30H30ClN6O9S2Na(H2O)5.2

Calcd.: C, 43.16; H, 4.88; Cl, 4.25; N, 10.07; S, 7.68; Na, 2.75(%).

Found.: C, 43.09; H, 4.90; Cl, 4.18; N, 10.26; S, 7.80; Na, 2.28(%).

Example 15

Synthesis of Compound (I-15)

Step (1): Compound 15a+Compound 15b→Compound 15c

Compound 15a (1.08 g, 1.00 mmol) and compound 15b (413 mg, 1.00 mmol) were used to synthesize the target compound in the same way as in Example 4.

Step (2): Compound 15c→Compound (I-15)

The total amount of compound 15c yielded was used to synthesize the target compound in the same way as in Example 9.

Yield 48.0 mg, (5%)

$^1$H-NMR (D$_2$O) δ: 7.54 (2H, d, J=8.85 Hz), 6.98-6.82 (4H, m), 5.91 (1H, d, J=4.92 Hz), 5.37 (1H, dd, J=8.01, 4.92 Hz), 4.33 (1H, d, J=12.81 Hz), 3.97-3.44 (11H, m), 2.02-2.50 (5H, m), 1.51 (6H, s).

Elemental analysis for: C34H35ClN5O11SNa(H2O)5.1

Calcd.: C, 46.83; H, 5.22; Cl, 4.07; N, 8.03; S, 3.68; Na, 2.64(%).

Found.: C, 46.79; H, 5.25; Cl, 4.21; N, 8.13; S, 3.78; Na, 2.24(%).

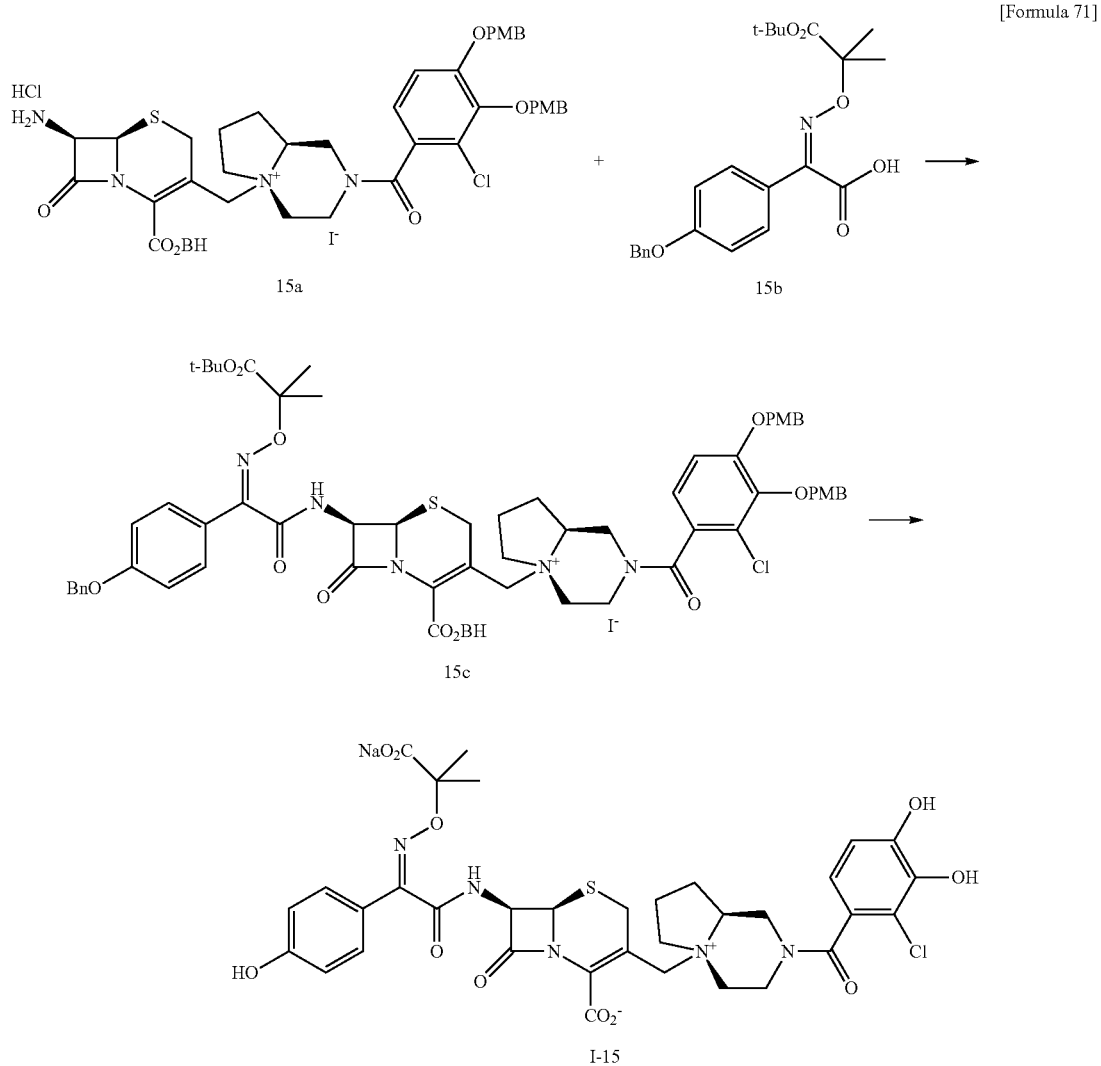

Example 16
Synthesis of Compound (I-16)
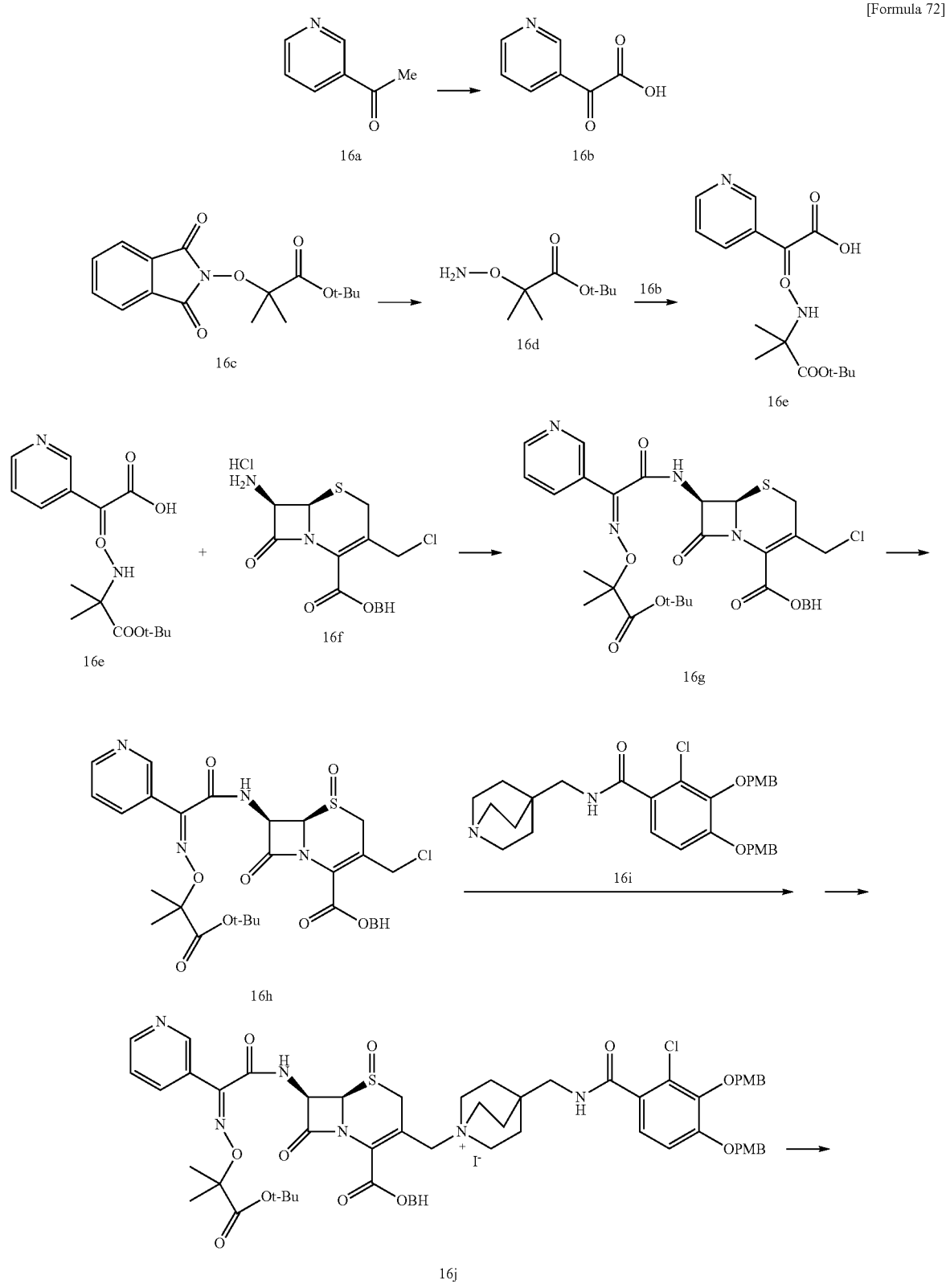

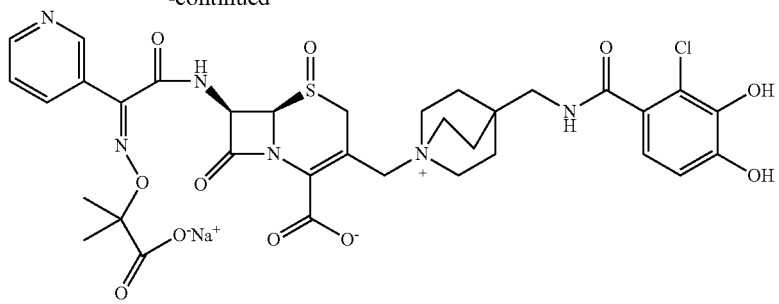

I-16

Step (1): Compound 16a→Compound 16b

To a solution of 16a (1.85 g) in pyridine (18 mL) was added selenium dioxide (4.16 g) and then the mixture was stirred at 80° C. for 6 hr. After cooled to r.t., the insoluble material was removed by filtration. The filtrate was concentrated. The residue containing compound 16b was used for the next step without further purification.

Step (2): Compound 16c+Compound 16d→Compound 16e

To a solution of compound 16c (4.58 g) in dichloromethane (17 mL) was added methylhydrazine (0.76 g) and then the mixture was stirred for 30 min. The precipitated material was removed by filtration. The filtrate was concentrated. To the residue was added MeOH (35 mL) and a solution of compound 16b as prepared above in MeOH was added. The mixture was stirred at r.t. for 3 hr. The mixture was diluted with ethyl acetate and water. The pH of the aqueous layer was adjusted to 3 with hydrochloric acid. The organic layer was washed with brine, dried over magnesium sulfate and concentrated to afford compound 16e (4.2 g), which was used for the next step without further purification.

Step (3): Compound 16e+Compound 16f→Compound 16g

To a solution of compound 16e (4.2 g) prepared above in ethyl acetate was added compound 16f (6.77 g), and were added phenyl dichlorophosphate (5.74 g) and then N-methylmorphorine (7.59 g) at −40° C. The mixture was stirred at −40° C. for 1 hr. A 10% aqueous solution of citric acid was added. The organic layer was washed with water and brine, dried over magnesium sulfate and concentrated. The residue was purified by column chromatography on silica gel (n-hexane/ethyl acetate) to afford compound 16g (3.74 g, 35% yield in 4 steps).

$^1$H-NMR (CDCl$_3$) δ: 8.84 (1H, d, J=1.17 Hz), 8.63 (1H, dd, J=4.87, 1.80 Hz), 7.89 (1H, dt, J=8.06, 1.80 Hz), 7.47-7.30 (12H, m), 7.00 (1H, s), 5.98 (1H, dd, J=9.74, 5.04 Hz), 5.06 (1H, d, J=5.04 Hz), 4.46 (1H, d, J=11.83 Hz), 4.40 (1H, d, J=11.83 Hz), 3.69 (1H, d, J=18.46 Hz), 3.53 (1H, d, J=18.46 Hz), 1.54 (3H, s), 1.52 (3H, s), 1.47 (9H, s).

Step (4): Compound 16g→Compound 16h

To a solution of compound 16g (3.74 g) in dichloromethane was added a solution of m-chloroperbenzoic acid (1.55 g) in dichloromethane at −40° C. The mixture was stirred at same temperature for 1 hr. A 10% aqueous solution of sodium thiosulfate and ethyl acetate were added. Dichloromethane was removed by evaporation. The organic layer was washed with brine, dried over magnesium sulfate, filtered and concentrated. The residue was purified by column chromatography on silica gel (n-hexane/ethyl acetate) to afford compound 16h (2.77 g, 68% yield).

$^1$H-NMR (CDCl$_3$) δ: 8.85 (1H, dd, J=2.14, 0.76 Hz), 8.62 (1H, dd, J=4.88, 1.79 Hz), 8.14 (1H, d, J=10.60 Hz), 7.91 (1H, dt, J=8.03, 1.79 Hz), 7.47-7.29 (11H, m), 6.97 (1H, s), 6.20 (1H, dd, J=10.60, 4.88 Hz), 4.98 (1H, d, J=12.43 Hz), 4.59 (1H, dd, J=4.88, 1.37 Hz), 4.18 (1H, d, J=12.43 Hz), 3.85 (1H, d, J=18.53 Hz), 3.45 (1H, d, J=18.53 Hz), 1.55 (3H, s), 1.53 (3H, s), 1.47 (9H, s).

Step (5): Compound 16h→Compound (I-16)

Compound (I-16) was prepared in the same manner as described for the synthesis of the above products.

$^1$H-NMR (D$_2$O) δ: 8.65 (1H, s), 8.58 (1H, d, J=3.81 Hz), 8.03 (1H, dt, J=7.87, 1.87 Hz), 7.56 (1H, dd, J=7.87, 4.96 Hz), 6.92 (1H, d, J=8.31 Hz), 6.88 (1H, d, J=8.31 Hz), 5.74 (1H, d, J=5.03 Hz), 5.30 (1H, d, J=5.03 Hz), 4.60 (1H, d, J=13.88 Hz), 3.91 (1H, d, J=6.86 Hz), 3.86 (1H, d, J=9.76 Hz), 3.34-3.56 (9H, m), 1.95 (6H, t, J=7.55 Hz), 1.49 (3H, s), 1.48 (3H, s).

Elemental analysis for: C34H36ClN6O10SNa(H2O)9.0

Calcd.: C, 43.38; H, 5.78; Cl, 3.77; N, 8.93; S, 3.41; Na, 2.44(%).

Found.: C, 43.36; H, 5.60; Cl, 3.86; N, 8.91; S, 3.43; Na, 2.60(%).

Example 17

Synthesis of Compound (I-17)

[Formula 73]

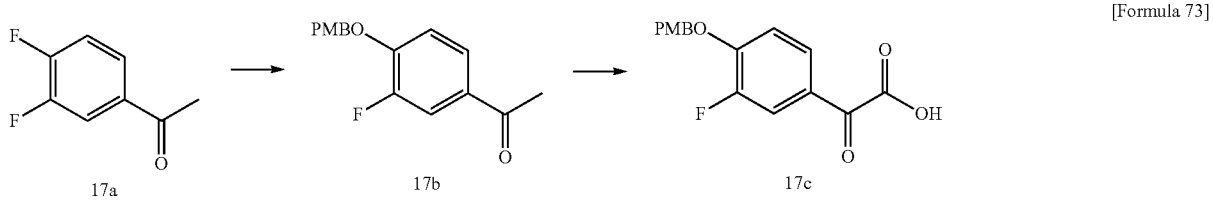

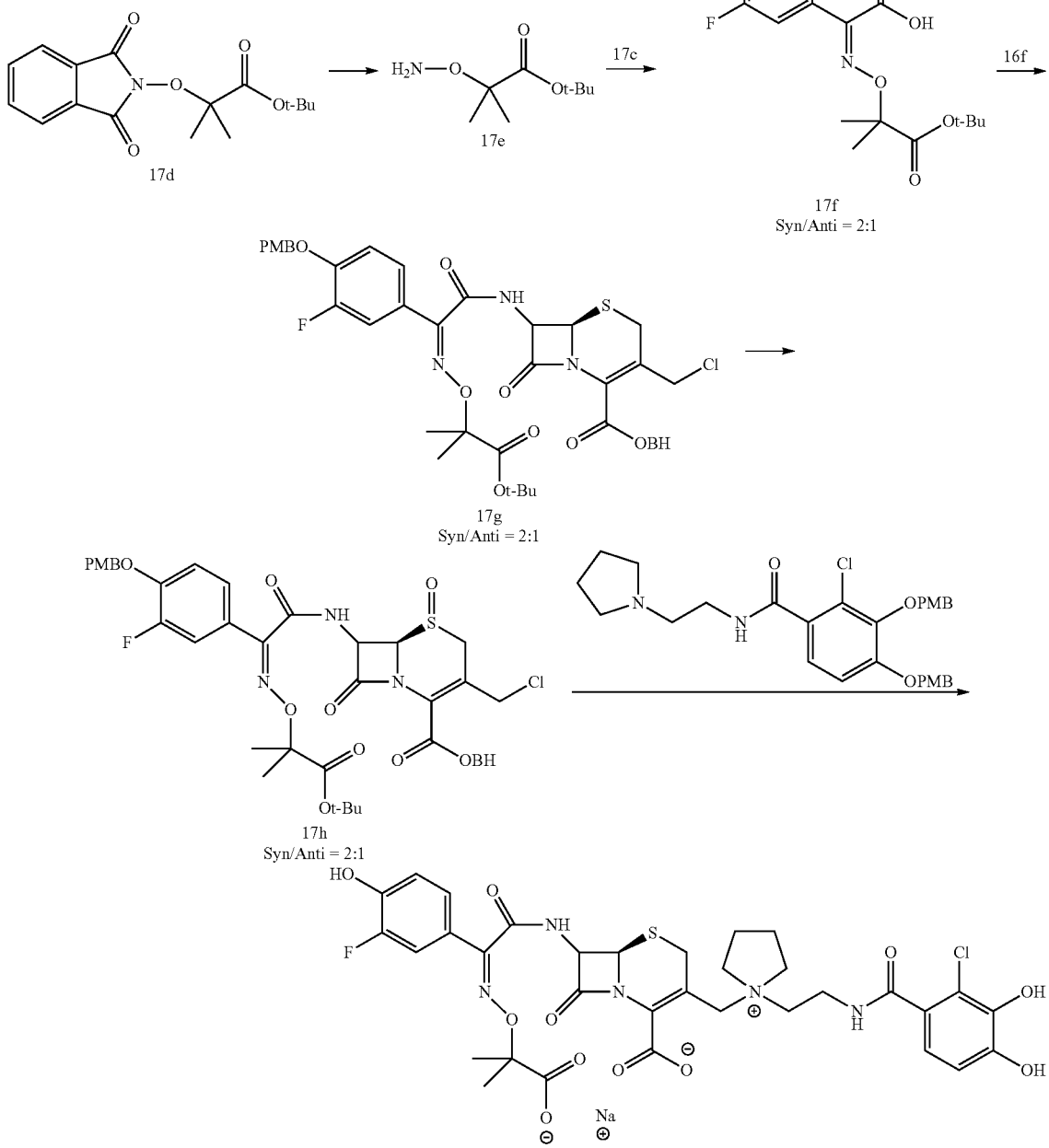

Step (1): Compound 17a→Compound 17b

To a mixture of compound 17a (25 g) and 4-methoxybenzyl alcohol (24.3 g) was added 18-crown-6 (4.23 g) and potassium carbonate (44.3 g). The mixture was stirred at 120° C. for 2 hr. The resulting mixture was diluted with ethyl acetate and iced water. The aqueous layer was extracted with ethyl acetate. The combined organic layers were dried over magnesium sulfate, filtered and concentrated. The residual solid was collected with diethyl ether by filtration and dried under in vacuo to afford compound 17b (36.0 g, 82% yield).

$^1$H-NMR (CDCl$_3$) δ: 7.67-7.72 (2H, m), 7.37 (2H, d, J=8.79 Hz), 7.04 (1H, t, J=8.38 Hz), 6.92 (2H, d, J=8.79 Hz), 5.14 (2H, s), 3.82 (3H, s), 2.54 (3H, s).

Step (2): Compound 17b→Compound 17c

To a solution of compound 17b (32.0 g) in pyridine (200 mL) was added selenium dioxide (25.9 g) and then the mixture was stirred at 80° C. for 3 hr. Further selenium dioxide (2.6 g) was added and the mixture was stirred at 80° C. for 4 hr. The insoluble material was removed by filtration. The residue was diluted with ethyl acetate and 2 mol/L hydrochloric acid. The organic layer was washed with water and brine, dried over magnesium sulfate, filtered, evaporated and dried in vacuo to afford compound 17c (34 g, 96% yield).

$^1$H-NMR (DMSO-$d_6$) δ: 7.71-7.79 (2H, m), 7.48 (1H, t, J=8.62 Hz), 7.42 (2H, d, J=8.54 Hz), 6.96 (2H, d, J=8.54 Hz), 5.23 (2H, s), 3.76 (3H, s).

Step (3): Compound 17c+Compound 17d→Compound 17f

Compound 17f was prepared as described in Example 16 from compound 17c (4.56 g) and compound 17d (4.58 g). Compound 17f was obtained as a mixture of geometric isomers and was used for the next step without further purification.

Step (4): Compound 17f+Compound 16f→Compound 17h

Compound 17h (6.0 g) was prepared as described in Example 16 from compound 17f (6.92 g) and compound 16f (6.77 g) via compound 17g. Compound 17h was obtained as a mixture of geometric isomers and was used for the next step without further purification.

Step (5): Compound 17h→Compound (I-17)

Compound (I-17) was prepared in the same manner as described for the synthesis of the above products.

$^1$H-NMR (D$_2$O) δ: 7.46 (1H, dd, J=12.28, 1.91 Hz), 7.26 (1H, dd, J=8.54, 2.14 Hz), 7.02 (1H, t, J=8.77 Hz), 6.95 (1H, d, J=8.31 Hz), 6.87 (1H, d, J=8.31 Hz), 5.88 (1H, d, J=4.88 Hz), 5.38 (1H, d, J=4.88 Hz), 4.14 (1H, d, J=14.18 Hz), 3.97-3.47 (10H, m), 2.23 (4H, br s), 1.52 (3H, s), 1.50 (3H, s).

Elemental analysis for: C33H34ClFN5O11SNa(H2O)7.8 (NaCl)0.1

Calcd.: C, 42.50; H, 5.36; Cl, 4.18; F, 2.04; N, 7.51; S, 3.44; Na, 2.71(%).

Found.: C, 42.44; H, 5.23; Cl, 4.33; F, 2.11; N, 7.57; S, 3.34; Na, 2.74(%).

Example 18

Synthesis of Compound (I-18)

[Formula 74]

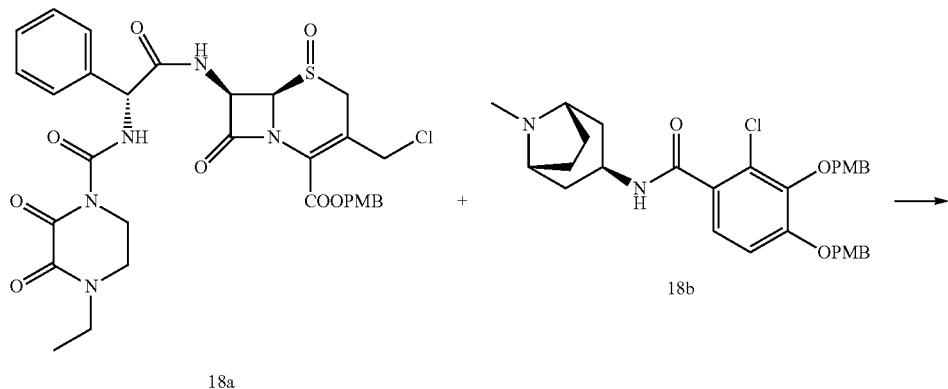

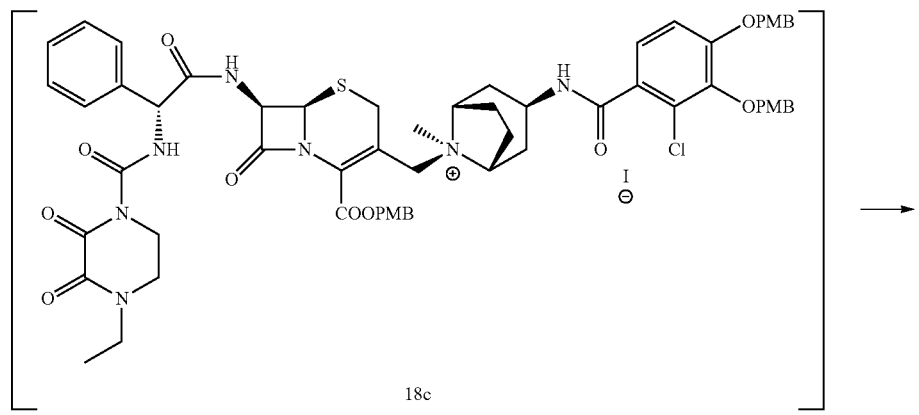

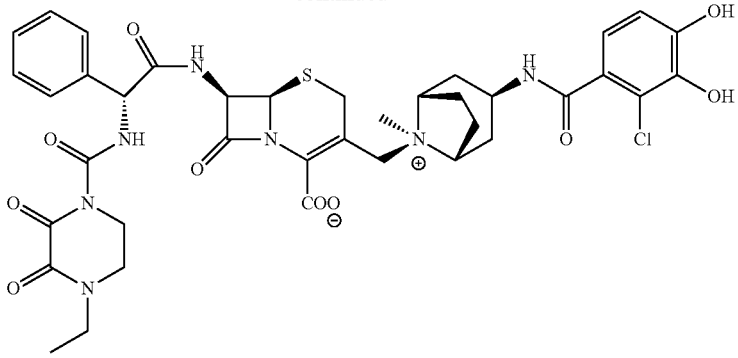

I-18

Step: Compound 18a+Compound 18b→Compound 18c→Compound (I-18)

A solution of compound 18b (441 mg, 0.80 mmol) in dimethylacetoamide (1.5 mL) was cooled to 15° C., and thereto was added compound 18a (549 mg, 0.80 mmol). The reaction vessel was then degassed under reduced pressure. Thereto was added sodium iodide (240 mg, 1.6 mmol), and the solution was stirred at 15° C. for 6 hours. Dimethylformamide (4.5 mL) was added thereto, and the solution was cooled to −40° C. Thereto was added phosphorus tribromide (151 μL, 1.6 mmol), and the solution was stirred at −40° C. for 30 minutes. The reaction mixture was slowly added to 5% sodium chloride solution. The precipitated solid was collected by filtration, washed with water, and suspended into water. The suspension was freeze-dried to yield compound 18c as a brown solid. Compound 18c yielded was used in the next reaction without further purification.

The total amount of compound 18c yielded was dissolved in dichloromethane (10 mL), and the solution was cooled to −40° C. Thereto were then added anisole (847 μL, 8 mmol) and 2 mol/L aluminum chloride solution (4.0 mL, 8 mmol) in nitromethane in turn. The reaction mixture was stirred at 0° C. for 30 minutes. To the reaction mixture were added diisopropyl ether and a small amount of water, and the resultant was stirred to generate a precipitate. The supernatant was removed by decantation. To the insoluble material adhering to the vessel were added a diluted aqueous hydrochloric acid solution and acetonitrile to dissolve the material completely. Thereto was then added diisopropyl ether, and the aqueous layer was separated. The organic layer was again subjected to extraction with water, and then all of the resultant aqueous layers were combined. Thereto was added HP20SS resin. Acetonitrile was evaporated under reduced pressure. The resultant mixed liquid was purified by ODS column chromatography. The fractions containing desired compound were collected and concentrated under reduced pressure, and then freeze-dried to yield compound (I-18) as a white powder.

Yield 390 mg, (59%)

$^1$H-NMR (DMSO-$d_6$) δ: 1.08 (3H, t, J=7.2 Hz), 1.91-1.98 (2H, m), 2.30-2.53 (6H, m), 2.95 (3H, s), 3.53-4.00 (12H, m), 4.84 (1H, d, J=12.2 Hz), 4.99 (1H, d, J=5.0 Hz), 5.58-5.65 (2H, m), 6.70 (1H, d, J=8.2 Hz), 6.77 (1H, d, J=8.2 Hz), 7.29-7.44 (5H, m), 8.32 (1H, d, J=3.8 Hz), 9.46 (1H, d, J=8.2 Hz), 9.85 (1H, d, J=7.6 Hz).

MS (m+1)=824.44

Elemental analysis for: C38H42ClN7O10S.5.0H2O
Calcd.: C, 49.91; H, 5.73; Cl, 3.88; N, 10.72; S, 3.51(%).
Found.: C, 49.95; H, 5.65; Cl, 4.09; N, 10.61; S, 3.55(%).

Example 19

Synthesis of Compound (I-19)

[Formula 75]

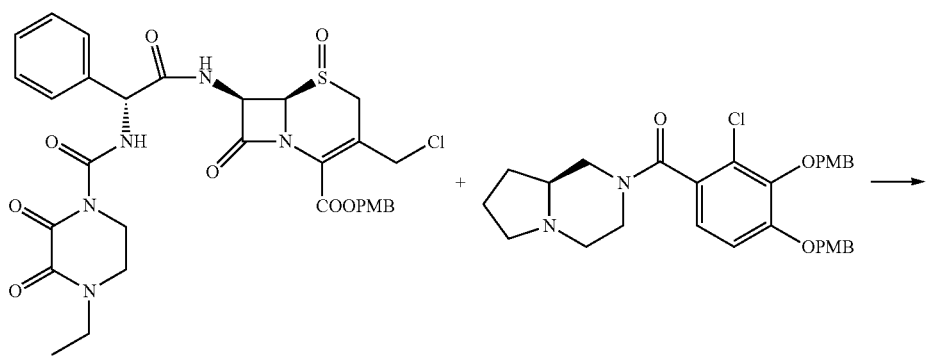

18a        19a

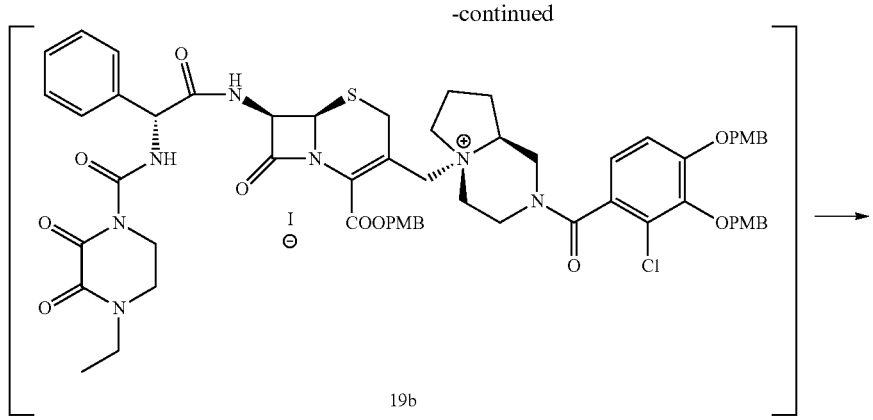

19b

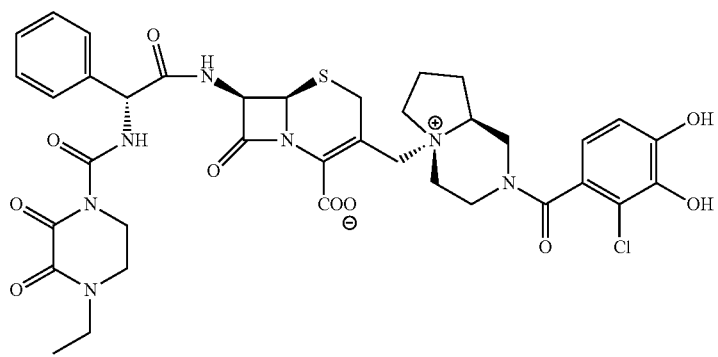

I-19

Step: Compound 18a+Compound 19a→Compound 19b→Compound (I-19)

From compound 18a (549 mg, 0.80 mmol) and compound 19a (430 mg, 0.80 mmol), compound (I-19) was obtained as a white powder using the same method as Example 18.

Yield 456 mg, (70%)

$^1$H-NMR (DMSO-d$_6$) δ: 1.08 (3H, t, J=7.1 Hz), 1.95-2.23 (4H, m), 3.53-4.25 (18H, m), 4.93-5.12 (2H, m), 5.57-5.65 (2H, m), 6.62 (1H, d, J=8.1 Hz), 6.82 (1H, d, J=8.1 Hz), 7.28-7.44 (5H, m), 9.46 (1H, d, J=5.5 Hz), 9.85 (1H, d, J=7.0 Hz).

MS (m+1)=810.30

Elemental analysis for: C37H40ClN7O10S.4.9H$_2$O

Calcd.: C, 49.46; H, 5.59; Cl, 3.95; N, 10.91; S, 3.57(%).

Found.: C, 49.41; H, 5.43; Cl, 3.97; N, 10.88; S, 3.59(%).

Example 20

Synthesis of Compound (I-20)

[Formula 76]

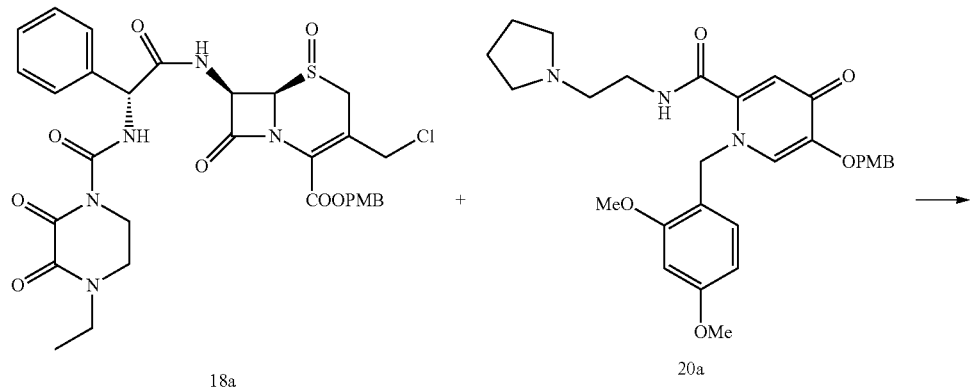

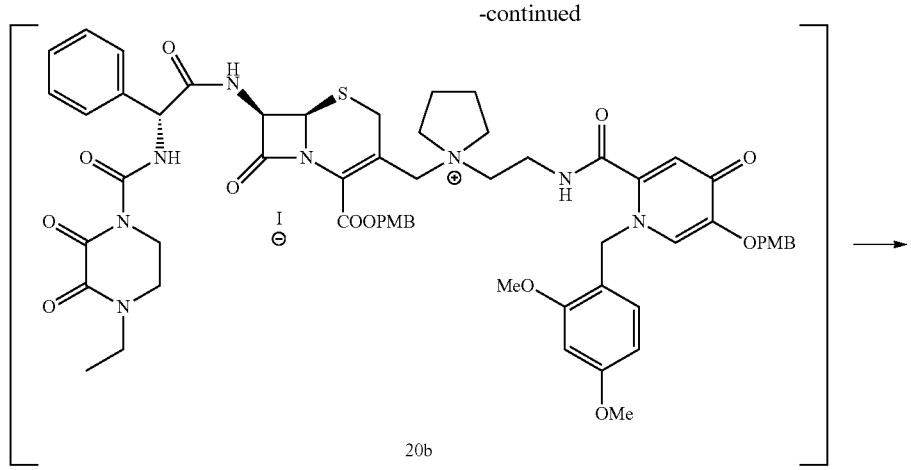
20b
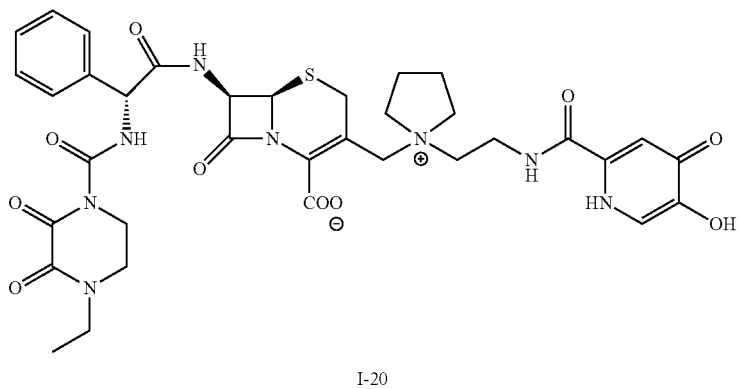
I-20
Step: Compound 18a+Compound 20a→Compound 20b→Compound (I-20)
From compound 18a (343 mg, 0.50 mmol) and compound 20a (261 mg, 0.50 mmol), compound (I-20) was obtained as a white powder using the same method as Example 18.
Yield 136 mg, (36%)
$^1$H-NMR (DMSO-d$_6$) δ: 1.08 (3H, t, J=7.1 Hz), 1.95-2.10 (4H, m), 3.47-3.93 (17H, m), 4.99-5.04 (2H, m), 5.58-5.66 (2H, m), 7.28-7.45 (5H, m), 7.97 (1H, s), 8.81 (1H, s), 9.46 (1H, d, J=8.1 Hz), 9.85 (1H, d, J=7.4 Hz).
MS (m+1)=765.33
Elemental analysis for: C35H40N8O10S.3.9H$_2$O
Calcd.: C, 50.34; H, 5.77; N, 13.42; S, 3.84(%).
Found.: C, 50.34; H, 5.64; N, 13.19; S, 3.75(%).
Example 21
Synthesis of Compound (I-21)
[Formula 77]
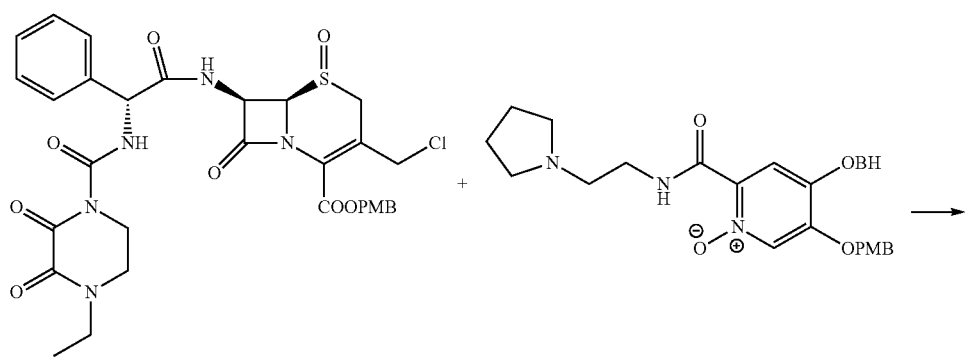
18a    21a -continued

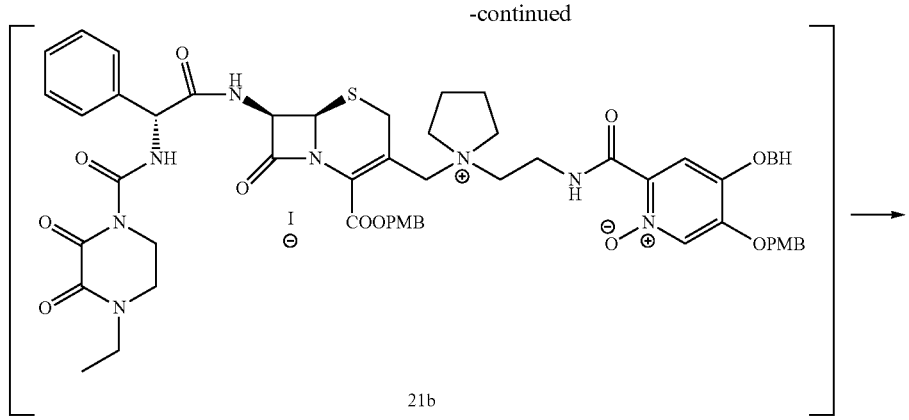

21b

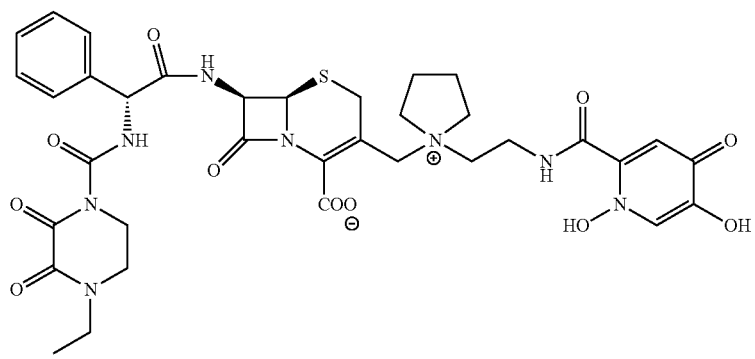

I-21

Step: Compound 18a+Compound 21a→Compound 21b→Compound (I-21)

A solution of compound 21a (221 mg, 0.40 mmol) in dimethylacetoamide (1 mL) was cooled to 15° C., and thereto was added compound 18a (274 mg, 0.40 mmol). The reaction vessel was then degassed under reduced pressure. Thereto was added sodium iodide (120 mg, 0.8 mmol), and the solution was stirred at 15° C. for 1 hour and stand overnight in refrigerator. Dimethylformamide (3.0 mL) was added thereto, and the solution was cooled to 0° C. Thereto was added potassium iodide (475 mg, 2.8 mmol) and acetyl chloride (114 μl, 1.6 mmol). The solution was stirred at 0° C. for 3 hours. The reaction mixture was slowly added to a 5% salt solution cooled with ice. The precipitated solid was collected by filtration, washed with water, and suspended into water. The suspension was freeze-dried to yield compound 21b as a brown solid. Compound 21b yielded was used in the next reaction without further purification.

The total amount of compound 21b yielded was dissolved in dichloromethane (6 mL), and the solution was cooled to −40° C. Thereto were then added anisole (437 μL, 8.0 mmol) and a 2 mol/L aluminum chloride solution (2.0 mL, 4.0 mmol) in nitromethane in turn. The reaction mixture was stirred at 0° C. for 30 minutes. To the reaction mixture were added diisopropyl ether and a small amount of water, and the resultant was stirred to generate a precipitate. The supernatant was removed by decantation. To the insoluble material adhering to the vessel were added a diluted aqueous hydrochloric acid solution and acetonitrile. The resultant was stirred to dissolve the material completely. Thereto was then added diisopropyl ether, and the aqueous layer was separated. The organic layer was again subjected to extraction with water, and then all of the resultant aqueous layers were combined. Thereto was added HP20SS resin. Acetonitrile was then evaporated under reduced pressure. The resultant mixed liquid was purified by ODS column chromatography. The fractions containing desired compound were collected and concentrated under reduced pressure, and then freeze-dried to yield compound (I-21) as a white powder.

Yield 73 mg, (23%)

$^1$H-NMR (DMSO-$d_6$) δ: 1.08 (3H, t, J=7.2 Hz), 1.96-2.07 (4H, br m), 3.38-4.03 (17H, m), 4.96-5.02 (2H, m), 5.61-5.65 (2H, m), 7.27-7.45 (5H, m), 7.51 (1H, s), 7.87 (1H, s), 9.49 (1H, d, J=8.2 Hz), 9.85 (1H, d, J=7.3 Hz), 11.80 (1H, s).

MS (m+1)=781.37

Elemental analysis for: $C_{35}H_{40}N_8O_{11}S·3.0H_2O$

Calcd.: C, 50.35; H, 5.55; N, 13.42; S, 3.84(%).

Found.: C, 50.44; H, 5.54; N, 13.17; S, 3.80(%).

Example 22
Synthesis of Compound (I-22)
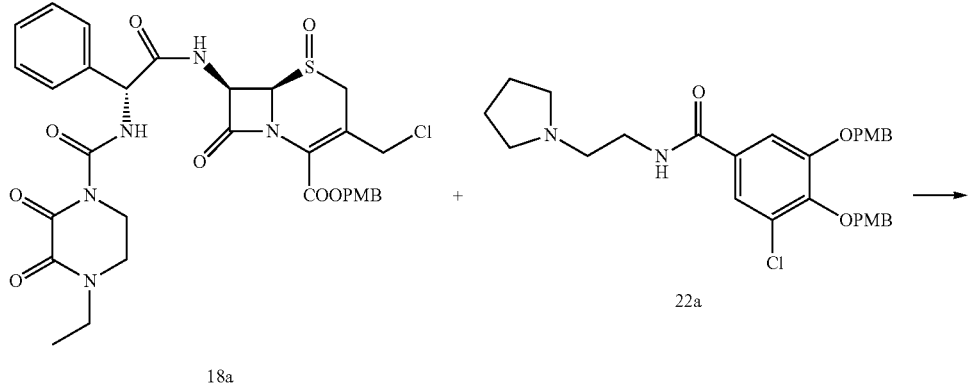
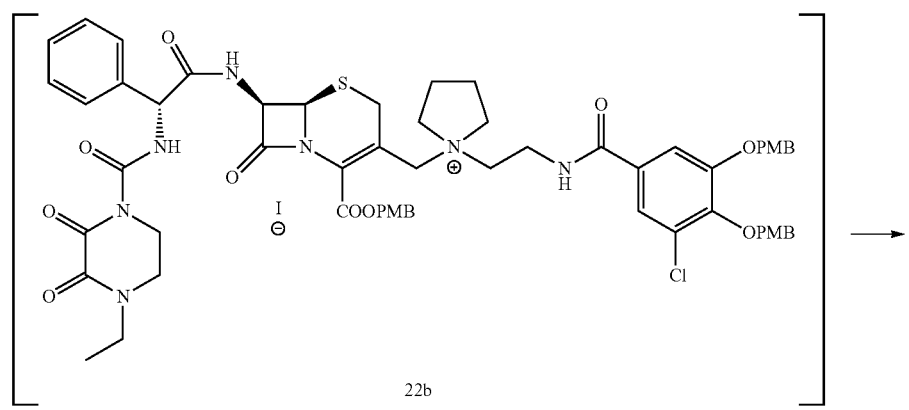
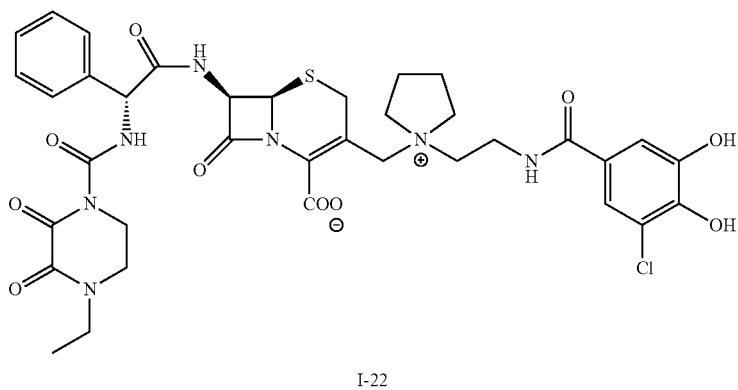
Step: Compound 18a+Compound 22a→Compound 22b→Compound (I-22)
From compound 18a (343 mg, 0.50 mmol) and compound 22a (263 mg, 0.50 mmol), compound (I-22) was obtained as a white powder using the same method as Example 18.
Yield 242 mg, (61%)
$^1$H-NMR (DMSO-$d_6$) δ: 1.08 (3H, t, J=7.1 Hz), 1.94-2.10 (4H, m), 3.23-3.91 (17H, m), 5.00 (1H, d, J=5.0 Hz), 5.06 (1H, d, J=13.4 Hz), 5.60-5.65 (2H, m), 7.28-7.44 (7H, m), 8.68 (1H, s), 9.48 (1H, d, J=8.4 Hz), 9.85 (1H, d, J=7.3 Hz).
MS (m+1)=798.39
Elemental analysis for: C36H40ClN7O10S.3.7H$_2$O
Calcd.: C, 49.99; H, 5.52; Cl, 4.10; N, 11.34; S, 3.71(%).
Found.: C, 49.99; H, 5.50; Cl, 4.48; N, 11.22; S, 3.67(%).

Example 23

Synthesis of Compound (I-23)

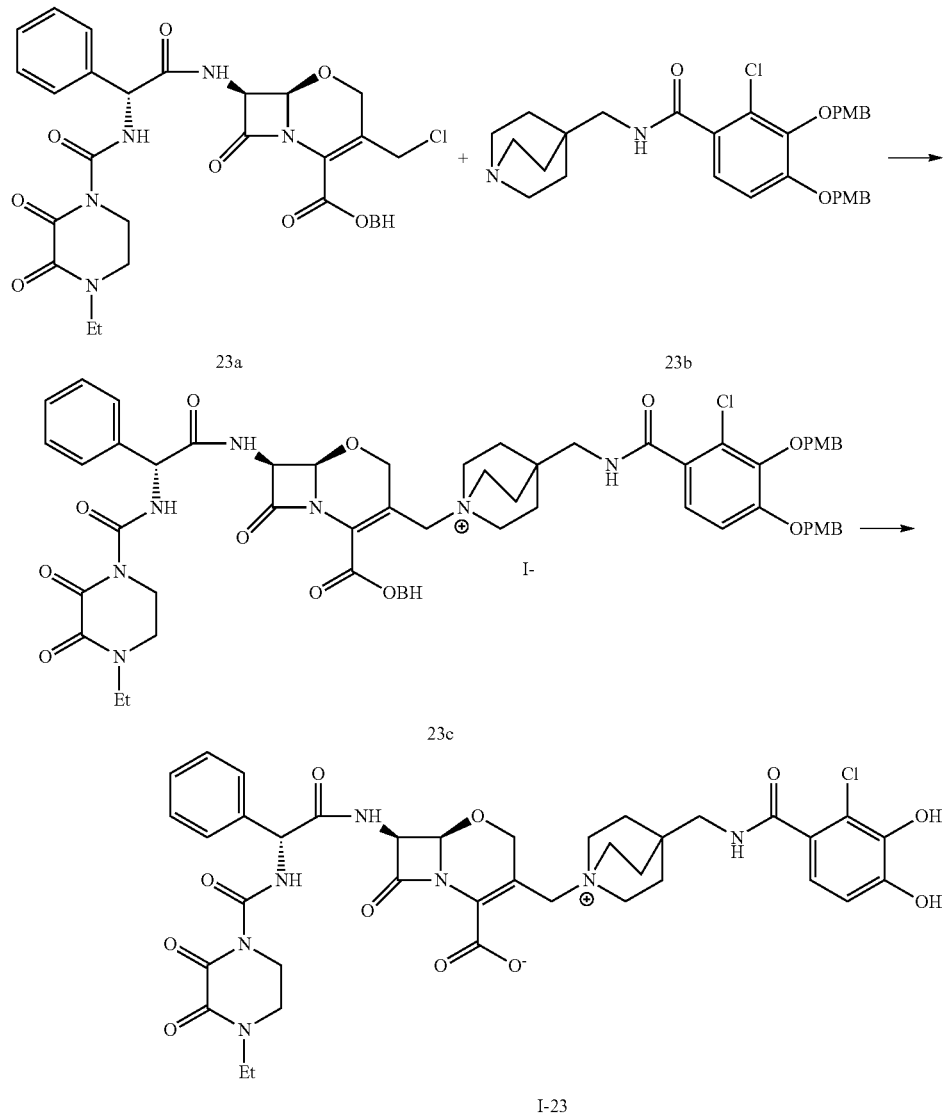

Step: Compound 23a+Compound 23b→Compound (I-23)

Compound 23a (0.35 g, 0.5 mmol) was dissolved in dimethylacetoamide (0.75 mL), and sodium iodide (0.15 g, 1 mmol) was added thereto, and the solution was stirred at −20° C. for 10 min. Compound 23b (0.248 g, 1 mmol) was added to the reaction mixture and stirred at −20° C. for 5 hours. The reaction mixture was slowly poured into an acidic 5% sodium chloride solution. The resultant residue was collected by filtration, washed with water, and then dried under reduced pressure to obtain compound 23c.

The compound 23c yielded was dissolved in dichloromethane, and the solution was cooled to −40° C. Thereto were then added anisole (1.09 mL, 10 mmol) and a 2 mol/L aluminum chloride solution (5 mL, 10 mmol) in nitromethane in turn. The reaction mixture was stirred at 0° C. To the reaction mixture were added water (30 mL) and diisopropyl ether (50 mL). Acetonitrile and 2 mol/L HCl aq. were added, and the resultant precipitate was dissolved, and then the aqueous layer was separated. The organic layer was extracted with water/acetonitrile/diluted hydrochloric acid. Then, the resultant aqueous layers were combined, added with HP20SS resin and concentrated. The resultant concentrated suspension was purified by HP20SS-ODS column chromatography. The fractions containing desired compound eluted with water-acetonitrile were concentrated under reduced pressure, and then freeze-dried to yield compound (I-23) as a powder.

(Yield 178 mg, 24%)

MS (m+1)=808.50

$^{1}$H-NMR (DMSO-$d_6$) δ: 9.85 (2H, d, J=7.6 Hz), 9.22 (1H, d, J=8.6 Hz), 8.30-8.20 (2H, brm), 7.53-7.23 (10H, m), 6.74 (3H, s), 5.67 (1H, d, J=7.6 Hz), 5.47-5.38 (1H, m), 5.07 (2H, d, J=4.2 Hz), 4.42 (1H, d, J=17.3 Hz), 4.19 (1H, d, J=15.9 Hz), 3.97-3.83 (4H, m), 3.11 (4H, d, J=5.0 Hz), 1.82-1.65 (9H, m), 1.08 (6H, t, J=7.1 Hz).

Elemental analysis:

Calcd.: C, 50.71; H, 5.85; N, 10.89; Cl, 3.94(%).

Found.: C, 50.58; H, 5.67; N, 11.15; Cl, 4.04(%).

The subject invention includes compounds of the following formulae (II-A), (II-B), (II-C), (II-D), (II-E), (II-F), (II-G), (II-H), (II-I), (II-J), (II-K), (II-L), (II-M), (II-N), (II-O), and (II-P):
[Formula 79]
(11-A)
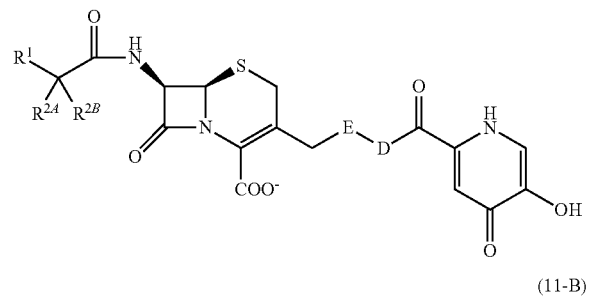
(11-B)
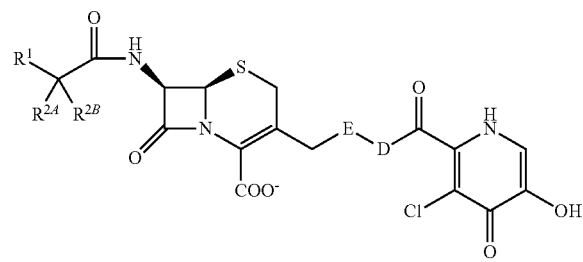
(11-C)
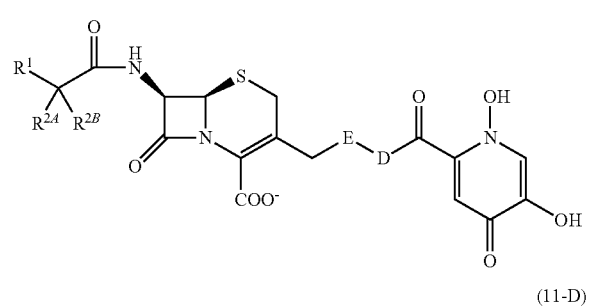
(11-D)
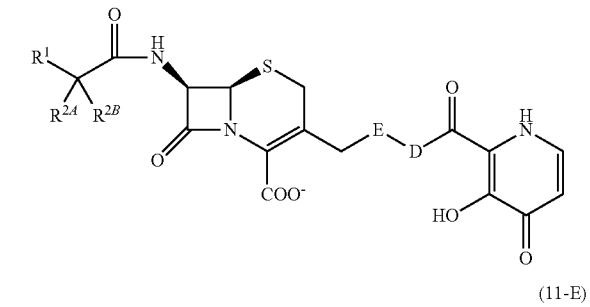
(11-E)
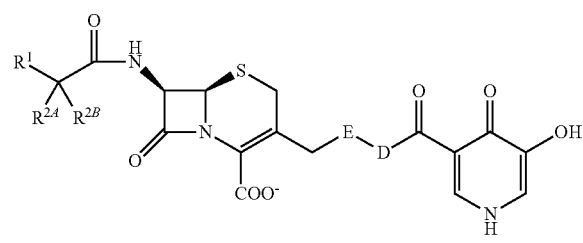
(11-F)
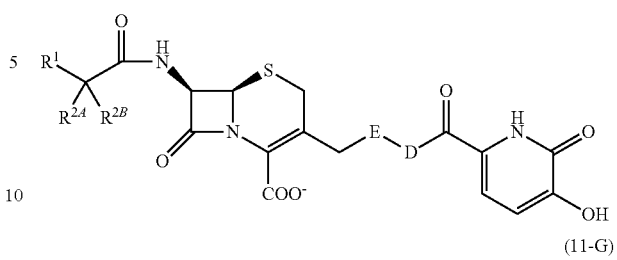
(11-G)
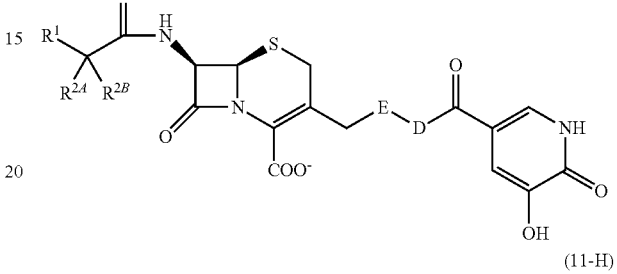
(11-H)
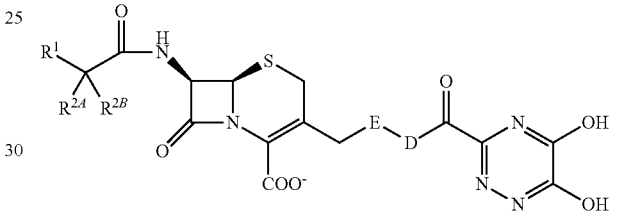
[Formula 80]
(11-I)
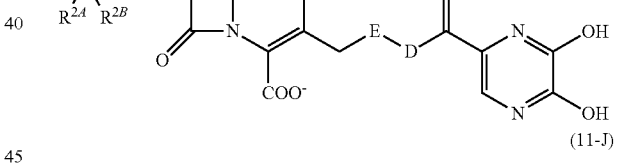
(11-J)
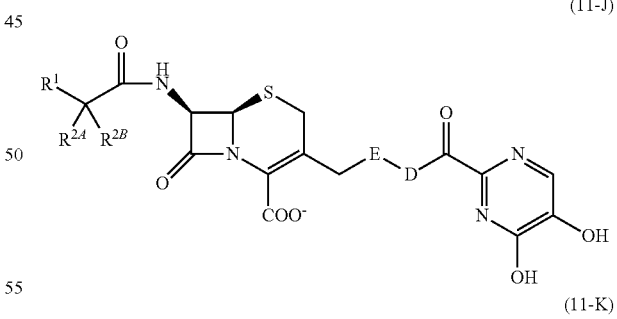
(11-K)
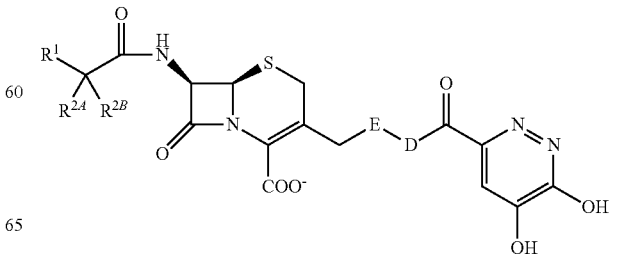

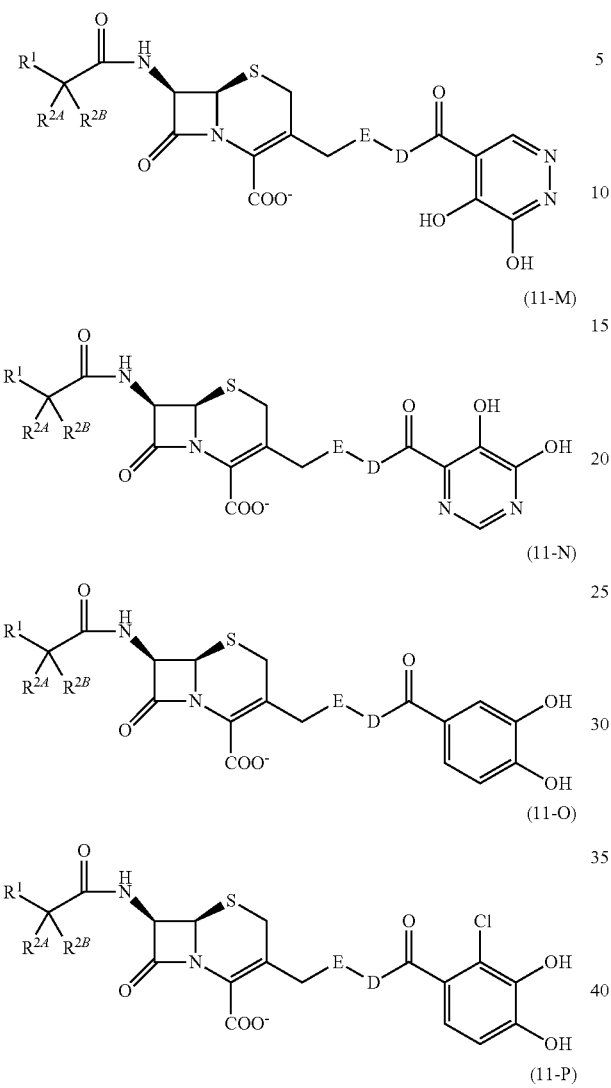
wherein R¹, R²ᴬ or R²ᴬ and R²ᴮ, and -E-D- are selected respectively from (R1-1) to (R1-6), (R2A-1) to (R2A-11) or (R2AB-1) to (R2AB-37), and (ED1) to (ED104) from the following Tables 1 to 10:
TABLE 1
 R1
TABLE 1-continued
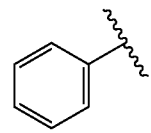 [SMILES: *c1ccccc1] R1-1
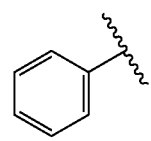 [SMILES: *c1ccccc1] R1-2
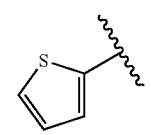 R1-3
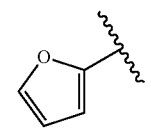 R1-4
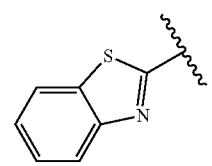 [SMILES: *c1nc2ccccc2s1] R1-5
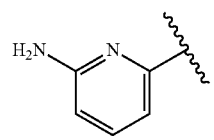 [SMILES: *c1cccc(N)n1] R1-6
TABLE 2
 R2A
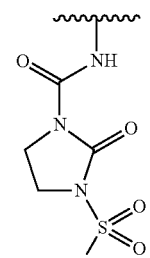 R2A-1
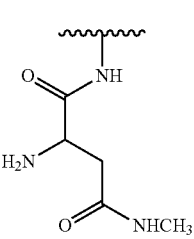 R2A-2

TABLE 2-continued
| | |
|---|---|
| 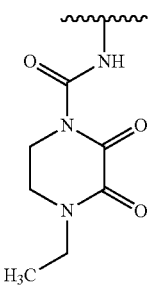 [SMILES: *NC(=O)N1CCN(CC)C(=O)C1=O] | R2A-3 |
| 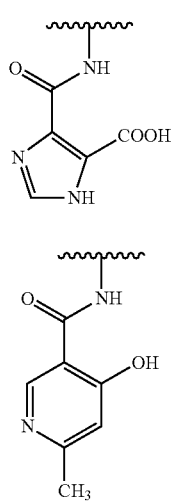 | R2A-4 |
| | R2A-5 |
| 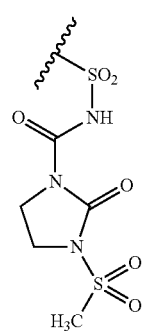 [SMILES: *S(=O)(=O)NC(=O)N1CCN(S(C)(=O)=O)C1=O] | R2A-6 |
| 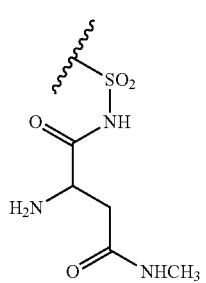 [SMILES: *S(=O)(=O)NC(=O)C(N)CC(=O)NC] | R2A-7 |
TABLE 2-continued
| | |
|---|---|
| 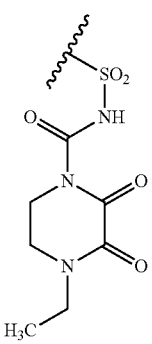 | R2A-8 |
| 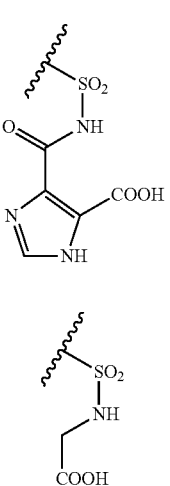 | R2A-9 |
| | R2A-10 |
| 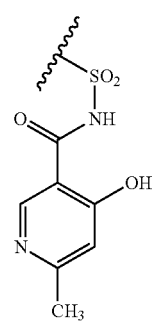 [SMILES: *S(=O)(=O)NC(=O)c1cnc(C)cc1O] | R2A-11 |
TABLE 3
| | |
|---|---|
| 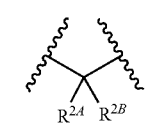 | R2AB |
| 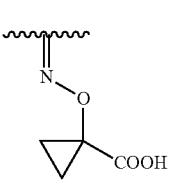 [SMILES: *=NOC1(C(=O)O)CC1] | R2AB-1 |

TABLE 3-continued
| | |
|---|---|
| 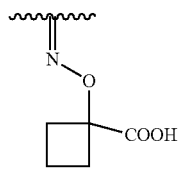 | R2AB-2 |
| 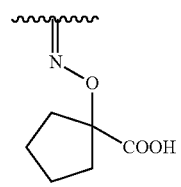 [SMILES: *=NOC1(C(=O)O)CCCC1] | R2AB-3 |
| 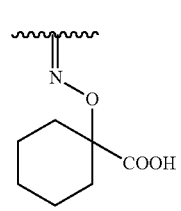 [SMILES: *=NOC1(C(=O)O)CCCCC1] | R2AB-4 |
| 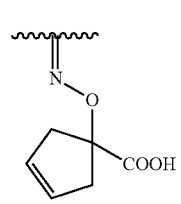 [SMILES: *=NOC1(C(=O)O)CC=CC1] | R2AB-5 |
| 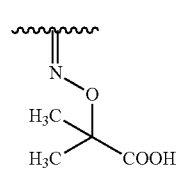 | R2AB-6 |
| 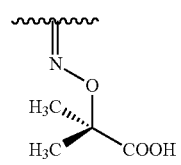 | R2AB-7 |
| 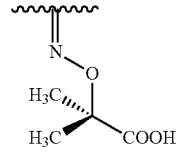 | R2AB-8 |
| 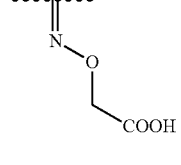 | R2AB-9 |
| 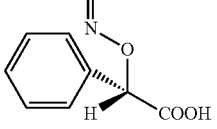 | R2AB-10 |
TABLE 3-continued
| | |
|---|---|
| 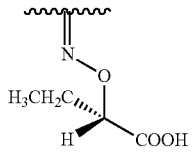 | R2AB-11 |
| 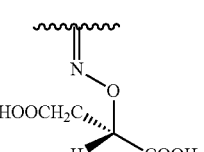 | R2AB-12 |
| 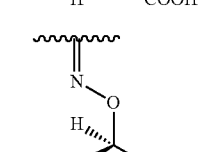 | R2AB-13 |
| 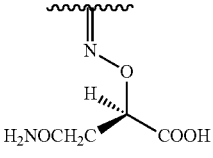 | R2AB-14 |
TABLE 4
| | |
|---|---|
| 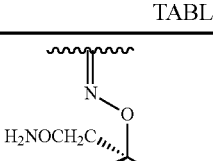 | R2AB-15 |
| 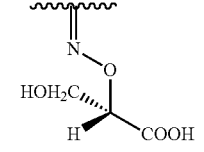 | R2AB-16 |
| 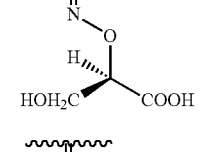 | R2AB-17 |
| 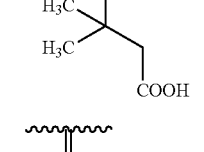 | R2AB-18 |
| 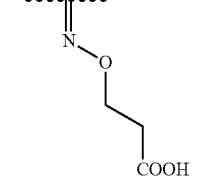 | R2AB-19 |

TABLE 4-continued
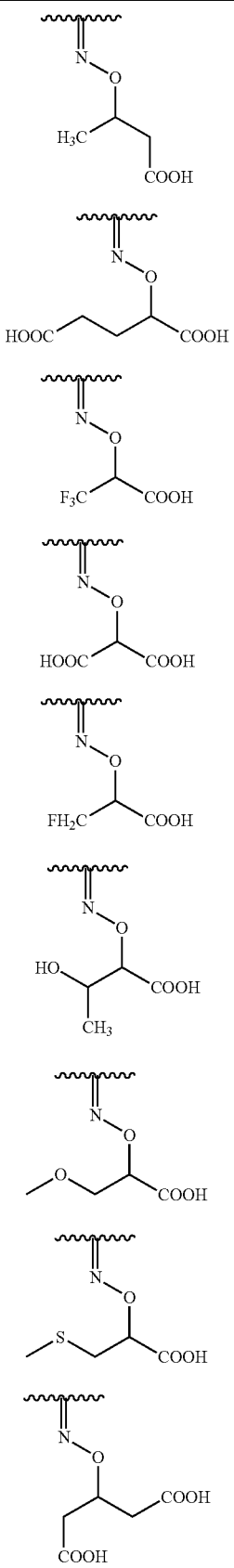
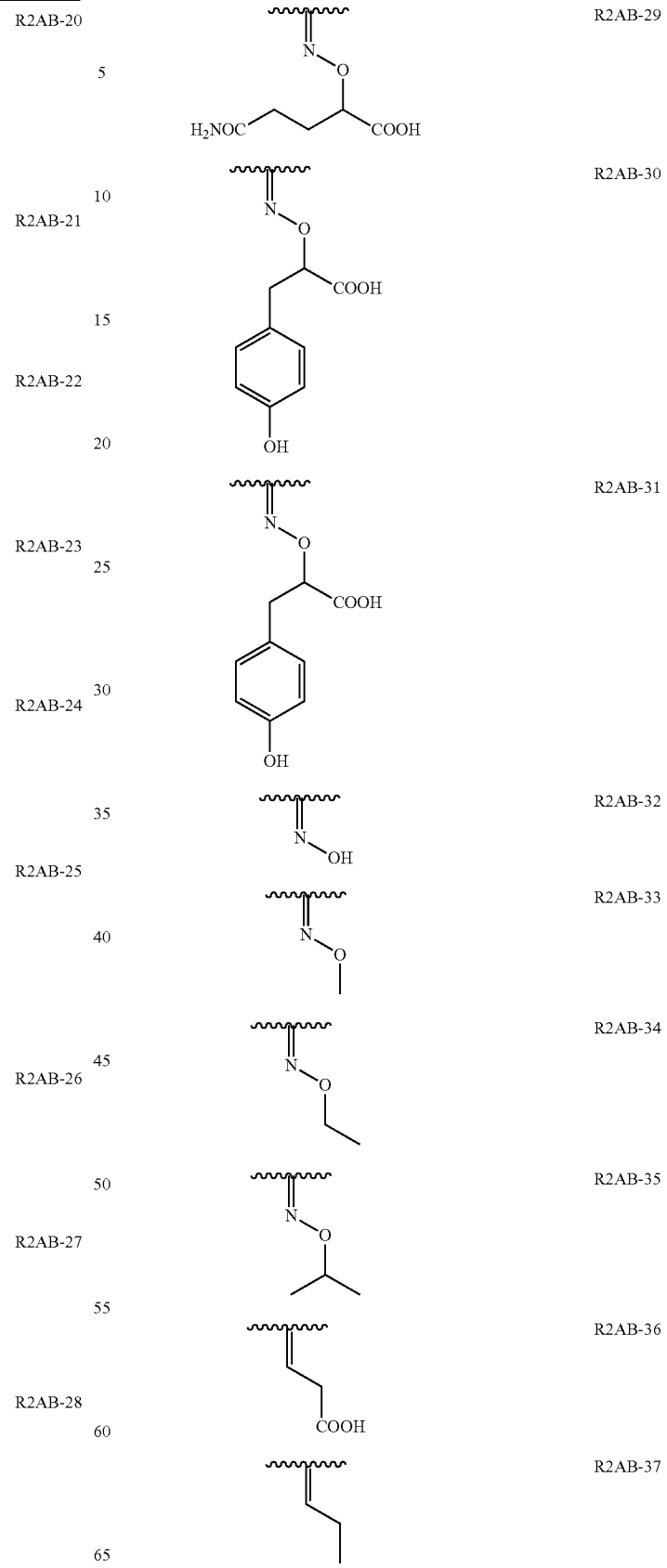

TABLE 5
| —E—D— |
|---|
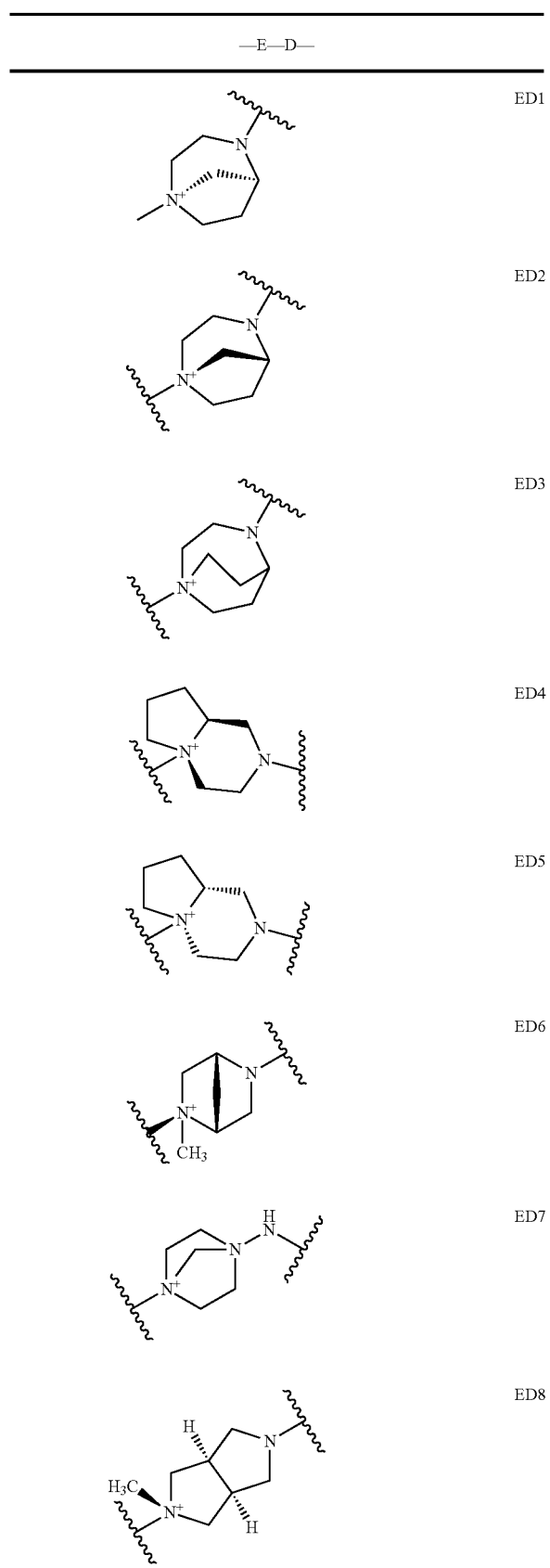
TABLE 5-continued
| —E—D— |
|---|
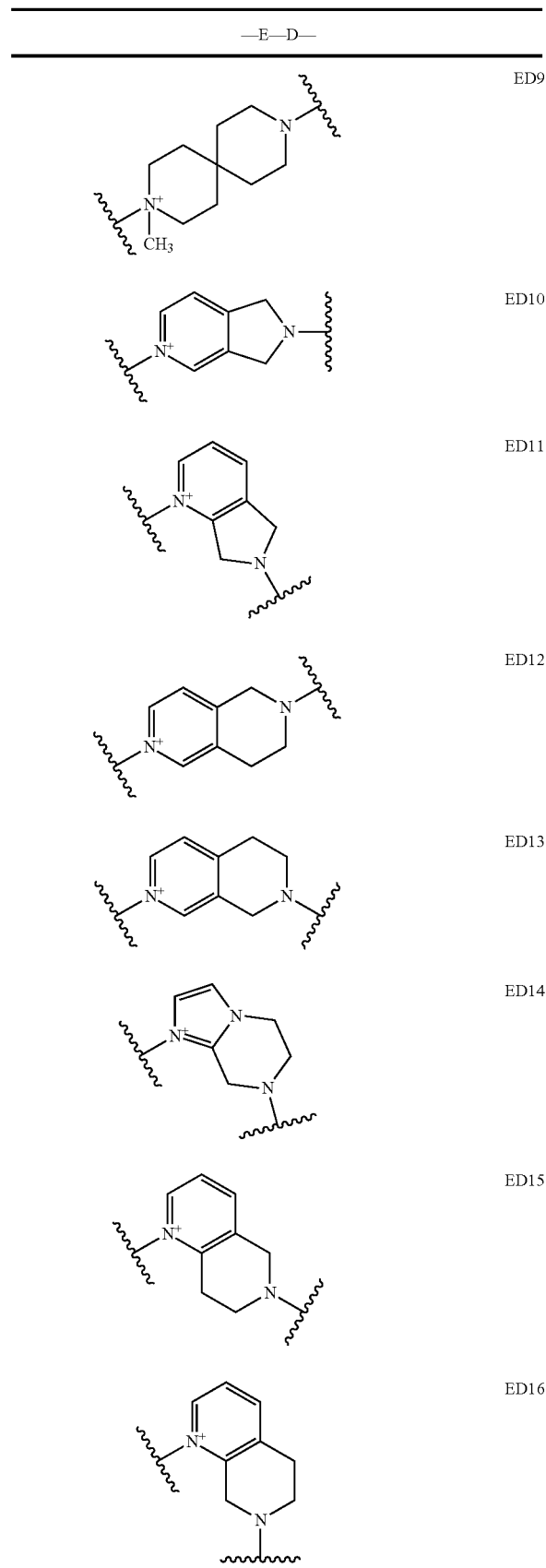

TABLE 5-continued
—E—D—
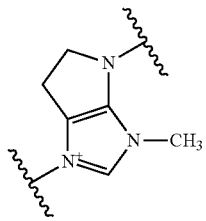 [SMILES: *N1CCc2c1n(C)c[n+]2*]
ED17
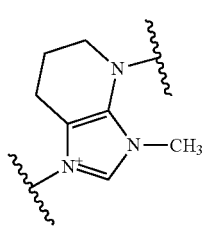 [SMILES: *N1CCCc2c1n(C)c[n+]2*]
ED18
TABLE 6
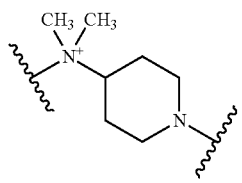 [SMILES: *N1CCC([N+](*)(C)C)CC1]
ED19
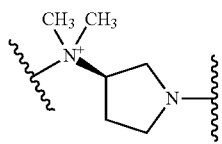 [SMILES: *N1CC[C@@H]([N+](*)(C)C)C1]
ED20
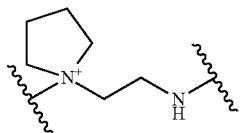 [SMILES: *NCC[N+]1(*)CCCC1]
ED21
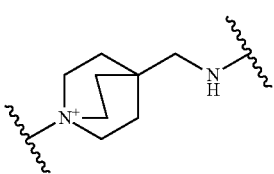 [SMILES: *NCC12CC[N+](*)(CC1)CC2]
ED22
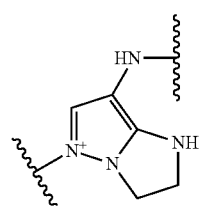 [SMILES: *Nc1c[n+](*)n2c1NCC2]
ED23
TABLE 6-continued
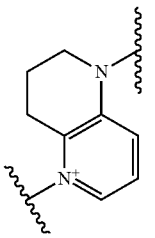 [SMILES: *N1CCCc2c1ccc[n+]2*]
ED24
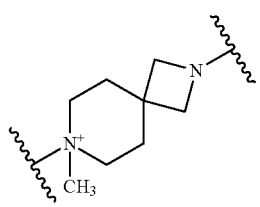 [SMILES: *N1CC2(CC[N+](*)(C)CC2)C1]
ED25
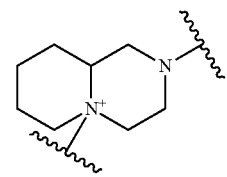 [SMILES: *N1CC[N+]2(*)CCCCC2C1]
ED26
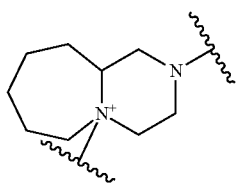 [SMILES: *N1CC[N+]2(*)CCCCCC2C1]
ED27
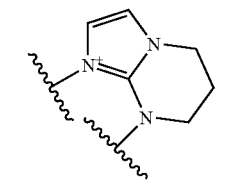 [SMILES: *N1CCCn2cc[n+](*)c21]
ED28
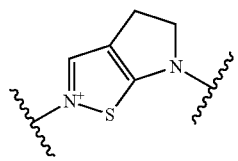 [SMILES: *N1CCc2c[n+](*)sc21]
ED29
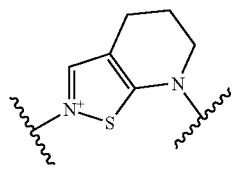 [SMILES: *N1CCCc2c[n+](*)sc21]
ED30
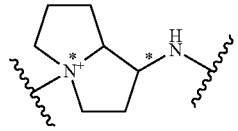 [SMILES: *NC1CC[N+]2(*)CCCC12]
ED31

TABLE 6-continued
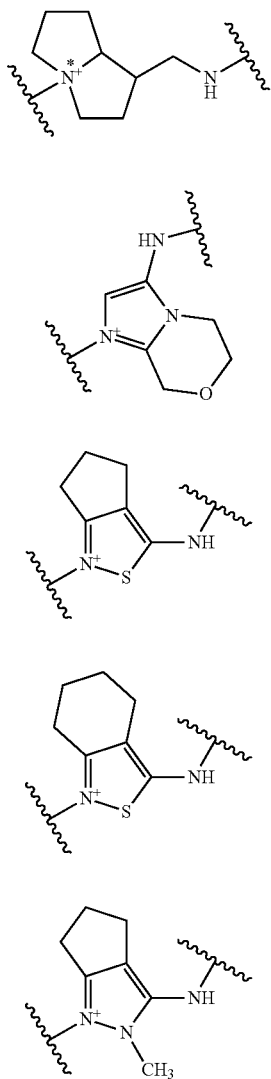
ED32
ED33
ED34
ED35
ED36
TABLE 7
TABLE 7-continued
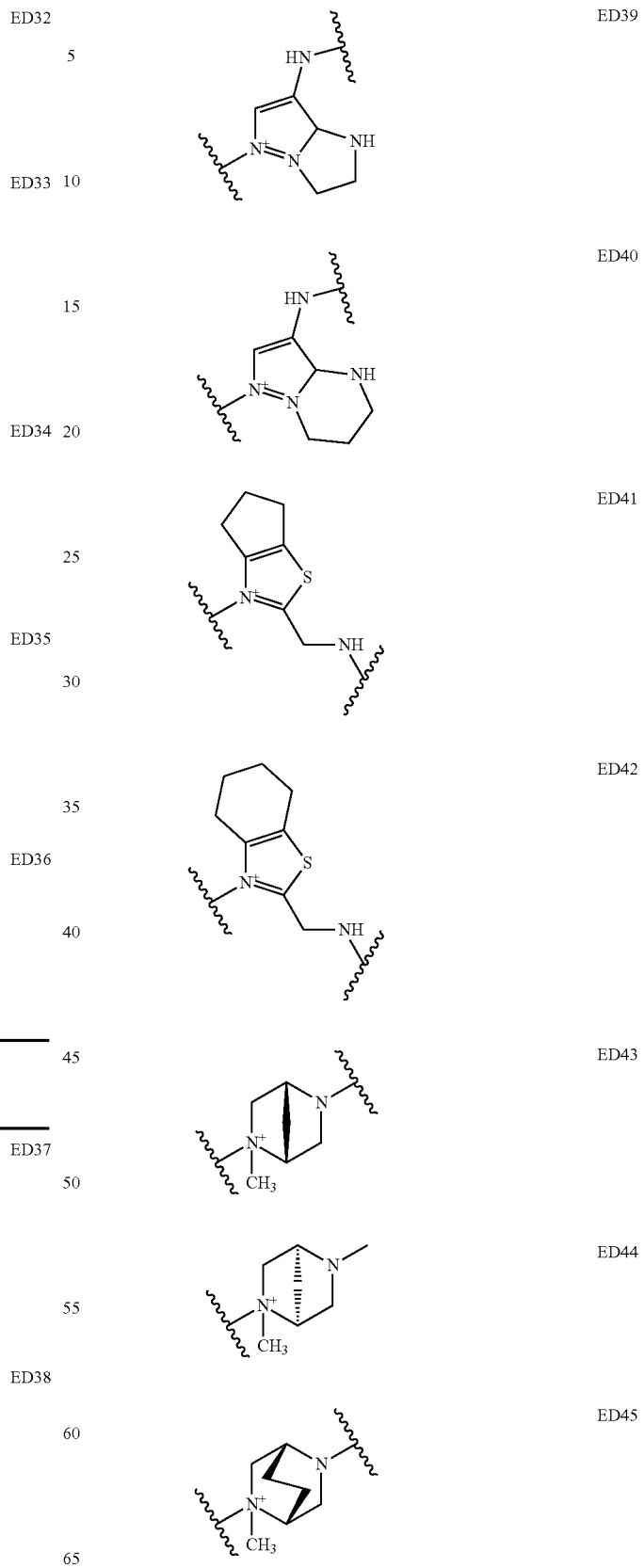
ED37
ED38
ED39
ED40
ED41
ED42
ED43
ED44
ED45

TABLE 7-continued
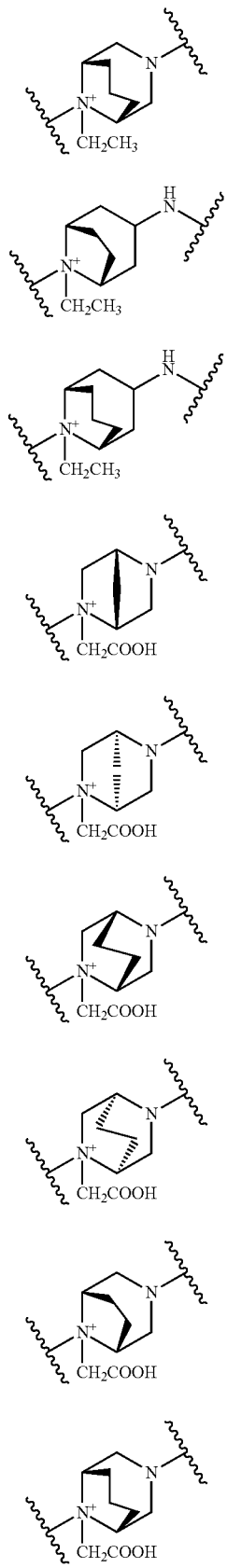
TABLE 8
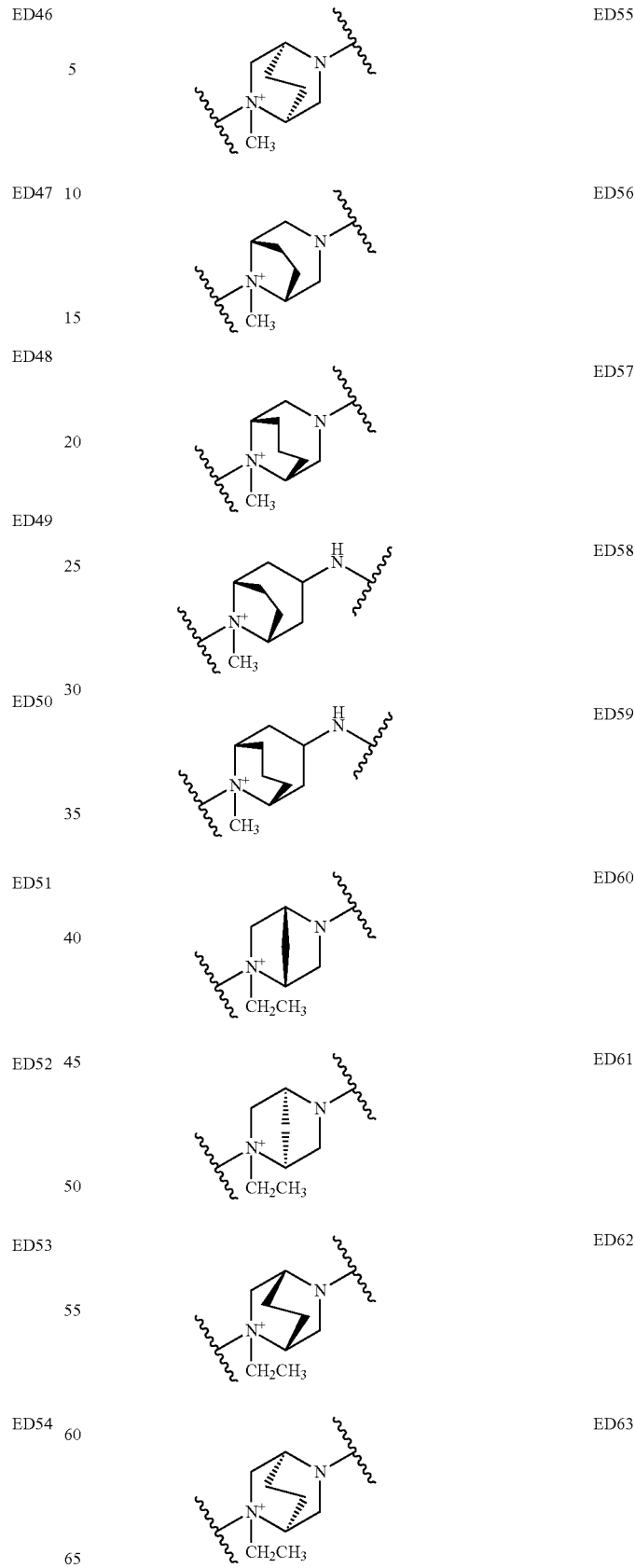

TABLE 8-continued
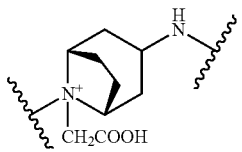 ED64
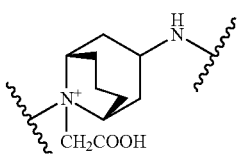 ED65
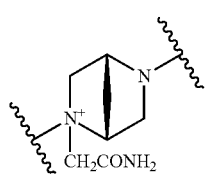 ED66
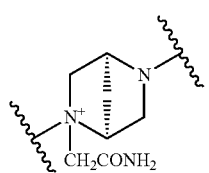 ED67
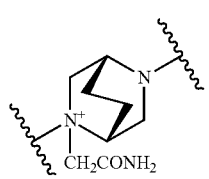 ED68
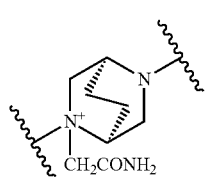 ED69
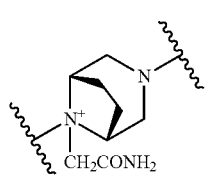 ED70
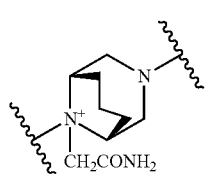 ED71
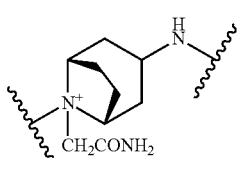 ED72
TABLE 9
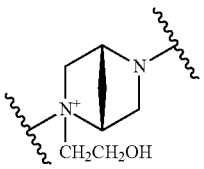 ED73
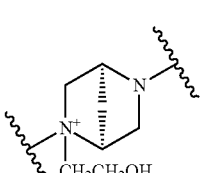 ED74
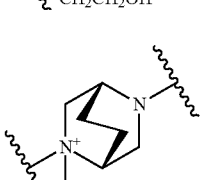 ED75
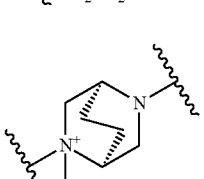 ED76
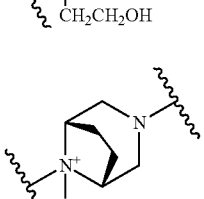 ED77
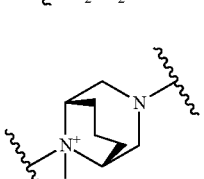 ED78
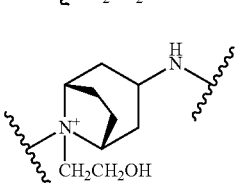 ED79
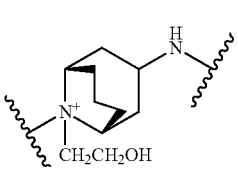 ED80
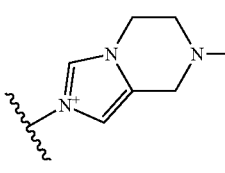 ED81

TABLE 9-continued
| | |
|---|---|
| 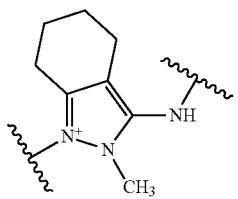 | ED82 |
| 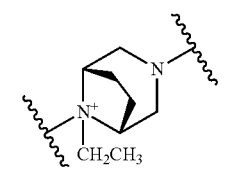 [SMILES: *N1C[C@H]2CC[C@@H](C1)[N+]2(*)CC] | ED83 |
| 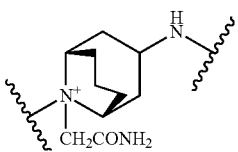 | ED84 |
| 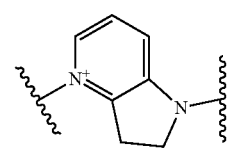 [SMILES: *N1CCc2c1ccc[n+]2*] | ED85 |
| 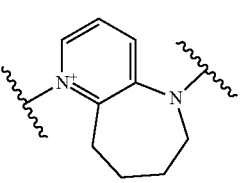 [SMILES: *N1CCCCc2c1ccc[n+]2*] | ED86 |
| 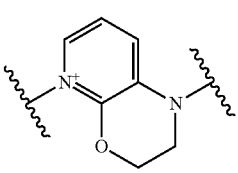 [SMILES: *N1CCOc2c1ccc[n+]2*] | ED87 |
| 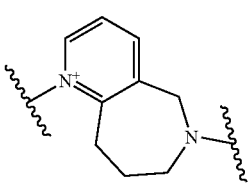 [SMILES: *N1CCCc2c(ccc[n+]2*)C1] | ED88 |
| 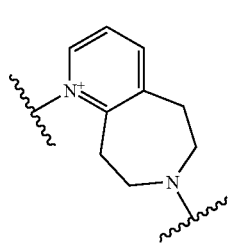 [SMILES: *N1CCc2ccc[n+](*)c2CC1] | ED89 |
TABLE 9-continued
| | |
|---|---|
| 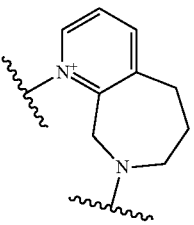 [SMILES: *N1CCCc2ccc[n+](*)c2C1] | ED90 |
TABLE 10
| | |
|---|---|
| 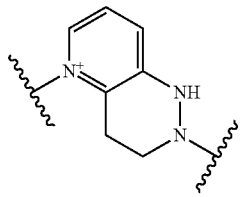 [SMILES: *N1CCc2c(ccc[n+]2*)N1] | ED91 |
| 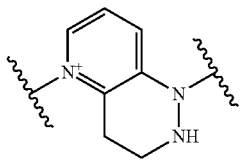 [SMILES: *N1NCCc2c1ccc[n+]2*] | ED92 |
| 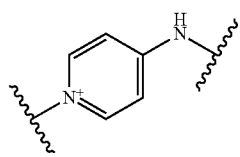 [SMILES: *Nc1cc[n+](*)cc1] | ED93 |
| 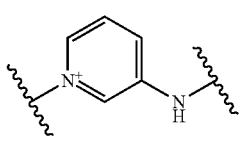 [SMILES: *Nc1ccc[n+](*)c1] | ED94 |
| 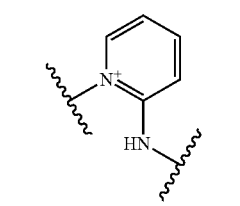 [SMILES: *Nc1cccc[n+]1*] | ED95 |
| 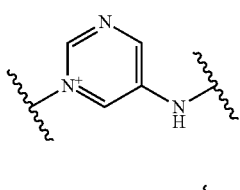 | ED96 |
| 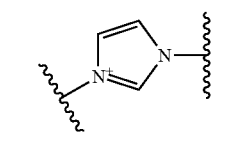 [SMILES: *n1cc[n+](*)c1] | ED97 |

TABLE 10-continued

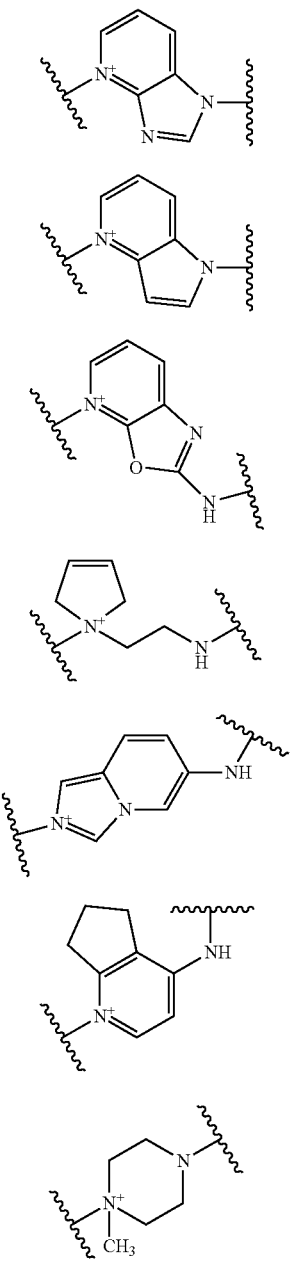

ED98

ED99

ED100

ED101

ED102

ED103

ED104

Test Example 1

Compound (I) of the subject invention has been investigated for in vitro antimicrobial activity thereof.

(Test Methods for Compounds (I-1) to (I-9), (I-16), (I-17) and (I-23))

(Microbe/Strain Species Nos. 1 to 4 and 6 to 8):

Measurement of Minimum Inhibitory Concentration (MIC: microgram/ml) was conducted according to the standard method of the Japan Society for Chemotherapy, and the amount of bacteria for inoculation was 1000 cfu/spot, and sensitive disc medium was used as the test medium, and conducted using agar plate incubation.

(Microbe/Strain Species No. 5):

Measurement of Minimum Inhibitory Concentration (MIC, microgram/ml) was conducted according to the CLSI (Clinical and Laboratory Standards Institute) and the amount of bacteria for inoculation was 10000 cfu/spot, and Mueller-Hinton agar medium was used as the test medium, and conducted using agar plate incubation.

(Test Methods for Compounds (I-10) to (I-15))

(Microbe/Strain Species Nos. 1 to 5):

Measurement of Minimum Inhibitory Concentration (MIC, microgram/ml) was conducted according to the CLSI (Clinical and Laboratory Standards Institute) and the amount of bacteria for inoculation was $5 \times 10^5$ cfu/mL, and cation adjusted Mueller-Hinton liquid medium added human Apotranferrin was used as the test medium, and conducted using broth microdilution method.

(Microbe/Strain Species Nos. 6 to 8):

Measurement of Minimum Inhibitory Concentration (MIC, microgram/ml) was conducted according to the CLSI (Clinical and Laboratory Standards Institute) and the amount of bacteria for inoculation was $5 \times 10^5$ cfu/mL, and cation adjusted Mueller-Hinton liquid medium was used as the test medium, and conducted using broth microdilution method.

(Test Methods for Compounds (I-18) to (I-22))

(Microbe/Strain Species Nos. 1 to 5):

Measurement of Minimum Inhibitory Concentration (MIC, microgram/ml) was conducted according to the CLSI (Clinical and Laboratory Standards Institute) and the amount of bacteria for inoculation was $5 \times 10^5$ cfu/mL, and cation adjusted Mueller-Hinton liquid medium added human Apotranferrin was used as the test medium, and conducted using broth microdilution method.

Test results are shown in Table 11. In the table, the unit of the values of inhibitory activity is microgram/ml (µg/ml).

TABLE 11

| Bacteria/Strain No. | Bacteria Species | Strain Name | Classification | Compound (I-1) | Compound (I-8) | Compound (I-9) | Compound (I-15) | Compound (I-17) | Compound (I-18) | Compound (I-23) |
|---|---|---|---|---|---|---|---|---|---|---|
| 1 | Klebsiella pneumoniae | ATCC 700603 | Gram negative bacteria | 1 | 0.5 | 4 | 32 | 4 | 2 | 16 |
| 2 | Pseudomonas aeruginosa | SR24 | Gram negative bacteria | 0.063 | 0.25 | 0.25 | 0.5 | 0.25 | 0.125 | 0.5 |
| 3 | Pseudomonas aeruginosa | SR27060 | Gram negative bacteria | 0.5 | 2 | 1 | 2 | 1 | 2 | 4 |
| 4 | Acinetobacter baumannii | SR24396 | Gram negative bacteria | 0.5 | 0.25 | 1 | 4 | 1 | 0.25 | 1 |
| 5 | Stenotrohomonas maltophilia | SR21970 | Gram negative bacteria | 2 | 4 | 2 | 0.5 | 2 | 4 | >64 |

TABLE 11-continued

| Bacteria/Strain No. | Bacteria Species | Strain Name | Classification | Compound (I-1) | Compound (I-8) | Compound (I-9) | Compound (I-15) | Compound (I-17) | Compound (I-18) | Compound (I-23) |
|---|---|---|---|---|---|---|---|---|---|---|
| 6 | *Staphylococcus aureus* | Smith | Gram positive bacteria | 4 | — | — | — | — | — | — |
| 7 | *Streptococcus pneumoniae* | Type I | Gram positive bacteria | 0.5 | 4 | — | — | — | — | 0.5 |
| 8 | *Streptococcus pneumoniae* | SR16675 | Gram positive bacteria | 8 | — | — | — | — | — | — |

Description of the bacterial species in the above table, enzymes (beta-lactamase) produced thereby, and the strain types are shown in Table 12 below.

TABLE 12

| Bacteria Species | Strain Name | Enzyme Produced | Strain Type |
|---|---|---|---|
| 1 *K. pneumoniae* | ATCC700603 | SHV-18 | ESBL producing strain |
| 2 *P. aeruginosa* | SR24 | None | Ceftazidime sensitive strain |
| 3 *P. aeruginosa* | SR27060 | IMP-1 | MBL producing strain (carbapenem resistant strain) |
| 4 *A. baumannii* | SR24396 | None | |
| 5 *S. maltophilia* | SR21970 | L-1 | MBL producing strain (carbapenem resistant strain) |
| 6 *S. aureus* | Smith | None | MSSA (methicillin susceptible *Staphylococcus aureus*) |
| 7 *S. pneumoniae* | Type I | None | PSSP (penicillin susceptible *Streptococcus pneumoniae*) |
| 8 *S. pneumoniae* | SR16675 | None | PRSP (penicillin resistant *Streptococcus pneumoniae*) |

Test Example 2

Compound (I) of the subject invention is investigated for in vitro antimicrobial activity thereof.

(Test Methods)

Mice (ICR series, male, 5-week-old) were inoculated intraperitoneally with *P. aeruginosa* SR27001 (multidrug-resistant *Pseudomonas aeruginosa*; IMP-1 producing strain) to raise infection. One and half hours after, mice were treated with intravenous administration in twice, and then the ED50 value was calculated based on the survival rate after 7 days.

As shown in the above results, the compounds of the subject invention were shown to have a wide antimicrobial spectrum, in particular, potent antimicrobial spectrum against Gram negative bacteria, and/or effectiveness against multidrug-resistant bacteria, and exhibited high stability against beta-lactamase producing Gram negative bacteria. In comparison to cefepime hydrochloride hydrate (CFPM), commercially available as a beta-lactamase resistant cephalosporin antibiotics having similar structure, it was shown that the compounds of the subject invention have more potent antimicrobial activity. Consequently, it was shown that the compounds of the subject invention are useful as pharmaceutical products.

Formulation Example 1

Powder of the compound of the subject invention is loaded to prepare a formulation for injection.

INDUSTRIAL APPLICABILITY

The compounds of the subject invention have a wide antimicrobial spectrum, and are effective as an antimicrobial drug having high stability against beta-lactamase producing Gram negative bacteria. Moreover, the subject compounds have good bioavailability, and high water solubility, and thus particularly useful for injectable formulation.

The invention claimed is:

1. A compound of the formula:

[Formula 1]

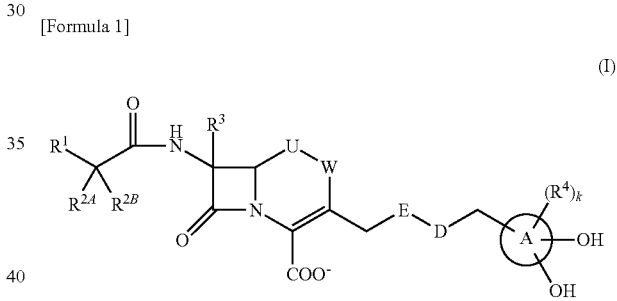

(I)

or an ester, a protected compound at the amino on the ring in the 7-side chain, a pharmaceutically acceptable salt, or a solvate thereof,
wherein
W is —CH$_2$—, —S—, or —O—; provided that
a) when W is —CH$_2$—, then U is —CH$_2$—, —S—, or —O—, and
b) when W is —S— or —O—, then U is —CH$_2$—;
  $R^1$ is an optionally substituted carbocyclic group, or optionally substituted heterocyclic group;
  with regard to $R^{2A}$ and $R^{2B}$,
a) $R^{2A}$ is an optionally substituted amino group, —SO$_3$H, optionally substituted aminosulfonyl group, carboxyl group, optionally substituted (lower alkyl)oxycarbonyl group, optionally substituted carbamoyl group, hydroxyl group, or a substituted carbonyloxy group; and $R^{2B}$ is a hydrogen atom, or
b) $R^{2A}$ and $R^{2B}$ are taken together to form an optionally substituted alkenyl group, or optionally substituted oxime group,
  provided that when $R^1$ is an aminothiazole of which the amino group is optionally protected, or an aminothiadiazole of which the amino group is optionally protected, $R^{2A}$ and $R^{2B}$ are not taken together to form an optionally substituted oxime group;

ring A is a benzene ring, or 6-membered aromatic heterocyclic group having 1-3 nitrogen atoms;

$R^3$ is a hydrogen atom, —$OCH_3$, or —NH—CH(=O);

k is an integer from 0 to 2;

each $R^4$ is independently a hydrogen atom, halogen, hydroxyl group, —CN, —C(=O)—$R^6$, —C(=O)—OH, —C(=O)—$OR^6$, or —$OR^6$;

$R^6$ is a lower alkyl or halo(lower)alkyl; and with regard to D and E, a) D is a single bond, —N($R^8$)—, or —$R^7$—N($R^8$)— wherein $R^7$ is an optionally substituted lower alkylene, and $R^8$ is a hydrogen or lower alkyl; and E is an optionally substituted quaternary ammonium group of the formula selected from the following formula (1) to (40) and (42) to (53), or b) D has the formula:

[Formula 2]

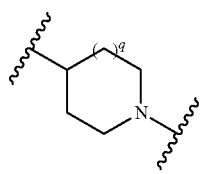

wherein q is an integer of 0 or 1, and E has the formula of a quaternary ammonium group represented by the following formula (10) or (41);

[Formula 3]

(1)

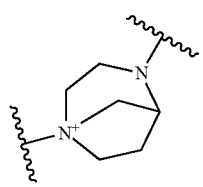

(2)

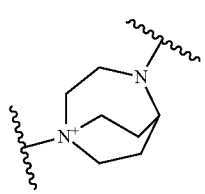

(3)

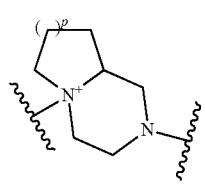

(4)

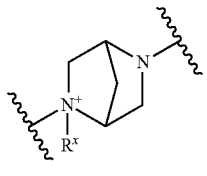

(5)

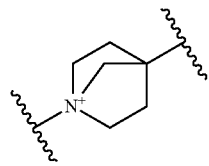

(6)

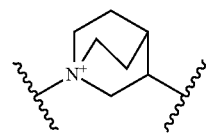

(7)

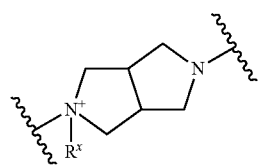

(8)

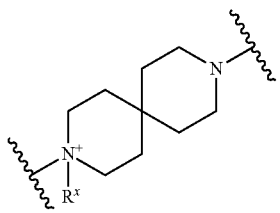

(9)

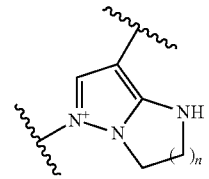

(10)

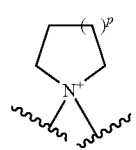

(11)

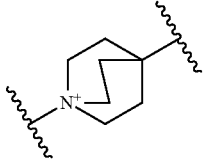

(12)

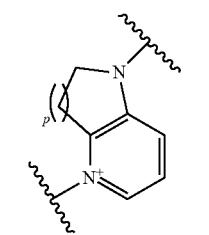

133
-continued
(13)
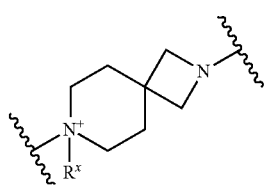
(14)
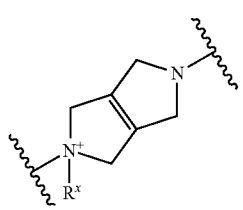
(15)
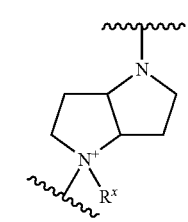
(16)
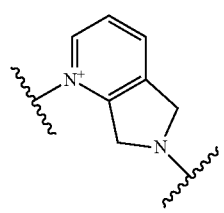
(17)
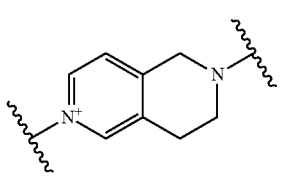
(18)
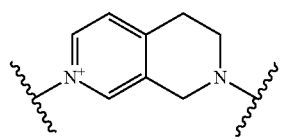
(19)
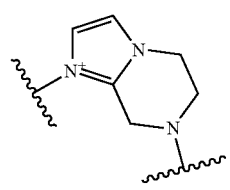
(20)
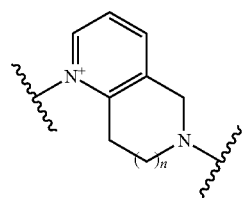
134
-continued
(21)
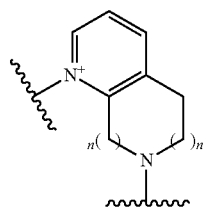
(22)
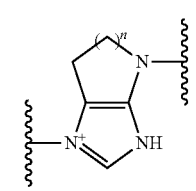
(23)
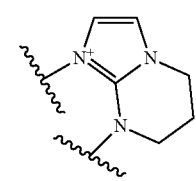
(24)
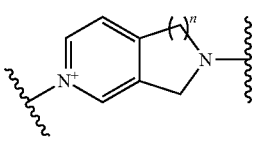
(25)
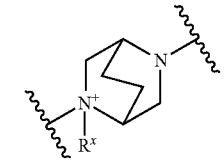
(26)
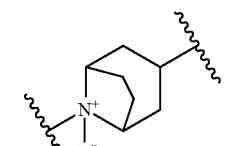
(27)
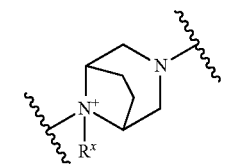
(28)
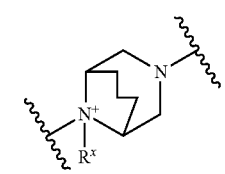

[Formula 4]
(29) 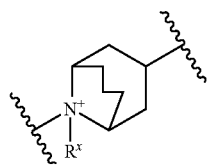
(30) 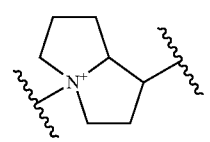
(31) 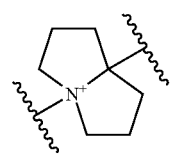
(32) 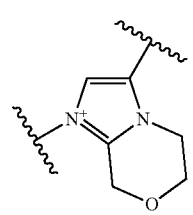
(33) 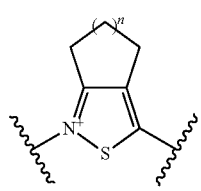
(34) 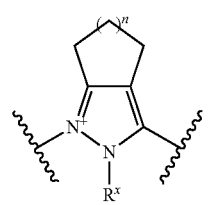
(35) 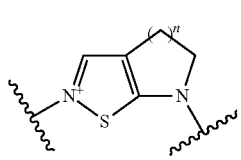
(36) 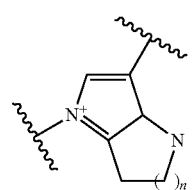
(37) 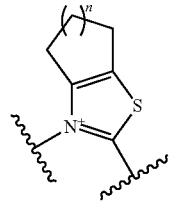
(38) 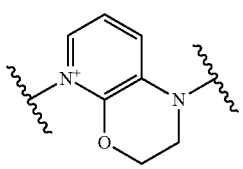
(39) 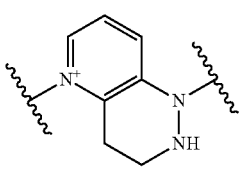
(40) 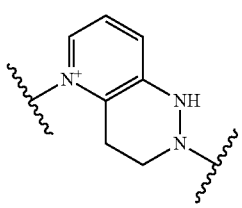
(41) 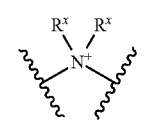
(42) 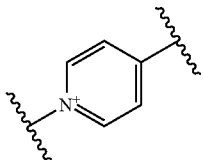
(43) 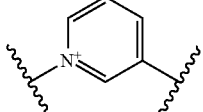
(44) 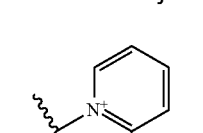
(45) 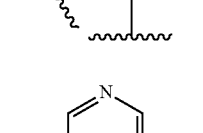

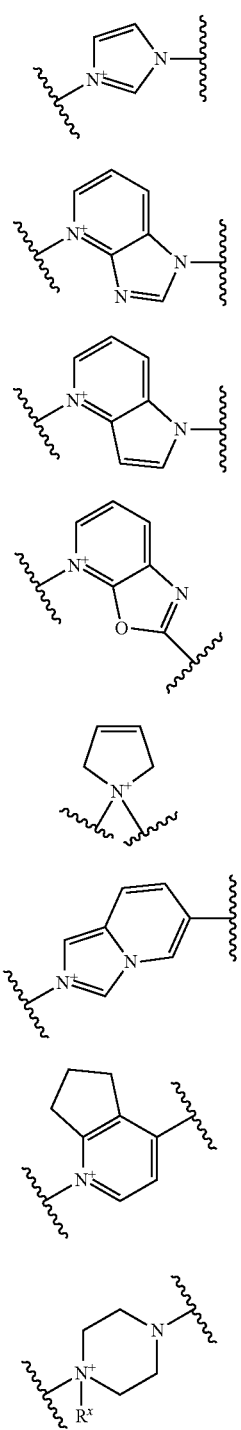

wherein p is an integer from 1 to 3; n is an integer of 1 or 2; $R^x$ is an optionally substituted lower alkyl; the left side of attachment binds to methylene; and the right side of attachment binds to D, provided that the case where $R^1$ is a phenyl and E has the formula (53) is excluded.

2. The compound, or an ester, a protected compound at the amino on the ring in the 7-side chain, a pharmaceutically acceptable salt, or a solvate thereof according to claim 1, wherein D is a single bond, —NH—, or —$R^7$—NH— wherein $R^7$ is as defined in claim 1.

3. The compound, or an ester, a protected compound at the amino on the ring in the 7-side chain, a pharmaceutically acceptable salt, or a solvate thereof according to claim 1, wherein D is —NH—, —CH$_2$—NH—, or —CH$_2$—CH$_2$—NH—.

4. The compound, or an ester, a protected compound at the amino on the ring in the 7-side chain, a pharmaceutically acceptable salt, or a solvate thereof according to claim 1, wherein D is a single bond.

5. The compound, or an ester, a protected compound at the amino on the ring in the 7-side chain, a pharmaceutically acceptable salt, or a solvate thereof according to claim 1, wherein D has the formula of:

[Formula 5]

wherein q is as defined in claim 1.

6. The compound, or an ester, a protected compound at the amino on the ring in the 7-side chain, a pharmaceutically acceptable salt, or a solvate thereof according to claim 1, wherein E is selected from formula (1) to (9), (11) to (40), (47) to (49), (51) and (52).

7. The compound, or an ester, a protected compound at the amino on the ring in the 7-side chain, a pharmaceutically acceptable salt, or a solvate thereof according to claim 1, wherein E is selected from formula (5), (6), (9) to (11), (26), (29) to (34), (36), (37) and (50).

8. The compound, or an ester, a protected compound at the amino on the ring in the 7-side chain, a pharmaceutically acceptable salt, or a solvate thereof according to claim 1, wherein E is selected from formula (5), (6), (10) and (11).

9. The compound, or an ester, a protected compound at the amino on the ring in the 7-side chain, a pharmaceutically acceptable salt, or a solvate thereof according to claim 1, wherein E is selected from formula (1) to (4), (7), (8), (12) to (25), (27), (28), (35), (38) to (40), (47) and (48).

10. The compound, or an ester, a protected compound at the amino on the ring in the 7-side chain, a pharmaceutically acceptable salt, or a solvate thereof according to claim 1, wherein E is selected from formula (1) to (3), (7) and (12).

11. The compound, or an ester, a protected compound at the amino on the ring in the 7-side chain, a pharmaceutically acceptable salt, or a solvate thereof according to claim 1, wherein U is —S—.

12. The compound, or an ester, a protected compound at the amino on the ring in the 7-side chain, a pharmaceutically acceptable salt, or a solvate thereof according to claim 1, wherein W is —CH$_2$—.

13. The compound, or an ester, a protected compound at the amino on the ring in the 7-side chain, a pharmaceutically acceptable salt, or a solvate thereof according to claim 1, wherein $R^3$ is a hydrogen atom or —OCH$_3$.

14. The compound, or an ester, a protected compound at the amino on the ring in the 7-side chain, a pharmaceutically acceptable salt, or a solvate thereof according to claim 1, wherein the formula:

[Formula 6]
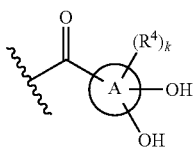
is selected from the following:
[Formula 7]
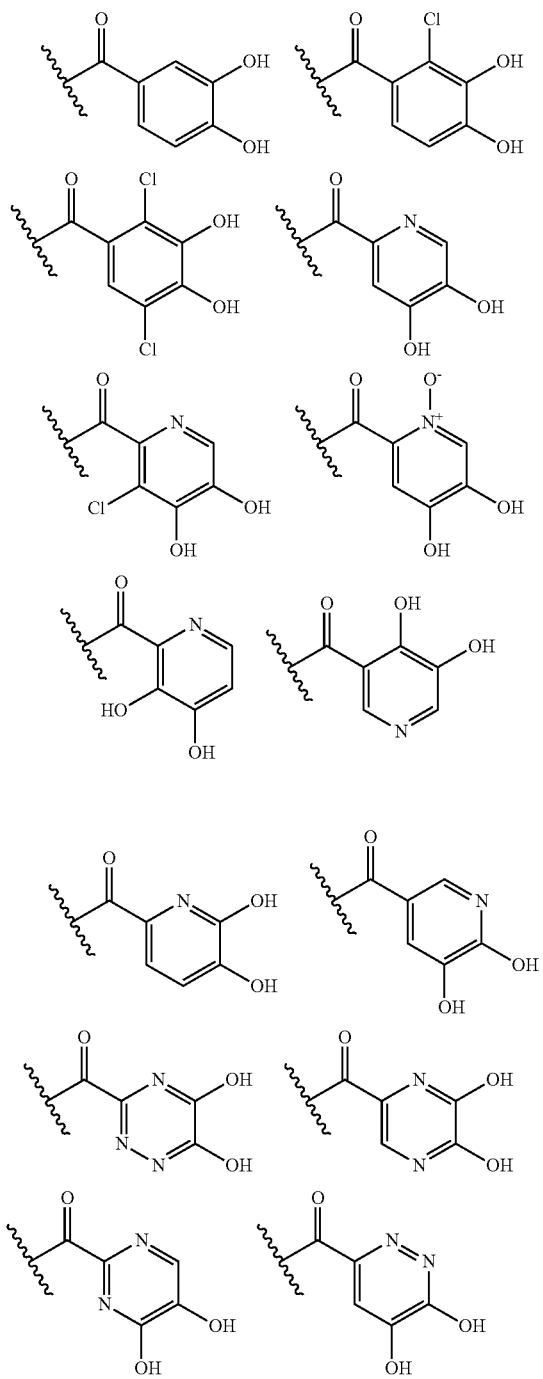
-continued
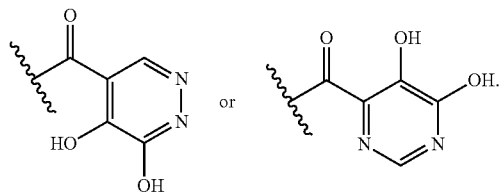
15. The compound, or an ester, a protected compound at the amino on the ring in the 7-side chain, a pharmaceutically acceptable salt, or a solvate thereof according to claim 1, wherein the formula:
[Formula 8]
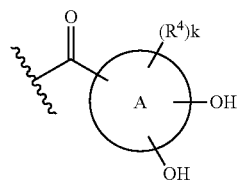
is selected from the following:
[Formula 9]
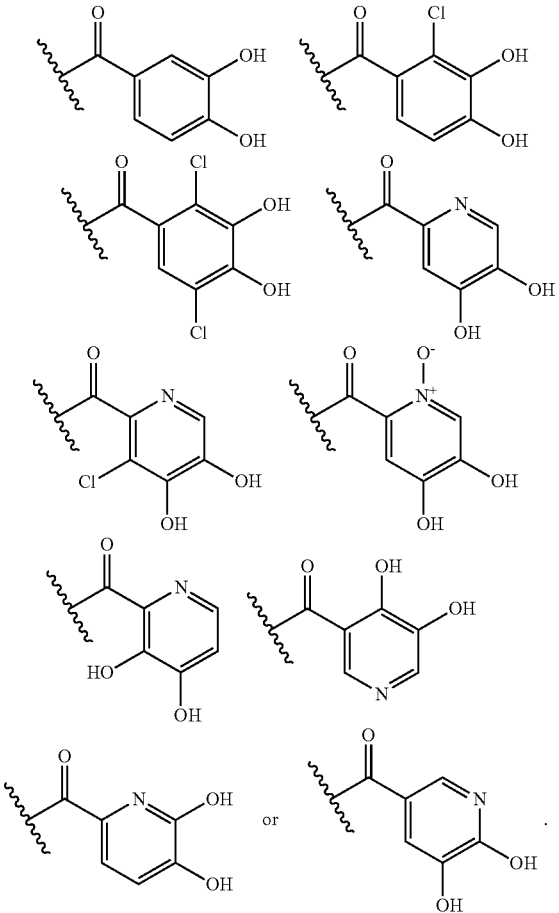

16. The compound, or an ester, a protected compound at the amino on the ring in the 7-side chain, a pharmaceutically acceptable salt, or a solvate thereof according to claim 1, wherein the formula:

[Formula 10]

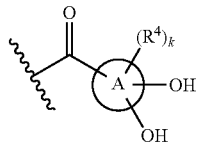

is selected from the following:

[Formula 11]

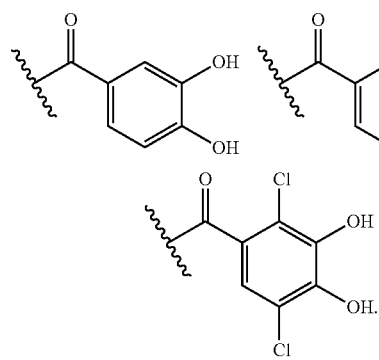

17. The compound, or an ester, a protected compound at the amino on the ring in the 7-side chain, a pharmaceutically acceptable salt, or a solvate thereof according to claim 1, wherein $R^1$ is an optionally substituted phenyl.

18. The compound, or an ester, a protected compound at the amino on the ring in the 7-side chain, a pharmaceutically acceptable salt, or a solvate thereof according to claim 1, wherein $R^{2A}$ is an optionally substituted amino group, —$SO_3H$, optionally substituted aminosulfonyl group, carboxyl group, optionally substituted carbamoyl group, hydroxyl group, or substituted carbonyloxy group.

19. The compound, or an ester, a protected compound at the amino on the ring in the 7-side chain, a pharmaceutically acceptable salt, or a solvate thereof according to claim 1, wherein $R^{2A}$ is selected from a substituted amino group shown below:

[Formula 12]

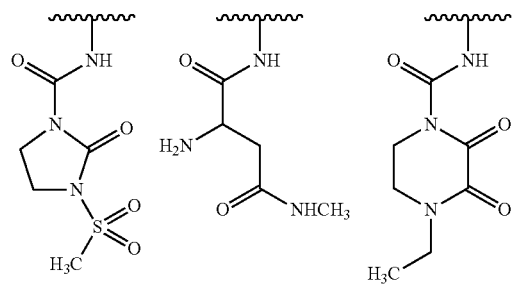

-continued

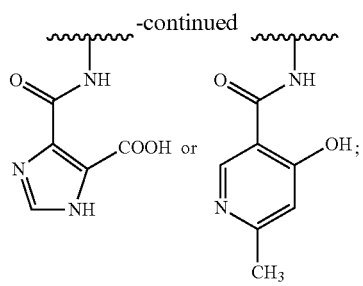

a substituted aminosulfonyl group shown below:

[Formula 13]

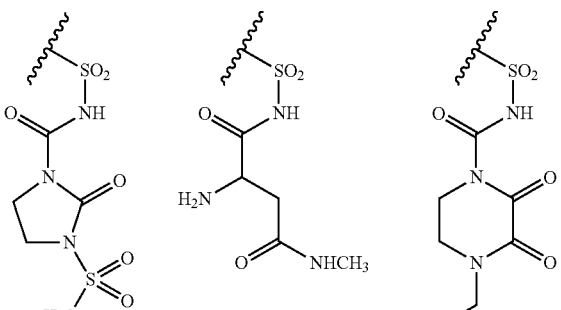

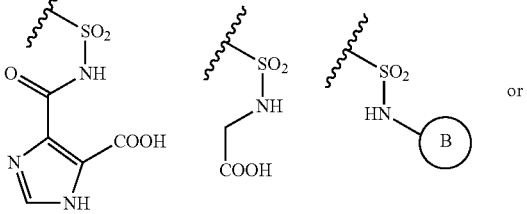

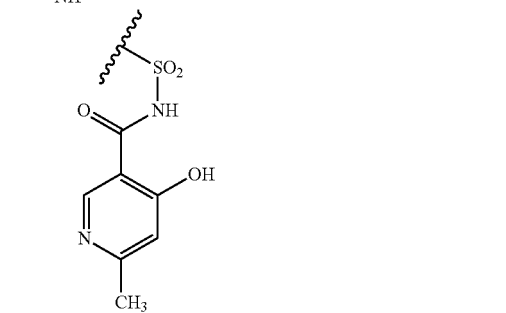

wherein ring B represents an optionally substituted heterocyclic group;

a substituted carbamoyl group shown below:

[Formula 14]

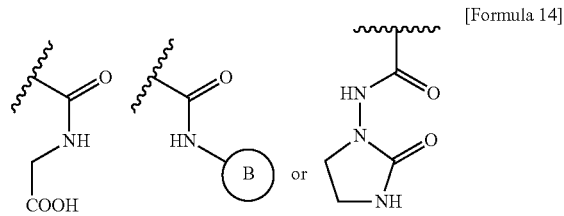

wherein ring B represents an optionally substituted heterocyclic group; or a substituted carbonyloxy group shown below:

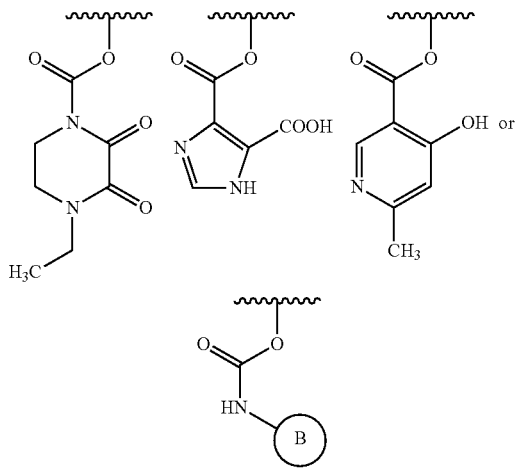

[Formula 15]

wherein ring B represents an optionally substituted heterocyclic group.

20. The compound, or an ester, a protected compound at the amino on the ring in the 7-side chain, a pharmaceutically acceptable salt, or a solvate thereof according to claim 1, wherein $R^{2A}$ and $R^{2B}$ are taken together to form a substituted alkenyl group shown below:

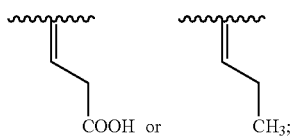

[Formula 16]

or a substituted oxime group shown below:

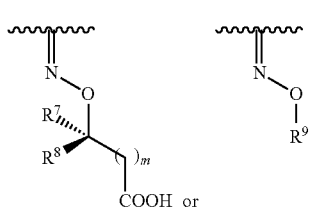

[Formula 17]

wherein $R^7$ and $R^8$ are each independently a hydrogen atom, halogen, hydroxy, carboxy, optionally substituted lower alkyl, optionally substituted carbocyclic group, or optionally substituted heterocyclic group, or $R^7$ and $R^8$ may be taken together with a neighboring atom to form an optionally substituted carbocyclic group or optionally substituted heterocyclic group;

$R^9$ is an optionally substituted lower alkyl; and m is an integer from 0 to 3.

21. A pharmaceutical composition, which comprises a compound, or an ester, a protected compound at the amino on the ring in the 7-side chain, a pharmaceutically acceptable salt, or a solvate thereof according to claim 1.

22. The pharmaceutical composition according to claim 21, which possesses antimicrobial activity.

\* \* \* \* \*